(12) United States Patent
Budin et al.

(10) Patent No.: US 10,274,490 B2
(45) Date of Patent: Apr. 30, 2019

(54) MAGNETIC LABELING OF BACTERIA

(71) Applicant: The General Hospital Corporation, Boston, MA (US)

(72) Inventors: Ghyslain Budin, Boston, MA (US); Ralph Weissleder, Peabody, MA (US); Hakho Lee, Acton, MA (US); Hyun Jung Chung, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 238 days.

(21) Appl. No.: 14/407,300

(22) PCT Filed: Mar. 8, 2013

(86) PCT No.: PCT/US2013/029819
§ 371 (c)(1),
(2) Date: Dec. 11, 2014

(87) PCT Pub. No.: WO2013/187954
PCT Pub. Date: Dec. 19, 2013

(65) Prior Publication Data
US 2015/0125884 A1    May 7, 2015

Related U.S. Application Data

(60) Provisional application No. 61/658,559, filed on Jun. 12, 2012.

(51) Int. Cl.
*B82Y 30/00* (2011.01)
*G01N 33/569* (2006.01)
(Continued)

(52) U.S. Cl.
CPC ........ *G01N 33/56911* (2013.01); *B82Y 30/00* (2013.01); *G01N 33/56938* (2013.01);
(Continued)

(58) Field of Classification Search
None
See application file for complete search history.

(56) References Cited

U.S. PATENT DOCUMENTS 5,262,176 A   11/1993  Palmacci et al.
5,492,814 A    2/1996  Weissleder
(Continued)

FOREIGN PATENT DOCUMENTS

WO    WO 00/61191         10/2000
WO    WO-2010-036827 A1 *  4/2010
WO        2011/030160      3/2011

OTHER PUBLICATIONS

Haun et al., "Bioorthogonal chemistry amplifies nanoparticle binding and enhances the sensitivity of cell detection", Nature Nanotechnology, vol. 5, pp. 660-665, published Aug. 1, 2010.*
(Continued)

*Primary Examiner* — Tracy Vivlemore
*Assistant Examiner* — Nam P Nguyen
(74) *Attorney, Agent, or Firm* — Fish & Richardson P.C.

(57) ABSTRACT

The present invention provides novel methods of magnetically labeling a bacterial cell by contacting the call with an affinity ligand and subsequently contacting the cell with a magnetic agent, where the affinity ligand and magnetic agent include bioorthogonally reactive groups that can react with each other to form a covalent bond. Compounds, compositions, kits and applications of the method are also described.

37 Claims, 23 Drawing Sheets

(51) Int. Cl.
  *G01N 33/58* (2006.01)
  *G01N 24/08* (2006.01)
(52) U.S. Cl.
  CPC ..... *G01N 33/56944* (2013.01); *G01N 33/585* (2013.01); *G01N 24/08* (2013.01); *G01N 2458/00* (2013.01)

(56) References Cited

U.S. PATENT DOCUMENTS

2009/0023916 A1  1/2009  Fox et al.
2012/0034161 A1  2/2012  Robillard et al.

OTHER PUBLICATIONS

Organic Chemistry Portal (print retrieved May 17, 2017).*
Agard et al., "A strain-promoted [3+2] azide-alkyne cycloaddition for covalent modification of biomolecules in living systems," J. Am. Chem. Soc., 2004, 126 (46): 15046-15047.
Backus et al., "Uptake of unnatural trehalose analogs as a reporter for *Mycobacterium tuberculosis*," Nat. Chem. Biol., 2011, 7(4): 228-235.
Bartholomew et al., "The Gram Stain," Bacteriol Rev., 1952, 16(1): 1-29.
Baskin et al., "Copper-free click chemistry for dynamic in vivo imaging," Proc. Natl. Acad. Sci., 2007, 104(43): 16793-16797.
Beveridge, "Use of the gram stain in microbiology," Biotech. Histochem, 2001, 76(3): 111-8.
Blackman et al., "Tetrazine ligation: fast bioconjugation based on inverse-electron-demand diels-alder reactivity," J. Am. Chem. Soc., 2008, 130(4): 13518-13519.
Bottone, "The Gram Stain: The Century-Old Quintessential Rapid Diagnostic Test," Lab. Med., 1988, 19(5): 288-9.
Chaves, et al., "Single molecule actuation and detection on a lab-on-a-chip magnetoresistive platform," J. Appl. Phys., 2011, 109: 064702.
Chen et al., "Bioorthogonal Chemistry for site-specific labeling and surface immobilization of proteins," Acc. Chem. Res., 2011, 44(9), 762-773.
Chenoweth et al., "Cyclooctyne-based reagents for uncatalyzed click chemistry: A computational survey," Org. Biomol. Chem., 2009, 7:5255-5258.
De Smet et al., Three pathways for trehalose biosynthesis in mycobacteria Microbiology, 2000, 146: 199-208.
Devaraj et al., "Bioorthogonal turn-on probes for imaging small molecules inside living cells," Angew. Chem. Int. Ed., 2010, 49(16): 2869-2872.
Devaraj et al., "Tetrazine-based cycloadditions: Application to pretargeted live cell imaging," Bioconj. Chem., 2008, 19(12): 2297-2299.
Devraj et al., "Fast and sensitive pretargeted labeling of cancer cells via tetrazine /trans-cyclooctene cycloaddition," Angew. Chem., Int. Ed. Engl., 2009, 48(38): 7013-7016.
Diamandis et al., "The biotin-(strept) avidin system: Principles and applications in biotechnology," Clin. Chem., 1991, 37(5): 625-636.
Dommerholt et al., "Readily accessible bicyclononynes for bioorthogonal labeling and three-dimensional imaging of living cells," Angew. Chem. Int. Ed., 2010, 49(49): 9422-9425.
Guillebault, et al., "Improved method for bacterial cell capture after flow cytometry cell sorting," Appl. Environ. Microbial., 2010, 76(21): 7352-7355.
Halbreich et al., "Biomedical applications of maghemite ferrofluid," Biochimie, 1998, 80(5-6): 379-90.
Haun et al., "Bioorthogonal chemistry amplifies nanoparticle binding and enhances the sensitivity of cell detection," Nat. Nanotechnol., 2010, 5(9): 660-665.
Haun et al., "Probing intracellular biomarkers and mediators of cell activation using nanosensors and biorthogonal chemistry," ACS Nano, 2011, 5(4): 3204-3213.
Hoffmann et al., "Disclosure of the mycobacterial outer membrane: cryo-electron tomography and vitreous sections reveal the lipid bilayer structure," Proc. Natl. Acad. Sci., 2008, 105(10): 3963-3967.
Hogemann, et al., "Improvement of MRI probes to allow efficient detection of gene expression," Bioconjug. Chem., 11(6): 941-46, 2000.
International Preliminary Report on Patentability in International Application No. PCT/US2013/029819, dated Dec. 16, 2014, 6 pages.
Issadore et al., "Miniature magnetic resonance system for point-of-care diagnostics," Lab Chip, 2011, 11(13): 2282-87.
Jewett et al., "Rapid Cu-free click chemistry with readily synthesized biarylazacyclooctynones," J. Am. Chem. Soc., 2010, 132(11): 3688-3690.
Josephson et al., "High-efficiency intracellular magnetic labeling with novel superparamagnetic-Tat peptide conjugates," Bioconjug. Chem., 1999, 10(2): 186-91.
Kolb et al., "Click chemistry: Diverse chemical function from a few good reactions," Angew. Chem. Int. Ed., 2001, 40(11): 2004-2021.
Lee et al., "Rapid detection and profiling of cancer cells in fine-needle aspirates," Proc. Natl. Acad. Sci., 2009, 106(30): 12459-12464.
Lim et al., "Bioorthogonal chemistry: recent progress and future directions," Chem. Commun. (Camb.), 2010, 46(10): 1589-600.
Link et al., "Cell Surface Labeling of *Escherichia coli* via Copper(I)-Catalyzed [3+2] Cycloaddition," J. Am. Chem. Soc., 2003, 125: 11164-11165.
Link et al., "Non-canonical amino acids in protein engineering," Curr. Opin. Biotechnol. 2003, 14(6): 603-609.
Liong et al., "Specific pathogen detection using biorthogonal chemistry and diagnostic magnetic resonance," Bioconjug Chem, 2011, 22(12): 2390-4.
Lonnbro et al., "Isolation of bacteria-containing phagosomes by magnetic selection," BMC Cell Biology, 2008, 9: 35.
Marks et al., "Strain-promoted "click" chemistry for terminal labeling of DNA," Bioconjugate Chem., 2011, 22(7): 1259-1263.
Molday et al., "Immunospecific ferromagnetic iron-dextran reagents for the labeling and magnetic separation of cells," J. Immunol. Methods, 1982, 52(3): 353-67.
Nagarajan et al., "Antibacterial activities and modes of action of vancomycin and related glycopeptides," Antimicrob. Agents Chemother., 1991, 35(4): 605-609.
Panizzi et al., "In vivo detection of *Staphylococcus aureus* endocarditis by targeting pathogen-specific prothrombin activation," Nat Med., 2011, 17(9): 1142-6.
Prescher et al., "Chemical remodeling of cell surfaces in living animals," Nature, 2004, 430(7002): 873-77.
Prescher et al., "Chemistry in living systems," Nature Chemical Biology, 1(1): 13-21, 2005.
Reynolds, "Structure, biochemistry and mechanism of action of glycopeptide antibiotics," Eur. J. Clin. Microbial. Infect. Dis., Nov. 1989, 8(11): 943-950.
Rostovtsev et al. "A stepwise huisgen cycloaddition process: copper(I)-catalyzed regioselective "ligation" of azides and terminal alkynes," Angew. Chem. Int. Ed., 2002, 41(14): 2596-2599.
Saxon and Bertozzi, "Cell surface engineering by a modified Staudinger Reaction," Science, Mar. 2000, 287(5460): 2007-10.
Seelig and Jaschke, "Site-specific modification of enzymatically synthesized RNA: Transcription initiation and Diela-Alder reaction," Tetrahedron Lett., 1997, 38(44): 7729-7732.
Shen et al., "Magnetically labeled secretin retains receptor affinity to pancreas acinar cells" Bioconjug. Chem., 1996, 7(3): 311-16.
Sletten et al., "Bioorthogonal chemistry: fishing for selectivity in a sea of functionality," Angew. Chem. Int. Ed., 2009, 48(38): 6974-6998.
Sletten et al., "From mechanism to mouse: a tale of two biorthogonal reactions," Acc. Chem. Res., 2011, 44(9), 666-676.
Steenbergen et al., "Daptomycin: a lipopeptide antibiotic for the treatment of serious Gram-positive infections," J. Antimicrob. Chemother., 2005, 55(3): 283-288.
Wang et al., "Bioconjugation by Copper(I)-Catalyzed Azide-Alkyne [3+2] Cycloaddition," J. Am. Chem. Soc., 2003, 12, 3192-3193.

(56) References Cited

OTHER PUBLICATIONS

Yang et al., "Rapid concentration of bacteria using submicron magnetic anion exchanges for improving PCR-based multiplex pathogen detection," J. Microbial. Methods, 2011, 86(1): 69-77.

Yousaf et al., "Diel-Alder Reaction for the selective immobilization of protein to electroactive self-assembled monolayers," J. Am. Chem. Soc., 1999, 121: 4286-4287.

Zhang et al., "Magnetic force microscopy of iron oxide nanoparticles and their cellular uptake," Biotechnol. Prog., 2009, 25(4): 923-928.

\* cited by examiner

MAGNETIC LABELING OF BACTERIA

CROSS-REFERENCE TO RELATED APPLICATIONS

This application is a U.S. National Phase Application under 35 U.S.C. § 371 of International Patent Application No. PCT/US2013/029819, filed on Mar. 8, 2013, which claims the benefit of U.S. Provisional Application No. 61/658,559, filed Jun. 12, 2012 The entire contents of the foregoing are hereby incorporated by reference herein.

TECHNICAL FIELD

This invention relates to diagnostic methods and compounds, and more particularly to a method and compounds for selectively labeling bacteria with magnetic particles to assist in detecting and analyzing such bacteria.

BACKGROUND

Although many bacteria are harmless or beneficial, some bacteria are pathogenic and can cause disease. Tuberculosis, caused by the bacterium *Mycobacterium tuberculosis*, kills about 2 million people a year worldwide. Pathogenic bacteria contribute to other important diseases, such as pneumonia, which can be caused by bacteria such as *Streptococcus* and *Pseudomonas* bacteria, and food borne illnesses, which can be caused by bacteria such as *Shigella, Campylobacter* and *Salmonella*. Other disease-causing bacteria include *Bacillus anthracis* (anthrax), *Clostridum tetani* (tetanus), *Corynebacterium diphtheriae* (diphtheria), *Helicobacter pylori* (stomach ulcers), *Legionella pneumophila* (Legionnaire's disease), *Mycobacterium leprae* (leprosy), *Salmonella typhi* (typhoid fever), *Staphylococcus aureus* (sepsis), *Vibrio cholerae* (cholera) and *Yersinia Pestis* (bubonic plague). While the availability of antibiotics has rendered many bacterial diseases treatable, the emergence of antibiotic-resistant strains of bacteria has presented new challenges. There is therefore an ongoing need for the development of new analytical and diagnostic methods for studying and detecting bacteria.

Bacteria are often classified into Gram-positive and Gram-negative strains by their visual staining properties using crystal violet, a triarylmethane dye. The Gram staining method is a common tool for detecting and differentiating bacteria. Gram stains are commonly used for clinical diagnostic purposes, identification of a bacterial organism, as well as detecting them in environmental samples. The procedure involves staining bacterial samples with crystal violet (FIG. 1A), which binds to the peptidoglycan layer of Gram-positive and negative bacteria (FIG. 1B). As shown in FIG. 1B, Gram-positive and Gram-negative bacteria differ in the structure of their cell wall. Gram-positive bacteria have a thick peptidoglycan layer whereas Gram negative bacteria only have a thin peptidoglycan layer covered by lipopolysaccharides and lipoproteins. Subsequent treatment with iodine solution results in formation of an insoluble complex with crystal violet to form. Upon decolorization with alcohol or acetone, only Gram positive bacteria remain purple, while Gram-negatives lose the purple color. Beveridge, *Biotech. Histochem.*, 2001, 76, 111-8; Bartholomew et al., *Bacteriol. Rev.*, 1952, 16, 1-29; Bottone, *Lab. Med.*, 1988, 19, 288-91. Despite the simplicity and robustness of the staining procedure, the final detection still relies on optical microscopy which is user dependent and therefore not entirely error free.

A number of antibiotics have been developed to treat Gram-positive infections, many of which work either by inhibiting cell wall synthesis or by blocking transcription/translation processes. Vancomycin is a commonly used glycopeptide antibiotic, whose action primarily results in inhibition of cell wall synthesis. Specifically, vancomycin exerts its antibacterial activity by forming hydrogen bonds with the terminal D-alanyl-D-alanine (D-Ala-D-Ala) moieties of the N-acetylmuramic acid (NAM) and N-acetylglucosamine (NAG) peptide subunits. Nagarajan et al. *Antimicrob. Agents Chemother.* 1991, 35, 605-609; Reynolds, *Eur. J. Clin. Microbiol. Infect. Dis.* 1989, 8, 943-950. This binding prevents incorporation of the NAM/NAG-peptide subunits into the major structural component of Gram-positive cell walls, the peptidoglycan matrix, and thus results in inhibition of cell wall synthesis and ultimately bacterial cell death. The increasing prevalence of vancomycin-resistant organisms, however, have now led to the development of newer generation antibiotics including daptomycin, linezolide and pristinamycin. Daptomycin binds to the cell wall of Gram-positive bacteria via its hydrophobic tail, resulting in perturbation and depolarization of the cell membrane. Steenbergen, et al., *J. Antimicrob. Chemother.* 2005, 55, 283-288.

Trehalose, also known as mycose or tremalose, is a natural alpha-linked disaccharide formed by an α,α-1,1-glucoside bond between two α-glucose units. Trehalose is present as a free disaccharide in the cytoplasm of mycobacteria and as a component of cell-wall glycolipids implicated in tissue damage associated with mycobacterial infection, and is synthesized by *Mycobacteria* through three pathways. De Smet et al., *Microbiology*, 2000, 146, 199-208. Trehalose is found in the outer portion of the mycobacterial cell envelope along with the glycolipids trehalose dimycolate (TDM) and trehalose monomycolate (TMM). Hoffmann et al., *Proc. Natl. Acad. Sci. USA.* 2008, 105, 3963-3967. Uptake of unnatural trehalose analogs has been described as a reporter for mycobacteria such as *M. Tuberculosis*. Backus et al., *Nat. Chem. Biol.*, 2011, 7(4), 228-235; WO2011/030160.

Magnetic particles have been studied and used for a number of biomedical applications.

Preparations of magnetic particles designed for separation and extraction use particles that are amenable to easy manipulation by weak applied magnetic fields. These materials are typically micron sized and have a high magnetic moment per particle; their effects on water relaxation rate are unspecified and not relevant to their application. Smaller particles, in contrast, such as nanoparticles do not respond to the weak, magnetic fields of hand held magnets.

Magnetic nanoparticles are a class of nanoparticle which consist of magnetic elements such as iron, nickel and cobalt and their chemical compounds and can be manipulated using a magnetic field. A number of different approaches to preparing such particles have been described. Lu et al., *Angew. Chem. Int. Ed. Engl.*, 2007, 46, 1222-1244.

Magnetic nanoparticles are typically smaller than 1 μm in diameter (typically 5-500 nm), while larger microbeads can be, e.g., from 0.5-500 μm in diameter. In many of the applications of magnetic nanoparticles, the particles perform best when the size of the nanoparticles is below a critical value, which is dependent on the material but is typically around 10-20 nm, when each nanoparticle becomes a single magnetic domain and shows superparamagnetic behavior when the temperature is above a particular temperature (a blocking temperature). In a supermagnetic state, nanoparticles are sufficiently small that their magnetization can randomly flip direction so that in the absence of a magnetic field the average magnetization can appear to be zero. An external magnetic field can magnetize the nanoparticles, similarly to a paramagnet. However, the magnetic susceptibility of supermagnetic nanoparticles is much greater than that of paramagnet.

Magnetic nanoparticles have been studied, in particular, for potential biomedical applications, including magnetic resonance imaging contrast enhancement, tissue repair, immunoassay, detoxification of biological fluids, hyperthermia, drug delivery and in cell separation. Gupta et al., *Biomaterials,* 2005, 26(18), 3995-4021.

SUMMARY

The present disclosure provides a method for the magnetic labeling of a bacterial cell. The method includes contacting the cell with an affinity ligand of the formula (I):

T-L-A (I)

wherein:

T is a targeting ligand that binds or reacts selectively with a component of the bacterial cell;

A is a chemical moiety comprising a first bioorthogonally reactive group; and

L is bond or a linking group attaching A to T;

and subsequently contacting the cell with a magnetic agent of the formula (II):

B-M (II)

wherein:

M is a magnetic particle; and

B is a chemical moiety comprising a second bioorthogonally reactive group that is covalently attached to the magnetic particle;

wherein the first and second bioorthogonally reactive groups are complementary and can react with each other to form at least one covalent bond; and wherein the contacting with the magnetic agent is carried out under conditions sufficient for the first and second bioorthogonally reactive groups to react to form at least one covalent bond linking A and B.

The present disclosure also provides a kit for the magnetic labeling of a bacterial cell. The kit includes an affinity ligand of the formula (I):

T-L-A (I)

wherein:

T is a targeting ligand that binds or reacts selectively with a component of the bacterial cell;

A is a chemical moiety comprising a first bioorthogonally reactive group;

L is bond or a linking group attaching A to T.

The kit also includes magnetic agent of the formula (II):

B-M (II)

wherein:

M is a magnetic particle;

B is a chemical moiety comprising a second bioorthogonally reactive group that is covalently attached to the magnetic particle; and wherein the first and second bioorthogonally reactive groups are complementary and can react with each other to form at least one covalent bond.

The present disclosure also provides an affinity ligand for bioorthogonal labeling of a bacterial cell, wherein the affinity ligand is a compound of the formula (I):

T-L-A (I)

wherein:

T is a targeting ligand that binds or reacts selectively with a component of the bacterial cell;

A is a chemical moiety comprising a bioorthogonally reactive group; and

L is bond or a linking group attaching A to T.

The affinity ligand can be a compound of the following formula (III):

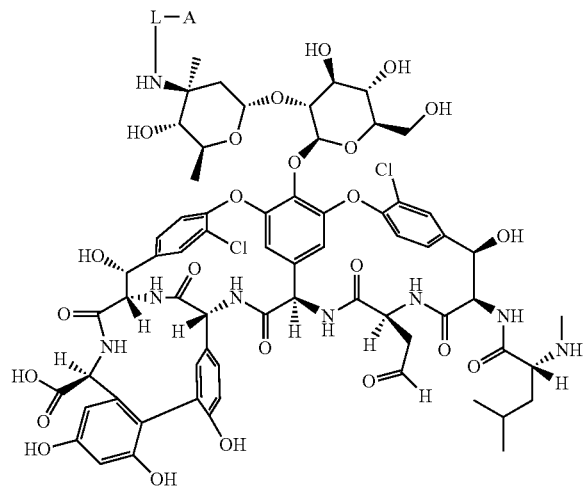

(III)

wherein:

A is a chemical moiety comprising a bioorthogonally reactive group; and

L is bond or a linking group.

The affinity ligand can be, e.g., a compound of the following formula:

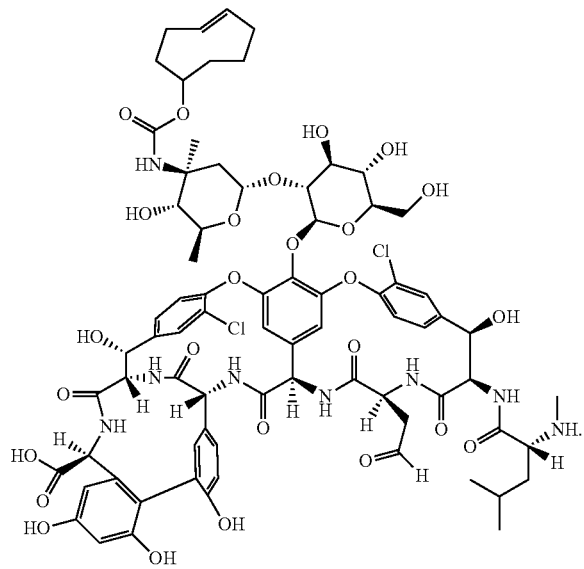

The affinity ligand can be a compound of the following formula (IV):

(IV)
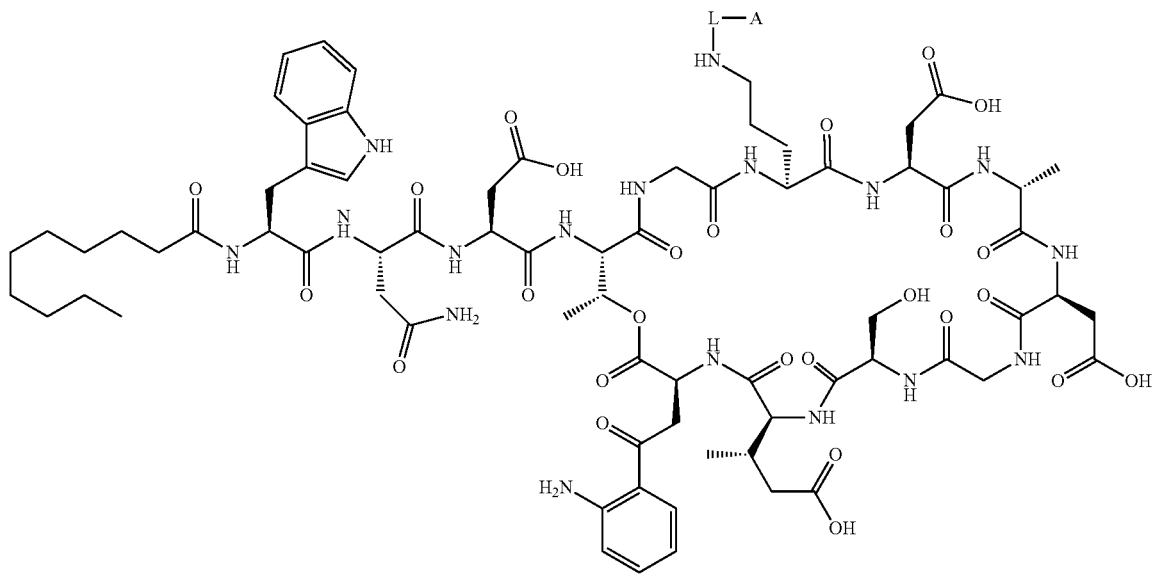
wherein:
A is a chemical moiety comprising a bioorthogonally reactive group; and
L is bond or a linking group.
The affinity ligand can be, e.g., a compound of the following formula:
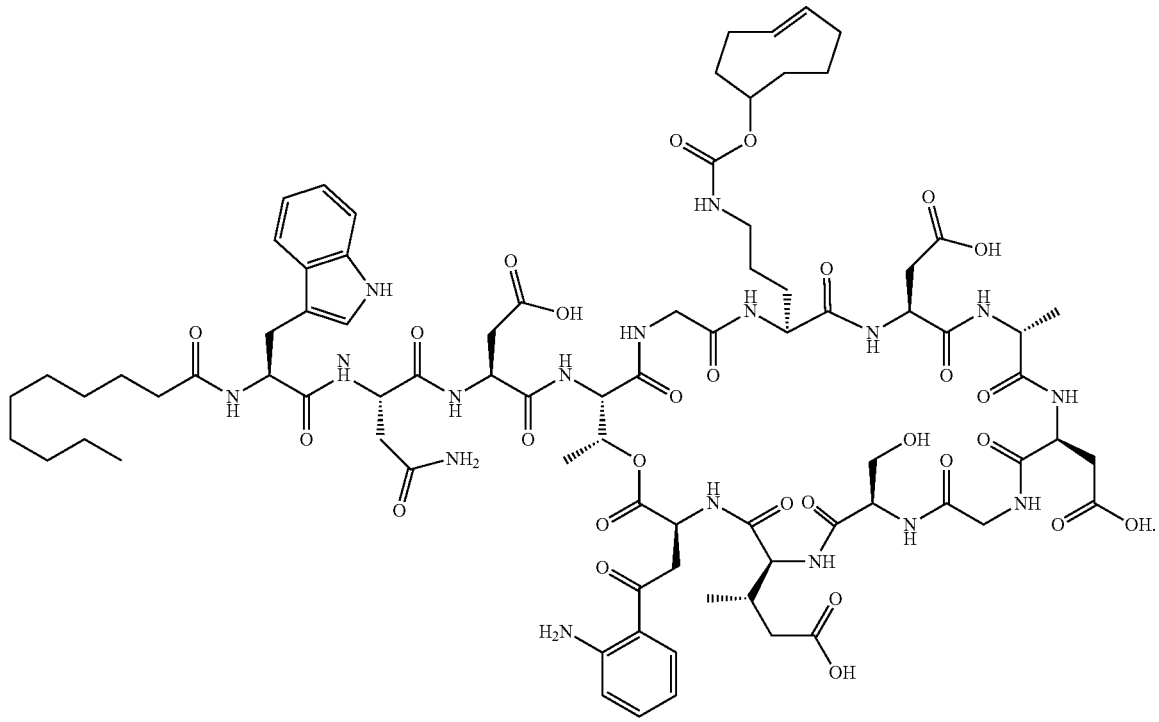 [SMILES: CCCCCCCCCC(=O)N[C@@H](Cc1c[nH]c2ccccc12)C(=O)N[C@@H](CC(N)=O)C(=O)N[C@@H](CC(=O)O)C(=O)N[C@@H]1C(=O)NCC(=O)N[C@@H](CCCNC(=O)OC2CC/C=C/CCC2)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@@H](C)CC(=O)O)C(=O)N[C@@H](CC(=O)c2ccccc2N)C(=O)O[C@@H]1C]
The affinity ligand can be a compound of the following formula (V):

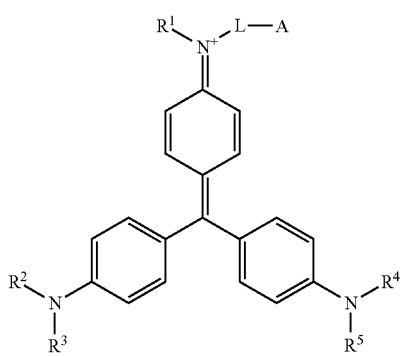

(V)

wherein:
R¹ is hydrogen or $(C_1-C_6)$alkyl;
R² is $(C_1-C_6)$alkyl;
R³ is $(C_1-C_6)$alkyl;
R⁴ is $(C_1-C_6)$alkyl;
R⁵ is $(C_1-C_6)$alkyl;
A is a chemical moiety comprising a bioorthogonally reactive group; and
L is bond or a linking group.

The affinity ligand can be, e.g., a compound of the following formula:

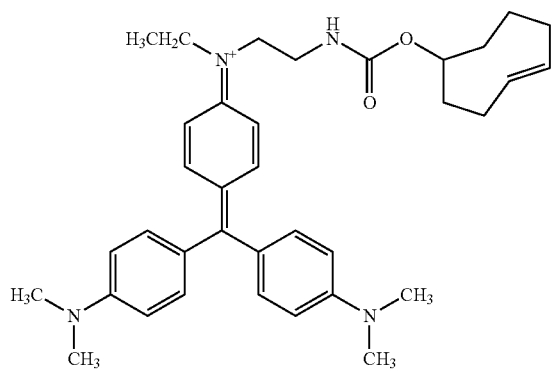

The affinity ligand can be a compound of the following formula (VI):

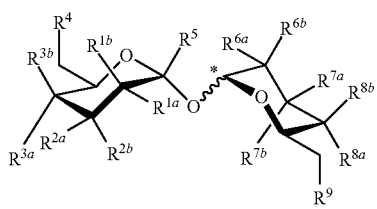

(VI)

wherein:
one of $R^{1a}$ and $R^{1b}$ is —H and the other is selected from —OH, —O-L-A, —NH₂, —NH-L-A, and halogen;
one of $R^{2a}$ and $R^{2b}$ is —H and the other is selected from —OH, —O-L-A, —NH₂, —NH-L-A, and halogen;
one of $R^{3a}$ and $R^{3b}$ is —H and the other is selected from —OH, —O-L-A, —NH₂, —NH-L-A, and halogen;
R⁴ is selected from —H, —OH, —O-L-A, —NH₂, —NH-L-A, and halogen;

R⁵ is selected from —H and $(C_1-C_6)$alkyl;
one of $R^{6a}$ and $R^{6b}$ is —H and the other is selected from —OH, —O-L-A, —NH₂, —NH-L-A, and halogen;
one of $R^{7a}$ and $R^{7b}$ is —H and the other is selected from —OH, —O-L-A, —NH₂, —NH-L-A, and halogen;
one of $R^{8a}$ and $R^{8b}$ is —H and the other is selected from —OH, —O-L-A, —NH₂, —NH-L-A, and halogen;
R⁹ is selected from —H, —OH, —O-L-A, —NH₂, —NH-L-A, and halogen;
the stereochemistry of the glycoside link at C* is α or β;
A is a chemical moiety comprising a bioorthogonally reactive group; and
L is bond or a linking group;
provided that:
one and only one of $R^{1a}$, $R^{1b}$, $R^{2a}$, $R^{2b}$, $R^{3a}$, $R^{3b}$, $R^4$, $R^{6a}$, $R^{6b}$, $R^{7a}$, $R^{7b}$, $R^{8a}$, $R^{8b}$ and $R^9$ is —O-L-A or —NH-L-A;
no more than three of $R^{1a}$, $R^{1b}$, $R^{2a}$, $R^{2b}$, $R^{3a}$, $R^{3b}$, $R^4$, $R^5$, $R^{6a}$, $R^{6b}$, $R^{7a}$, $R^{7b}$, $R^{8a}$, $R^{8b}$ and $R^9$ are other than —H or —OH; and
no more than two of $R^{1b}$, $R^{2b}$, $R^{3b}$, $R^{6b}$, $R^{7b}$ and $R^{8b}$ are other than —H.

The affinity ligand can be, e.g., a compound of the following formula:

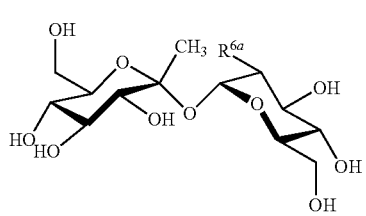

(VIA)

wherein $R^{6a}$ is a group according to one of the following formulae:

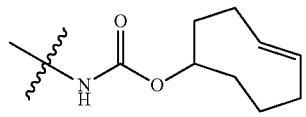

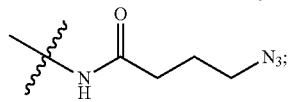

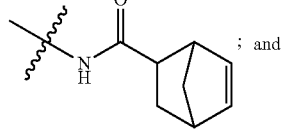

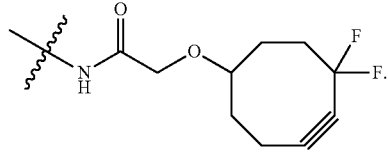

The affinity ligand can be, e.g., a compound of the following formula:

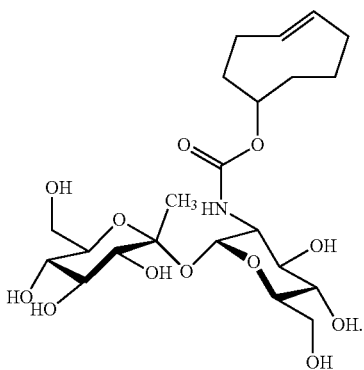

The details of one or more embodiments of the invention are set forth in the accompanying drawings and the description below. Other features, objects, and advantages of the invention will be apparent from the description and drawings, and from the claims.

DETAILED DESCRIPTION

Figure 1:
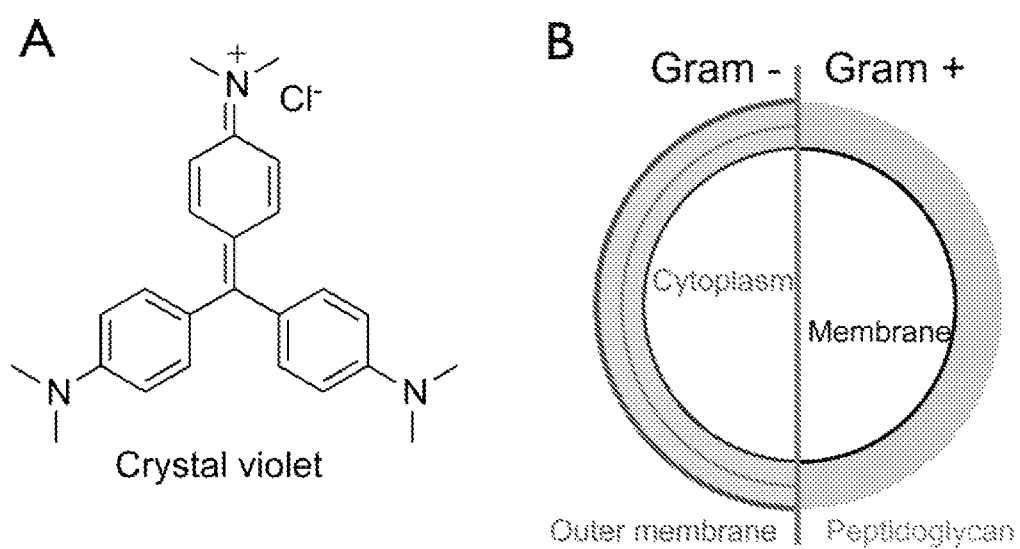
FIG. 1 shows (A) the chemical structure of crystal violet and (B) the composition of Gram-positive and Gram-negative cell wall.

The present disclosure provides methods of labeling bacteria with magnetic nanoparticles.

In the present description, it is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable sub-combination.

Although methods and materials similar or equivalent to those described herein can be used in the practice or testing of the present invention, suitable methods and materials are described below. In addition, the materials, methods and examples are illustrative only and not intended to be limiting.

I. Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

As used herein, "alkyl" refers to a saturated hydrocarbon chain that may be a straight chain or a branched chain. An alkyl group formally corresponds to an alkane with one C—H bond replaced by the point of attachment of the alkyl group to the remainder of the compound. The term "$(C_x\text{-}C_y)$alkyl" (wherein x and y are integers) by itself or as part of another substituent means, unless otherwise stated, an alkyl group containing from x to y carbon atoms. For example, a $(C_1\text{-}C_6)$alkyl group may have from one to six (inclusive) carbon atoms in it. Examples of $(C_1\text{-}C_6)$alkyl groups include, but are not limited to, methyl, ethyl, n-propyl, n-butyl, n-pentyl, n-hexyl, isopropyl, isobutyl, sec-butyl, tert-butyl, isopentyl, neopentyl and isohexyl. The $(C_x\text{-}C_y)$alkyl groups include $(C_1\text{-}C_{10})$alkyl, $(C_1\text{-}C_6)$alkyl, $(C_1\text{-}C_4)$alkyl and $(C_1\text{-}C_3)$alkyl.

The term "$(C_x\text{-}C_y)$alkylene" (wherein x and y are integers) refers to an alkylene group containing from x to y carbon atoms. An alkylene group formally corresponds to an alkane with two C—H bonds replaced by points of attachment of the alkylene group to the remainder of the compound. Examples are divalent straight hydrocarbon groups consisting of methylene groups, such as, —$CH_2$—, —$CH_2CH_2$—, —$CH_2CH_2CH_2$—. The $(C_x\text{-}C_y)$alkylene groups include $(C_1\text{-}C_6)$alkylene and $(C_1\text{-}C_3)$alkylene.

The term "$(C_x\text{-}C_y)$heteroalkylene" (wherein x and y are integers) refers to a heteroalkylene group containing from x to y carbon atoms. A heteroalkylene group corresponds to an alkylene group wherein one or more of the carbon atoms have been replaced by a heteroatom. The heteroatoms may be independently selected from the group consisting of O, N and S. A divalent heteroatom (e.g., O or S) replaces a methylene group of the alkylene —$CH_2$—, and a trivalent heteroatom (e.g., N) replaces a methine group. Examples are divalent straight hydrocarbon groups consisting of methylene groups, such as, —$CH_2$—, —$CH_2CH_2$—, —$CH_2CH_2CH_2$—. The $(C_x\text{-}C_y)$alkylene groups include $(C_1\text{-}C_6)$heteroalkylene and $(C_1\text{-}C_3)$heteroalkylene.

As used herein, "alkenyl" refers to an unsaturated hydrocarbon chain that includes a C=C double bond. An alkenyl group formally corresponds to an alkene with one C—H bond replaced by the point of attachment of the alkenyl group to the remainder of the compound. The term "$(C_x\text{-}C_y)$alkenyl" (wherein x and y are integers) denotes a radical containing x to y carbons, wherein at least one carbon-carbon double bond is present (therefore x must be at least 2). Some embodiments are 2 to 4 carbons, some embodiments are 2 to 3 carbons and some embodiments have 2 carbons. Alkenyl groups may include both E and Z stereoisomers. An alkenyl group can include more than one double bond. Examples of alkenyl groups include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl, and the like.

As used herein, "alkynyl" refers to an unsaturated hydrocarbon chain that includes a CC triple bond. An alkynyl group formally corresponds to an alkyne with one C—H bond replaced by the point of attachment of the alkyl group to the remainder of the compound. The term "$(C_x\text{-}C_y)$alkynyl" (wherein x and y are integers) denotes a radical containing x to y carbons, wherein at least one carbon-carbon triple bond is present (therefore x must be at least 2). Some embodiments are 2 to 4 carbons, some embodiments are 2 to 3 carbons and some embodiments have 2 carbons. Examples of an alkynyl include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

As used herein, "halo" or "halogen" refers to —F, —Cl, —Br and —I.

The term "haloalkyl" as used herein refers to an alkyl group in which one or more of the hydrogen atoms has been replaced by a halogen atom. The term "$(C_x\text{—}C_y)$haloalkyl" (wherein x and y are integers) by itself or as part of another substituent means, unless otherwise stated, an alkyl group containing from x to y carbon atoms. The alkyl may be substituted with one halogen up to fully substituted, e.g., as represented by the formula $C_nF_{2n+1}$, when more than one halogen is present they may be the same or different and selected from F, Cl, Br or I. Some embodiments are 1 to 3 carbons. Haloalkyl groups may be straight-chained or branched. Examples include fluoromethyl, difluoromethyl, trifluoromethyl, chlorodifluoromethyl, 2,2,2-trifluoroethyl, pentafluoroethyl and the like. The term "perfluoroalkyl" denotes the group of the formula —$C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "aromatic" refers to a carbocycle or heterocycle having one or more polyunsaturated rings having aromatic character (i.e., having (4n+2) delocalized π (pi) electrons where n is an integer).

As used herein, "aryl," employed alone or in combination with other terms, refers to an aromatic hydrocarbon group.

The aryl group may be composed of, e.g., monocyclic or bicyclic rings and may contain, e.g., from 6 to 12 carbons in the ring, such as phenyl, biphenyl and naphthyl. The term "($C_x$-$C_y$)aryl" (wherein x and y are integers) denotes an aryl group containing from x to y ring carbon atoms. Examples of a ($C_6$-$C_{14}$)aryl group include, but are not limited to, phenyl, α-naphthyl, β-naphthyl, biphenyl, anthryl, tetrahydronaphthyl, fluorenyl, indanyl, biphenylenyl and acenaphthyl. Examples of a $C_6$-$C_{10}$ aryl group include, but are not limited to, phenyl, α-naphthyl, β-naphthyl, biphenyl and tetrahydronaphthyl.

An aryl group can be unsubstituted or substituted. A substituted aryl group can be substituted with one or more groups, e.g., 1, 2 or 3 groups, including: ($C_1$-$C_6$)alkyl, ($C_2$-$C_6$)alkenyl, ($C_2$-$C_6$)alkynyl, halogen, ($C_1$-$C_6$)haloalkyl, —CN, —NO$_2$, —C(=O)R, —C(=O)OR, —C(=O)NR$_2$, —C(=NR)NR$_2$, —NR$_2$, —NRC(=O)R, —NRC(=O)O($C_1$-$C_6$)alkyl, —NRC(=O)NR$_2$, —NRC(=NR)NR$_2$, —NRSO$_2$R, —OR, —O($C_1$-$C_6$)haloalkyl, —OC(=O)R, —OC(=O)O($C_1$-$C_6$)alkyl, —OC(=O)NR$_2$, —SR, —S(O)R, —SO$_2$R, —OSO$_2$($C_1$-$C_6$)alkyl, —SO$_2$NR$_2$, —($C_1$-$C_6$)alkylene-CN, —($C_1$-$C_6$)alkylene-C(=O)OR, —($C_1$-$C_6$)alkylene-C(=O)NR$_2$, —($C_1$-$C_6$)alkylene-OR, —($C_1$-$C_6$)alkylene-OC(=O)R, —($C_1$-$C_6$)alkylene-NR$_2$, —($C_1$-$C_6$)alkylene-NRC(=O)R, —NR($C_1$-$C_6$)alkylene-C(=O)OR, —NR($C_1$-$C_6$)alkylene-C(=O)NR$_2$, —NR($C_2$-$C_6$)alkylene-OR, —NR($C_2$-$C_6$)alkylene-OC(=O)R, —NR($C_2$-$C_6$)alkylene-NR$_2$, —NR($C_2$-$C_6$)alkylene-NRC(=O)R, —O($C_1$-$C_6$)alkylene-C(=O)OR, —O($C_1$-$C_6$)alkylene-C(=O)NR$_2$, —O($C_2$-$C_6$)alkylene-OR, —O($C_2$-$C_6$)alkylene-OC(=O)R, —O($C_2$-$C_6$)alkylene-NR$_2$ and —O($C_2$-$C_6$)alkylene-NRC(=O)R, wherein each R group is hydrogen or ($C_1$-$C_6$ alkyl).

The term "heteroaryl" or "heteroaromatic" as used herein refers to an aromatic ring system having at least one heteroatom in at least one ring, and from 2 to 9 carbon atoms in the ring system. The heteroaryl group has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaryls include furyl, thienyl, pyridyl, oxazolyl, pyrrolyl, indolyl, quinolinyl or isoquinolinyl, and the like. The heteroatoms of the heteroaryl ring system can include heteroatoms selected from one or more of nitrogen, oxygen and sulfur.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,5-naphthyridinyl, 1,8-naphthyridinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6- and 7-benzothienyl, benzoxazolyl, benzthiazolyl, particularly 2-benzothiazolyl and 5-benzothiazolyl, purinyl, benzimidazolyl, particularly 2-benzimidazolyl and benztriazolyl.

A heteroaryl group can be unsubstituted or substituted. A substituted heteroaryl group can be substituted with one or more groups, e.g., 1, 2 or 3 groups, including: ($C_1$-$C_6$)alkyl, ($C_2$-$C_6$)alkenyl, ($C_2$-$C_6$)alkynyl, halogen, ($C_1$-$C_6$)haloalkyl, —CN, —NO$_2$, —C(=O)R, —C(=O)OR, —C(=O)NR$_2$, —C(=NR)NR$_2$, —NR$_2$, —NRC(=O)R, —NRC(=O)O($C_1$-$C_6$)alkyl, —NRC(=O)NR$_2$, —NRC(=NR)NR$_2$, —NRSO$_2$R, —OR, —O($C_1$-$C_6$)haloalkyl, —OC(=O)R, —OC(=O)O($C_1$-$C_6$)alkyl, —OC(=O)NR$_2$, —SR, —S(O)R, —SO$_2$R, —OSO$_2$($C_1$-$C_6$)alkyl, —SO$_2$NR$_2$, —($C_1$-$C_6$)alkylene-CN, —($C_1$-$C_6$)alkylene-C(=O)OR, —($C_1$-$C_6$)alkylene-C(=O)NR$_2$, —($C_1$-$C_6$)alkylene-OR, —($C_1$-$C_6$)alkylene-OC(=O)R, —($C_1$-$C_6$)alkylene-NR$_2$, —($C_1$-$C_6$)alkylene-NRC(=O)R, —NR($C_1$-$C_6$)alkylene-C(=O)OR, —NR($C_1$-$C_6$)alkylene-C(=O)NR$_2$, —NR($C_2$-$C_6$)alkylene-OR, —NR($C_2$-$C_6$)alkylene-OC(=O)R, —NR($C_2$-$C_6$)alkylene-NR$_2$, —NR($C_2$-$C_6$)alkylene-NRC(=O)R, —O($C_2$-$C_6$)alkylene-C(=O)OR, —O($C_1$-$C_6$)alkylene-C(=O)NR$_2$, —O($C_2$-$C_6$)alkylene-OR, —O($C_2$-$C_6$)alkylene-OC(=O)R, —O($C_2$-$C_6$)alkylene-NR$_2$ and —O($C_2$-$C_6$)alkylene-NRC(=O)R, wherein each R group is hydrogen or ($C_1$-$C_6$ alkyl).

The aforementioned listing of heteroaryl moieties is intended to be representative and not limiting.

The term "substituted" means that an atom or group of atoms formally replaces hydrogen as a "substituent" attached to another group. The term "substituted", unless otherwise indicated, refers to any level of substitution, namely mono-, di-, tri-, tetra- or penta-substitution, where such substitution is permitted. The substituents are independently selected, and substitution may be at any chemically accessible position. When groups are described herein as being substituted, the substituents can include, but are not limited to, ($C_1$-$C_6$)alkyl, ($C_2$-$C_6$)alkenyl, ($C_2$-$C_6$)alkynyl, halogen, ($C_1$-$C_6$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —(($C_1$-$C_6$)alkylene)Ar, —O(($C_1$-$C_6$)alkylene)Ar, —OC(=O)($C_1$-$C_6$)alkyl, —OC(=O)O($C_1$-$C_6$)alkyl, —OC(=O)NR$_2$, —NR$_2$, —NRAr, —NR(($C_1$-$C_6$)alkylene)Ar, —NRC(=O)R, —NRC(=O)Ar, —NRC(=O)O($C_1$-$C_6$)alkyl, —NRC(=O)NR$_2$, —NRSO$_2$R, —SR, —S(O)R, —SO$_2$R, —OSO$_2$($C_1$-$C_6$)alkyl, —SO$_2$NR$_2$, ($C_1$-$C_8$)perfluoroalkyl, —($C_2$-$C_6$)alkylene-OR, —O($C_2$-$C_6$)alkylene-N(($C_1$-$C_6$)alkyl)$_2$, —P(=O)(OR)$_2$, —OP(=O)(OR)$_2$, oxo, or sulfido, wherein each R group is hydrogen or ($C_1$-$C_6$ alkyl), e.g., methyl and wherein each Ar is independently unsubstituted aryl or heteroaryl or aryl or heteroaryl substituted with one or more of ($C_1$-$C_6$) alkyl, ($C_2$-$C_6$)alkenyl, ($C_2$-$C_6$)alkynyl, halogen, ($C_1$-$C_6$)haloalkyl, —CN, —NO$_2$, —C(=O)R, —C(=O)OR, —C(=O)NR$_2$, —C(=NR)NR$_2$, —OR, —OC(=O)($C_1$-$C_6$)alkyl, —OC(=O)O($C_1$-$C_6$)alkyl, —OC(=O)NR$_2$, —NR$_2$, —NRC(=O)R, —NRC(=O)O($C_1$-$C_6$)alkyl, —NRC(=O)NR$_2$, —NRSO$_2$R, —SR, —S(O)R, —SO$_2$R, —OSO$_2$($C_1$-$C_6$)alkyl, —SO$_2$NR$_2$, ($C_1$-$C_8$)perfluoroalkyl, —($C_2$-$C_6$)alkylene-OR, —O($C_2$-$C_6$)alkylene-N(($C_1$-$C_6$)alkyl)$_2$, —P(=O)(OR)$_2$, —OP(=O)(OR)$_2$ wherein each R group is hydrogen or ($C_1$-$C_6$ alkyl).

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to, chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluormethansulfonate, ethanesulfonate, benzenesulfonate, p-toluenesulfonate, p-trifluoromethylbenzenesulfonate, hydroxide, aluminates and borates. Exemplary cations include, but are not limited to, monovalent alkali metal cations, such as lithium, sodium, potassium and cesium, and divalent alkaline earth metals, such as beryllium, magnesium, calcium, strontium and barium. Also included are transition metal cations, such as gold, silver, copper and zinc, as well as non-metal cations, such as ammonium salts.

References to the compounds described and disclosed herein are considered to include both the free base and all addition salts. The addition salts may be either salts with pharmaceutically acceptable cations such as $Na^+$, $Ca^{2+}$, $K^+$ or $Na^+$ at a terminal acid group, such as when the C-terminal amino acid is Gly or OH is present, or with a pharmaceutically acceptable acid addition salt at a basic center of the peptide, such as in an Arg unit. The acetate salt forms are useful, and hydrochloride, hydrobromide and salts with other strong acids are also useful. In the isolation procedures outlined in the Examples, the peptide product is often isolated and purified as an acetate salt. The compounds may also form inner salts or zwitterions when a free terminal carboxy group is present. The term "pharmaceutically-acceptable salt" refers to salts that possess toxicity profiles within a range that affords utility in pharmaceutical applications. Pharmaceutically unacceptable salts may nonetheless possess properties such as high crystallinity, which may render them useful, e.g., in processes of synthesis, purification or formulation of compounds described herein. In general the useful properties of the compounds described herein do not depend on whether the compound is or is not in a salt form, so unless clearly indicated otherwise (such as specifying that the compound should be in "free base" or "free acid" form), reference in the specification to a compound should be understood as including salt forms of the compound, whether or not this is explicitly stated. Preparation and selection of suitable salt forms is described in Stahl, et al., *Handbook of Pharmaceutical Salts: Properties, Selection, and Use*, Wiley-VCH 2002.

When in the solid state, the compounds described herein and salts thereof may occur in various forms and may, e.g., take the form of solvates, including hydrates. In general, the useful properties of the compounds described herein do not depend on whether the compound or salt thereof is or is in a particular solid state form, such as a polymorph or solvate, so unless clearly indicated otherwise reference in the specification to compounds and salts should be understood as encompassing any solid state form of the compound, whether or not this is explicitly stated.

Compounds provided herein can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

"Selectively binds to" or "selectively reacts with" means that one molecule, such as a targeting ligand preferentially binds to or reacts with another molecule, such as a target molecule, e.g., a nucleic acid or a protein, in the presence of other molecules in a sample.

The following abbreviations may also be found herein: Boc (t-butoxycarbonyl); $CHCl_3$ (chloroform); $CuSO_4$ (copper sulfate); DCM (dichloromethane); DIPEA (N,N-diisopropylethylamine; DME (1,2-dimethoxyethane); DMF (N,N-dimethylformamide); EDC (N-ethyl-N'-(3-dimethylaminopropyl)carbodiimide); Et (ethyl); EtOAc (ethyl acetate); eq. (equivalent(s)); Fmoc (9-fluorenylmethylmethoxycarbonyl); h (hour(s)); HOBt (N-hydroxybenzotriazole); HPLC (high-performance liquid chromatography); LC (liquid chromatography); MeOH (methanol); $MgSO_4$ (magnesium sulfate); min (minute(s)); MS (mass spectrometry); $NaHCO_3$ (sodium bicarbonate); NaOH (sodium hydroxide); $Na_2SO_3$ (sodium sulfite); $NH_4Cl$ (ammonium chloride); NMO (N-methyolmorpholine-N-oxide); Pbf (2,2,4,6,7-pentamethyldihydrobenzofuran-5-sulfonyl); t-Bu (tenbutyl); TCO (trans-cyclooctene); TEAP (triethylammonium phosphate); TFA (trifluororacetic acid); TFE (2,2,2-trifluoroethanol); THF (tetrahydrofuran); TMSOTf (trimethylsilyl trifluoromethanesulfonate); TIS (triisopropylsilane); TPAP (tetrapropylammonium perrhuthenate); TPP (triphenylphosphine); and Trt (trityl [triphenylmethyl, $(C_6H_5)_3C$—]); Tz (1,2,4,5-tetrazine).

II. Labeling Methods

The present disclosure provides a method for the magnetic labeling of a bacterial cell. The method includes contacting the cell with an affinity ligand of the formula (I):

T-L-A                               (I)

wherein:
T is a targeting ligand that binds or reacts selectively with a component of the bacterial cell;
A is a chemical moiety comprising a first bioorthogonally reactive group; and
L is a bond or a linking group attaching A to T;
and subsequently contacting the cell with a magnetic agent of the formula (II):

B-M                                 (II)

wherein:
M is a magnetic particle; and
B is a chemical moiety comprising a second bioorthogonally reactive group that is covalently attached to the magnetic particle;
wherein the first and second bioorthogonally reactive groups are complementary and can react with each other to form at least one covalent bond; and
wherein the contacting with the magnetic agent is carried out under conditions sufficient for the first and second bioorthogonally reactive groups to react to form at least one covalent bond linking A and B.

A. Bacterial Cells

The bacterial cells that can be labeled using the methods described herein include any bacterial cell for which there is a targeting ligand that can bind or react selectively with a component of the bacterial cell, e.g., the bacterial cell wall, or a component thereof. The bacterial cells that can be labeled include, e.g., pathogenic bacteria.

Examples of bacteria that can be labeled include members of bacterial genera such as *Bacillus, Bacteroides, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio* and *Yersinia*.

Examples of bacterial species that can be labeled include *Bacillus anthracis, Bordetella pertussis, Borrelia burgdorferi, Brucella aborus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium bovis, Mycobacterium leprae, Mycobacterium tuberculosis, Mycoplasma pneumoniae, Neisseria gonorrhoeae, Neisseria meningitidis, Nocardia asteroids, Nocardia brasiliensis, Nocardia farcinica, Pseudomonas aeruginosa, Rickettsia rickettsii, Salmonella typhi, Salmonella typhimurium, Shigella sonnei, Staphylococcus aureus, Staphylococcus epidermis, Staphylococcus saprophyticus, Streptococcus agalactiae, Streptococcus pneumoniae, Streptococcus pyogenes, Treponema pallidum, Vibrio cholerae*, and *Yersinia pestis*.

In some embodiments, the bacteria that can be labeled are Gram-positive bacteria. Examples of Gram-positive bacteria that can be labeled include bacteria of the following genera: *Bacillus, Clostridium, Corynebacterium, Enterococcus, Listeria, Staphylococcus* and *Streptococcus*. Examples of Gram-positive bacteria include: *Bacillus anthracis, Clostridium botulinum, Clostridium difficile, Clostridium perfringens, Clostridium tetani, Corynebacterium diphtheriae, Enterococcus faecalis, Enterococcus faecium, Listeria monocytogenes, Staphylococcus aureus, Staphylococcus epidermis, Staphylococcus saprophyticus, Streptococcus agalactiae, Streptococcus pneumoniae*, and *Streptococcus pyogenes*.

In some embodiments, the bacteria that can be labeled are Gram-negative bacteria. Examples of Gram-negative bacteria that can be labeled include bacteria of the following genera: *Bacteroides, Bordetella, Borrelia, Brucella, Campylobacter, Escherichia, Francisella, Haemophilus, Helicobacter, Legionella, Leptospira, Neisseria, Pseudomonas, Rickettsia, Salmonella, Shigella, Treponema, Vibrio* and *Yersinia*. Examples of Gram-negative bacteria include: *Bordetella pertussis, Borrelia burgdorferi, Brucella aborus, Brucella canis, Brucella melitensis, Brucella suis, Campylobacter jejuni, Escherichia coli, Francisella tularensis, Haemophilus influenzae, Helicobacter pylori, Legionella pneumophila, Leptospira interrogans, Neisseria gonorrhoeae, Neisseria meningitidis, Pseudomonas aeruginosa, Rickettsia rickettsii, Salmonella typhi, Salmonella typhimurium, Shigella sonnei, Treponema pallidum, Vibrio cholerae*, and *Yersinia pestis*.

In some embodiments, the bacteria that can be labeled include trehalose in their cell walls. Examples of such bacteria include bacteria of the following genera: *Corynebacteria, Mycobacterium*, and *Nocardia*. Examples of such bacteria include *Corynebacterium diphtheriae, Mycobacterium bovis, Mycobacterium leprae, Mycobacterium tuberculosis, Nocardia asteroides* and *Nocardia brasiliensis*.

B. Bioorthogonally Reactive Groups

The labeling method described herein involves a two-step procedure wherein the bacterial cell to be labeled is first contacted with an affinity ligand, T-L-A (I), which includes a targeting ligand T that binds or reacts selectively with a component of the bacterial cell, followed by contacting with a magnetic agent, B-M (II), which includes the magnetic particle. The labeling is achieved through the reaction of complementary bioorthogonally reactive groups present on the affinity ligand and the magnetic agent, A and B, which can react with each other to form at least one covalent bond. Although in principle labeling of bacteria might be carried out directly, using a ligand attached to a magnetic particle, it has surprisingly been found that the bioorthogonal method described herein can achieve significantly higher sensitivity in labeling and detection.

The term "bioorthogonally reactive groups" refers to chemically reactive groups that can react with each other in the presence of biological molecules, which allows chemical reactions to be performed within or in the presence of living systems. Bioorthogonal chemistry can therefore be used to study living systems. See, e.g., Baskin et al., *Proc. Natl. Acad. Sci. USA*, 2007, 104, 16793-16797; Best, *Biochemistry*, 2009, 48(28), pp. 6571-6584; Chen et al., *Acc. Chem. Res.*, 2011, 44(9), 762-773; Dimandis et al., *Clin. Chem.*, 1991, 37, 625-636; Kolb et al., *Angew. Chem. Int. Ed.*, 2001, 40, 2004-2021; Link et al., *Curr. Opin. Biotechnol*. 2003, 14, 603-609; Link et al., *J. Am. Chem. Soc.*, 2003, 125, 11164-11165; Prescher et al., *Nature*, 2004, 430(7002), 873-71; Prescher et al., *Nature Chemical Biology*, 2005, 1(1), 13-21; Lim et al., *Chem. Commun*. (Camb.), 2010, 46(10), 1589-600; Sletten et al., *Angew. Chem. Int. Ed.*, 2009, 48(38), 6974-6998; Wang et al., *J. Am. Chem. Soc.*, 2003, 12, 3192-3193. One type of reaction that has been used is the Staudinger ligation between phosphines and azides. Prescher et al., *Nature*, 2004, 430(7002), 873-877; Saxon et al., *Science*, 2000, 287(5460), 2007-10. Another useful reaction is the [3+2] cycloaddition "click" reaction between azides and alkynes. Rostovtsev et al., *Angew. Chem. Int. Ed.*, 2002, 41(14), 2596-2599. While this reaction proceeds in the presence of copper, a copper-free variant has been developed that does not require the use of copper, involving cycloaddition of azides to a strained alkyne such as a cyclooctyne ring, a dibenzocyclooctyne ring, an azadibenzocyclooctyne ring, or a bicyclononyne (e.g., bicycle[6.1.0]nonyne) ring. Agard et al., *J. Am. Chem. Soc.*, 2004, 126 (46), 15046-15047; Baskin et al., *Aldrichimica Acta*, 2010, 43(1), 15-23; Cenoweth et al., *Org. Biomol. Chem.*, 2009, 7, 5255-5258; Dommerholt et al., *Angew. Chem. Int. Ed.*, 2010, 49, 9422-9425; Jewett et al., *J. Am. Chem. Soc.*, 2010, 132 (11), 3688-3690; Marks et al., *Bioconjugate Chem.*, 2011, 22 (7), 1259-1263; Sletten et al., *Acc. Chem. Res.*, 2011, 44(9), 666-676.

The Diels-Alder reaction is a useful transformation that is known to proceed faster in water than in organic solvents due to the hydrophobic effect and which has been used in bioconjugation. Seelig et al., *Tetrahedron Lett.*, 1997, 38, 7729-7732; Yousaf et al., *J. Am. Chem. Soc.*, 1999, 121, 4286-4287. A particularly useful variant of the Diels-Alder reaction employs a fast bioorthogonal reaction based on the inverse-electron-demand Diels-Alder reaction between 1,2, 4,5-tetrazine and a suitable dienophile, particularly a trans-cyclooctene group or cyclooctyne group. Blackman et al., *J. Am. Chem. Soc.* 2008, 130, 13518-13519; US2009/0023916; US2011/0268654; US2012/0034161.

Any of the bioorthogonal groups described herein, or in the references cited herein, can be used in the practice of the methods described herein.

In some embodiments, A and B include bioorthogonally reactive groups that can react with each other via a [4+2] cycloaddition reaction, such as a Diels-Alder reaction. In some embodiments one of A and B can include a diene, or a precursor thereof, and the other includes a dienophile, or a precursor thereof, wherein A and B can react with each other via a Diels-Alder reaction. In some embodiments, one of A and B includes a 1,3-butadiene group (C=C—C=C) and the other of A and B includes an ethene group (C=C) or an ethyne group (C≡C) substituted with at least one electron-withdrawing group, e.g., =CN, —CO₂(C₁-C₆)alkyl, —CONH(C₁-C₆)alkyl; in some embodiments, the other of A and B can include a maleimide group. In some embodiments, one of A and B includes a 1,2,4,5-tetrazine group (Tz) and the other of A and B includes an ethene group (C=C) or an ethyne group (C≡C). In some embodiments, one of A and B includes a 1,2,4,5-tetrazine group and the other of A and B includes a trans-cyclooctene group. In some embodiments, one of A and B includes a 1,2,4,5-tetrazine group and the other of A and B includes a cyclooctyne group. Depending on the individual components, A and B, a [4+2] cycloaddition reaction can proceed at room temperature, or with heating.

In some embodiments, one of A and B comprises a trans-cyclooctene group, e.g., a trans-cyclooct-1-ene-5-yl group and the other of A and B comprises a 1,2,4,5-tetrazine group, e.g., a 1,2,4,5-tetrazine-3-yl group.

In some embodiments, A comprises a trans-cyclooctene group, e.g., a trans-cyclooct-1-ene-5-yl group and B comprises a 1,2,4,5-tetrazine group, e.g., a 1,2,4,5-tetrazine-3-yl group.

In some embodiments, A and B include bioorthogonally reactive groups that can react with each other via a 1,3-dipolar cycloaddition reaction. In some embodiments, one of A and B comprises an azide group, and the other of A and B comprises an ethyne (C≡C) group. The reaction can take place, e.g., in the presence of a copper catalyst. If a strained alkyne group is used, such as a cyclooctyne, e.g., a 3,3-difluorocyclooctyne group, a 3,3-difluorocyclooctyne-6-oxy group, or a dibenzocyclooctyne group; the reaction can take place in the absence of copper.

In some embodiments, A and B include bioorthogonally reactive groups that can react with each other via a Staudinger ligation reaction. In some embodiments, one of A and B comprises a phenyl group that is substituted with a phosphine group ortho to a carboxylic acid ester group and the other of A and B comprises an azide group.

C. Targeting Ligands

The targeting ligand T can be any molecule that binds or reacts selectively with a component of the bacterial cell. Binding or reacting selectively means that the targeting ligand preferentially binds to or reacts with the component of the bacterial cell, in the presence of other molecules in a sample. In some embodiments, the targeting ligand binds or reacts selectively with a cell wall component of the bacterial cell. In some embodiments, the targeting ligand binds or reacts selectively with a cell surface component of the bacterial cell. In some embodiments, in reacting selectively with a component of the bacterial cell, the targeting ligand is incorporated into a component of the cell, e.g., the cell wall.

In some embodiments, the targeting ligand comprises an antibody that binds selectively to a particular species of bacterium. Antibodies, e.g., monoclonal antibodies, against bacteria are commercially available or may be prepared by methods known in the art. In addition, methods of conjugating small molecules to antibodies are also known in the art and can be used to attach a suitable bioorthogonally reactive group, via a suitable linking group, to the antibody.

In some embodiments, the targeting ligand comprises an antibiotic. Antibiotics frequently exert their antibiotic effect by binding or reacting selectively with a component of the bacterial cell, e.g., a component of the cell wall.

In some embodiments, the targeting ligand comprises a glycopeptide antibiotic. Suitable glycopeptide antibiotics include, e.g., bleomycin, decaplanin, ramoplanin, teicoplanin, telavancin and vancomycin. In some embodiments, the targeting ligand is vancomycin.

In some embodiments, the affinity ligand is a compound of the following formula:

(III)

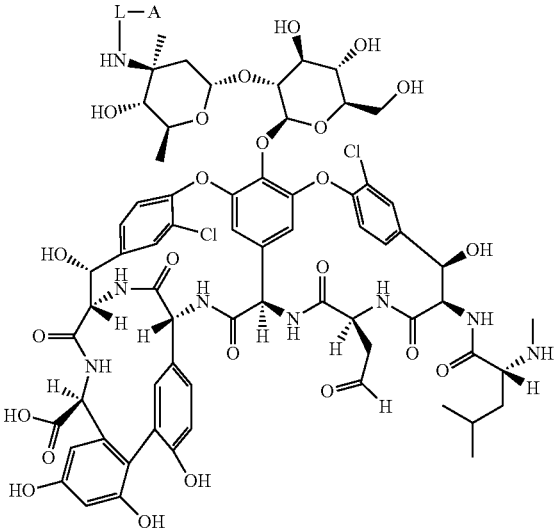

In some embodiments, the affinity ligand is a compound of the following formula:

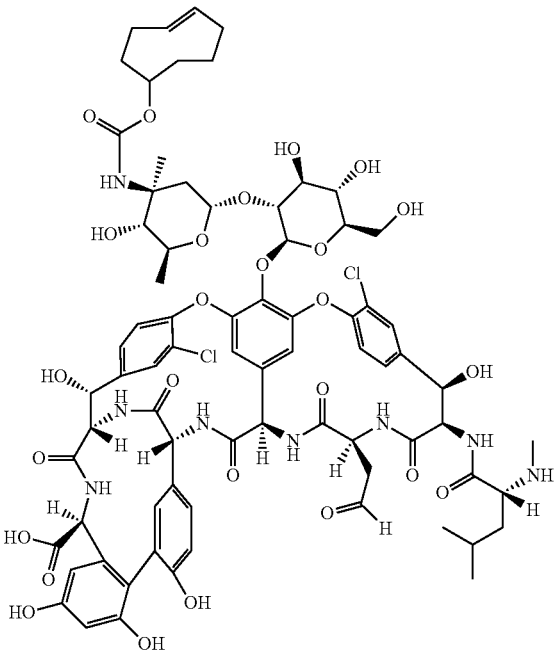

In some embodiments, the targeting ligand comprises a lipopeptide antibiotic. Suitable lipopeptide antibiotics include, e.g., amphomycin, aspartocin, brevistin, cerexin A, cerexin B, daptomycin, glumamycin, laspartomycin, tsushimycin and zaomycin. In some embodiments, the targeting ligand is daptomycin. In some embodiments, the targeting ligand is daptomycin.

In some embodiments, the affinity ligand is a compound of the following formula:

cephamycins, monobactams, oxacephems, penems and penicillins. Suitable carbacephems include, e.g., loracarbef. Suitable carbapenems include, e.g., biapenem, doripenem, ertapenem, imipenem, meropenem, panipenem, razupenem and tebipenem. Suitable cephalosporins include, e.g., cefacetrile, cefadroxil, cephalexin, cefaloglycin, cefalonium, cefaloridine, cefalotin, cefapirin, cefatrizine, cefaza-

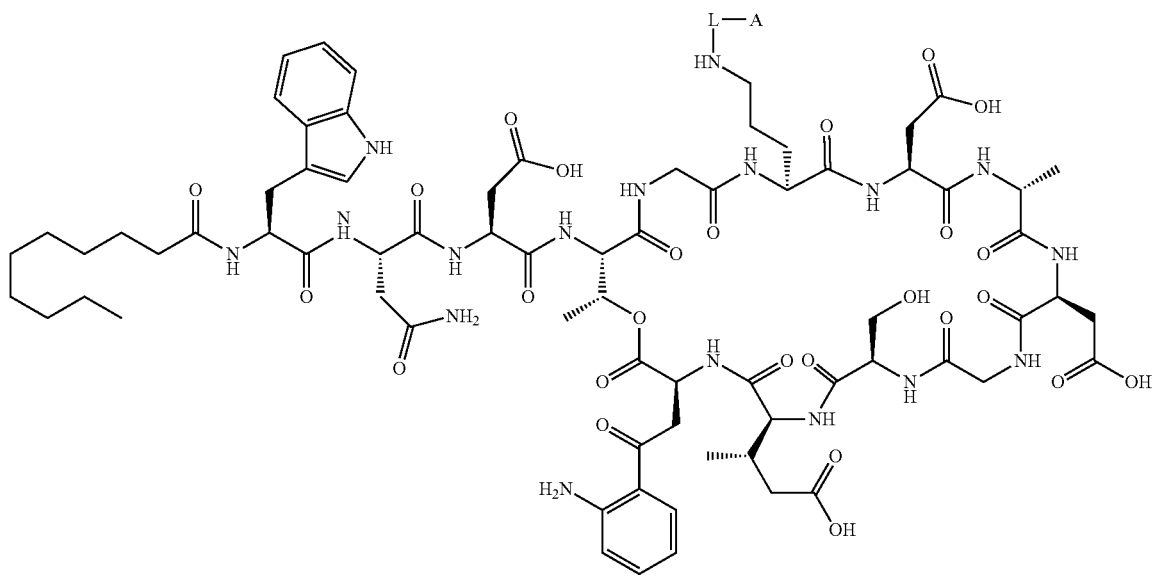

(IV)

In some embodiments, the affinity ligand is a compound of the following formula:

flur, cefazedone, cefazolin, cefradine, cefroxadine, ceftezole, cefaclor, cefonicid, cefprozil, cefuroxime, cefuzonam,

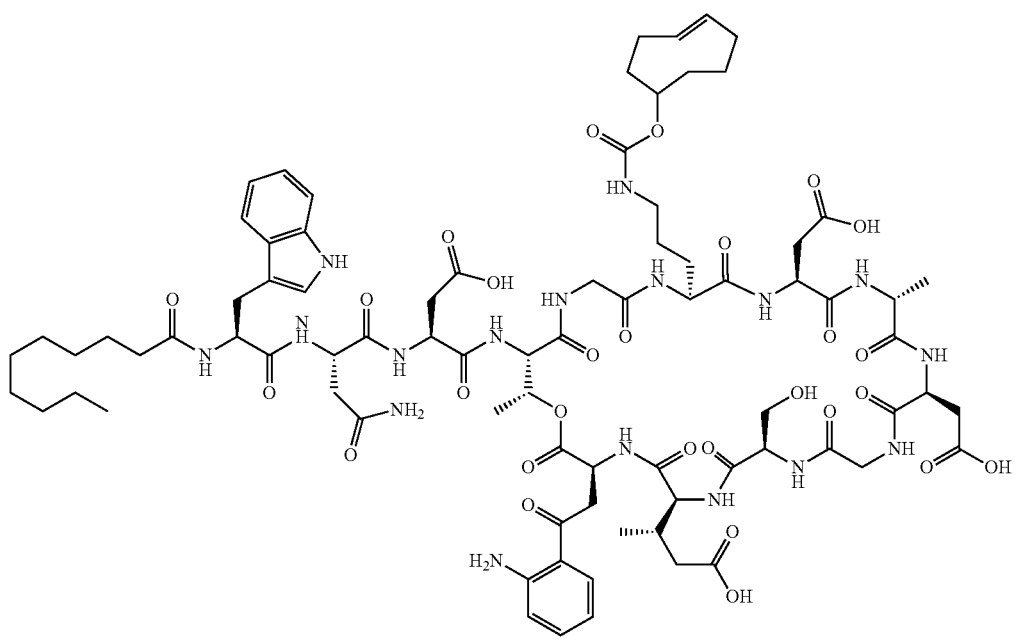 [SMILES: CCCCCCCCCC(=O)N[C@@H](Cc1c[nH]c2ccccc12)C(=O)N[C@@H](CC(N)=O)C(=O)N[C@@H](CC(=O)O)C(=O)N[C@@H]1C(=O)NCC(=O)N[C@@H](CCCNC(=O)OC2CC/C=C/CCC2)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@@H](C)CC(=O)O)C(=O)N[C@@H](CC(=O)c2ccccc2N)C(=O)O[C@@H]1C]

In some embodiments, the targeting ligand comprises a β-lactam antibiotic. Suitable β-lactam antibiotics can include, e.g., carbacephems, carbapenems, cephalosporins, cefinetazole, cefotetan, cefoxitin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, ceftobiprole and ceftaroline. Suitable cephamycins include, e.g., cefbuperazone, cefmetazole (Zefazone), cefminox, cefotetan (Cefotan), cefoxitin (Mefoxin) and flomoxef. Suitable monobactams include, e.g., aztreonam, nocardicin A, tabtoxin and tigemonam. Suitable oxacephems include, e.g., flomoxef and latamoxef. Suitable penems include, e.g., faropenem. Suitable penicillins include, e.g., benzylpenicillin, clometocillin, .benzathine benzylpenicillin, azidocillin, penamecillin, phenoxymethylpenicillin, propicillin, pheneticillin, cloxacillin, oxacillin, methicillin, nafcillin, amoxicillin, .ampicillin, epicillin, carbenicillin, ticarcillin temocillin, azlocillin, .piperacillin, mezlocillin, mecillinam, sulbenicillin, flucloxacillin and dicloxacillin.

In some embodiments, the targeting ligand comprises a polymyxin antibiotic. Suitable polymyxin antibiotics include, e.g., comprises polymyxin B, colistin, or polymyxin M.

The antibiotic targeting ligand can be linked to the bioorthogonally reactive group, via any suitable linking group attached at any substitutable position of the antibiotic molecule. The antibiotic molecule is modified by replacing a hydrogen atom of the antibiotic molecule with the group -L-A of the affinity ligand. The substitution can be carried out, e.g., by synthesizing an analog of the antibiotic with the group -L-A (or a precursor thereof) using a modification of a known synthetic route to the antibiotic, or by chemically modifying the antibiotic molecule to introduce the group -L-A (or a precursor thereof). The point of attachment of the group -L-A is selected based on synthetic convenience and based on the known structure activity relationships of the antibiotic molecule. It may be desirable, e.g., to introduce the -L-A group at a location that does not affect functional groups that are important to the binding of the antibiotic to its biological target. In addition, it may also be convenient to attach the -L-A group to a heteroatom (e.g., an accessible OH, NH, or SH group).

In some embodiments, the targeting ligand comprises a dye that binds or reacts selectively with the bacterial cell. Suitable dyes include those that are used for selectively staining bacteria. Examples of suitable dyes include, e.g., crystal violet (methyl violet 10B, Gentian violet), methyl violet 2B, safranin, carbolfuchsin, fuchsine, methylene blue, auramine O and rhodamine B.

In some embodiments, the affinity ligand is a compound of the following formula:

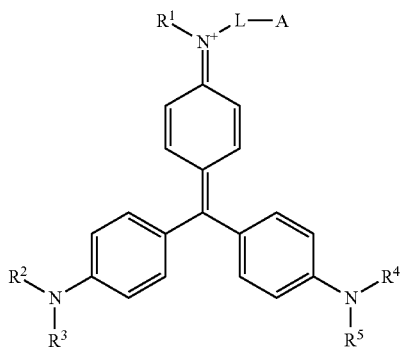

(V)

wherein:
$R^1$ is hydrogen or $(C_1-C_6)$alkyl, e.g., methyl or ethyl;
$R^2$ is $(C_1-C_6)$alkyl, e.g., methyl or ethyl;
$R^3$ is $(C_1-C_6)$alkyl, e.g., methyl or ethyl;
$R^4$ is $(C_1-C_6)$alkyl, e.g., methyl or ethyl; and
$R^5$ is $(C_1-C_6)$alkyl, e.g., methyl or ethyl.

In some embodiments of the compounds of formula (V), $R^1$ is hydrogen, methyl or ethyl. In some such embodiments, $R^1$ is ethyl.

In some embodiments of the compounds of formula (V), $R^2$ is methyl.

In some embodiments of the compounds of formula (V), $R^3$ is methyl.

In some embodiments of the compounds of formula (V), $R^4$ is methyl.

In some embodiments of the compounds of formula (V), $R^5$ is methyl.

In some embodiments of the compounds of formula (V), L-A is according to the following formula:

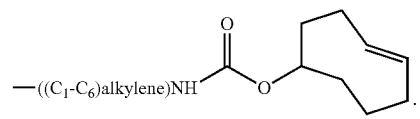

In some embodiments of the compounds of formula (V), L-A is according to the following formula:

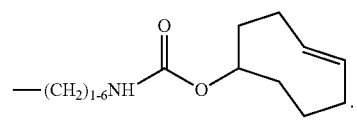

In some embodiments of the compounds of formula (V), L-A is according to the following formula:

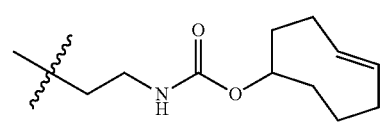

In some embodiment, the compound of formula (V) is according to the following formula:

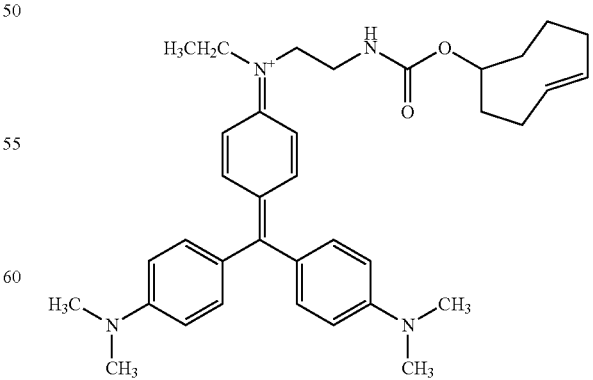

In some embodiments, the compound of formula (V) is used to label Gram-positive bacteria, e.g., by using a Gram staining method. In some embodiments, the compound of formula (V) is used to label Gram-negative bacteria. e.g., but using a Gram staining method. In some embodiments, the compounds of formula (V) can be used to distinguish Gram-positive and Gram-negative bacteria by applying or not applying the decolorization step of the Gram-staining method. The decolorization step removes the compound of formula (V) from Gram-negative bacteria, but the compound of formula (V) remains bound to Gram-positive bacteria.

In some embodiments, the affinity ligand is a compound of the following formula (VI):

(VI)

wherein:
one of $R^{1a}$ and $R^{1b}$ is —H and the other is selected from —OH, —O-L-A, —NH$_2$, —NH-L-A, and halogen;
one of $R^{2a}$ and $R^{2b}$ is —H and the other is selected from —OH, —O-L-A, —NH$_2$, —NH-L-A, and halogen;
one of $R^{3a}$ and $R^{3b}$ is —H and the other is selected from —OH, —O-L-A, —NH$_2$, —NH-L-A, and halogen;
$R^4$ is selected from —H, —OH, —O-L-A, —NH$_2$, —NH-L-A, and halogen;
$R^5$ is selected from —H and (C$_1$-C$_6$)alkyl;
one of $R^{6a}$ and $R^{6b}$ is —H and the other is selected from —OH, —O-L-A, —NH$_2$, —NH-L-A, and halogen;
one of $R^{7a}$, and $R^{7b}$ is —H and the other is selected from —OH, —O-L-A, —NH$_2$, —NH-L-A, and halogen;
one of $R^{8a}$ and $R^{8b}$ is —H and the other is selected from —OH, —O-L-A, —NH$_2$, —NH-L-A, and halogen;
$R^9$ is selected from —H, —OH, —O-L-A, —NH$_2$, —NH-L-A, and halogen;
the stereochemistry of the glycoside link at C* is α or β;
provided that:
one and only one of $R^{1a}$, $R^{1b}$, $R^{2a}$, $R^{2b}$, $R^{3a}$, $R^{3b}$, $R^4$, $R^{6a}$, $R^{6b}$, $R^{7a}$, $R^{7b}$, $R^{8a}$, $R^{8b}$ and $R^9$ is —O-L-A or —NH-L-A;
no more than three of $R^{1a}$, $R^{1b}$, $R^{2a}$, $R^{2b}$, $R^{3a}$, $R^{3b}$, $R^4$, $R^5$, $R^{6a}$, $R^{6b}$, $R^{7a}$, $R^{7b}$, $R^{8a}$, $R^{8b}$ and $R^9$ are other than —H or —OH; and
no more than two of $R^{1b}$, $R^{2b}$, $R^{3b}$, $R^{6b}$, $R^{7b}$ and $R^{8b}$ are other than H.

In some embodiments of the compounds of formula (VI), no more than two of $R^{1a}$, $R^{1b}$, $R^{2a}$, $R^{2b}$, $R^{3a}$, $R^{3b}$, $R^4$, $R^5$, $R^{6a}$, $R^{6b}$, $R^{7a}$, $R^{7b}$, $R^{8a}$, $R^{8b}$ and $R^9$ is other than —H or —OH.

In some embodiments of the compounds of formula (VI), no more than two of $R^{1a}$, $R^{1b}$, $R^{2a}$, $R^{2b}$, $R^{3a}$, $R^{3b}$, $R^4$, $R^5$, $R^{6a}$, $R^{6b}$, $R^{7a}$, $R^{7b}$, $R^{8a}$, $R^{8b}$ and $R^9$ is other than —H or —OH.

In some embodiments of the compounds of formula (VI), $R^{1a}$ is —OH and $R^{1b}$ is —H.

In some embodiments of the compounds of formula (VI), $R^{2a}$ is —OH and $R^{2b}$ is —H.

In some embodiments of the compounds of formula (VI), $R^{3a}$ is —OH and $R^{3b}$ is —H.

In some embodiments of the compounds of formula (VI), $R^4$ is —OH.

In some embodiments of the compounds of formula (VI), $R^5$ is —H or —CH$_3$. In some such embodiments, $R^5$ is —CH$_3$.

In some embodiments of the compounds of formula (VI), $R^{6a}$ is —O-L-A or —NH-L-A and $R^{6b}$ is —H. In some such embodiments, $R^{6a}$ is —NH-L-A. $R^{6a}$ may be a group according to one of the following formulae:

In some embodiments of the compounds of formula (VI), $R^{7a}$ is —OH and $R^{7b}$ is —H.

In some embodiments of the compounds of formula (VI), $R^{8a}$ is —OH and $R^{8b}$ is —H.

In some embodiments of the compounds of formula (VI), $R^9$ is —OH.

In some embodiments of the compounds of formula (VI), the stereochemistry of the glycoside link at C* is α.

In some embodiments of the compounds of formula (VI), the compound is according to the following formula (VIA):

(VIA)

wherein $R^{6a}$ is a group according to one of the following formulae:

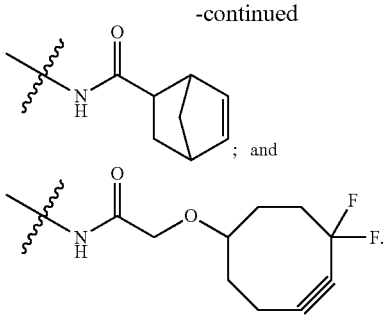
; and

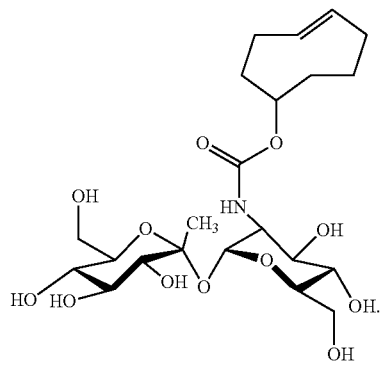

In some embodiments of the compounds of formula (VI), the compound is a compound of the following formula:

In some embodiments, the compound of formula (VI) is used to label bacteria that include trehalose in their cell walls. Examples of such bacteria include bacteria of the *Corynebacteria*, *Mycobacterium*, and *Nocardia* genera, e.g., *Corynebacterium diphtheriae*, *Mycobacterium bovis*, *Mycobacterium leprae*, *Mycobacterium tuberculosis*, *Nocardia asteroides* and *Nocardia brasiliensis*.

D. Linking Groups

In the affinity ligands of formula (I), the targeting ligand is attached to the chemical moiety A that includes a bioorthogonally reactive group by means of a bond or a linking group (L).

In some embodiments, L is a bond linking T and A.

In other embodiments, L is a chemical group linking T and A. Since the function of the linking group is merely to provide a physical connection between T and A, a wide variety of chemical groups can serve as linking groups L. L is typically a divalent organic linking group where one valency represents the point of attachment to T and one valency represents the attachment to A. The only requirement for the group L is to provide a stable physical linkage between L and T that is compatible with the binding of the targeting ligand to the bacterial cell and the bioorthogonal reaction that links A and B in the labeling method. In addition to chemical stability, L should lack chemically reactive groups that could compete or interfere with the labeling chemistry or otherwise react with the components that will be present in the medium in which labeling is performed.

Examples of suitable linking groups include, e.g.: —O—, —S—, —S(O)—, —S(O)$_2$—, —C(O)—, —NH—, —N(C$_1$-C$_6$)alkyl, —NHC(O)—, —C(O)NH—, —O(CO)—, —C(O)O—, —O(CO)NH—, —NHC(O)O—, —O(CO)O—, —NHC(O)NH—, —O(C$_1$-C$_6$)alkylene-, —S(C$_1$-C$_6$)alkylene-, —S(O)(C$_1$-C$_6$)alkylene-, —S(O)$_2$(C$_1$-C$_6$)alkylene-, —C(O)(C$_1$-C$_6$)alkylene-, —NH((C$_1$-C$_6$)alkylene)C(O)—, C(O)((C$_1$-C$_6$)alkylene)C(O)—, —C(O)((C$_1$-C$_6$)alkylene)NH—, —O(CO)—, —C(O)O—, —O(CO)NH—, —NHC(O)O—, —O(CO)O—, —NHC(O)NH—, unsubstituted-(C$_1$-C$_{10}$)alkylene-, unsubstituted-(C$_1$-C$_{10}$)heteroalkylene, or —(C$_1$-C$_{10}$)alkylene or —(C$_1$-C$_{10}$)heteroalkylene substituted with one or more (e.g., 1, 2, 3, 4 or 5 substituents) independently selected from the group consisting of (C$_1$-C$_6$)alkyl, (C$_2$-C$_6$)alkenyl, (C$_2$-C$_6$)alkynyl, halogen, (C$_1$-C$_6$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —((C$_1$-C$_6$)alkylene)Ar, —O((C$_1$-C$_6$)alkylene)Ar, —OC(=O)(C$_1$-C$_6$)alkyl, —OC(=O)O(C$_1$-C$_6$)alkyl, —OC(=O)NR$_2$, —NR$_2$, —NRAr, —NR((C$_1$-C$_6$)alkylene)Ar, —NRC(=O)R, —NRC(=O)Ar, —NRC(=O)O(C$_1$-C$_6$)alkyl, —NRC(=O)NR$_2$, —NRSO$_2$R, —SR, —S(O)R, —SO$_2$R, —OSO$_2$ (C$_1$-C$_6$)alkyl, —SO$_2$NR$_2$, (C$_1$-C$_8$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$, oxo and sulfido, wherein each R group is hydrogen or (C$_1$-C$_6$ alkyl), e.g., methyl and wherein each Ar is independently unsubstituted aryl or heteroaryl or aryl or heteroaryl substituted with one or more of (C$_1$-C$_6$) alkyl, (C$_2$-C$_6$)alkenyl, (C$_2$-C$_6$)alkynyl, halogen, (C$_1$-C$_6$)haloalkyl, —CN, —NO$_2$, —C(=O)R, —C(=O)OR, —C(=O)NR$_2$, —C(=NR)NR$_2$, —OR, —OC(=O)(C$_1$-C$_6$) alkyl, —OC(=O)O(C$_1$-C$_6$)alkyl, —OC(=O)NR$_2$, —NR$_2$, —NRC(=O)R, —NRC(=O)O(C$_1$-C$_6$)alkyl, —NRC(=O)NR$_2$, —NRSO$_2$R, —SR, —S(O)R, —SO$_2$R, —OSO$_2$(C$_1$-C$_6$)alkyl, —SO$_2$NR$_2$, (C$_1$-C$_8$)perfluoroalkyl, —(C$_2$-C$_6$)alkylene-OR, —O(C$_2$-C$_6$)alkylene-N((C$_1$-C$_6$)alkyl)$_2$, —P(=O)(OR)$_2$, —OP(=O)(OR)$_2$ wherein each R group is hydrogen or (C$_1$-C$_6$ alkyl). In addition, —(C$_1$-C$_{10}$)alkylene- and —(C$_1$-C$_{10}$)heteroalkylene can be substituted by one or more oxo groups (C=O) and the nitrogen and sulfur atoms of a heteroalkylene group can optionally be oxidized (e.g., to form S(O), —S(O)$_2$—, or N-oxide). Suitable heteroalkylene groups can include one or more 1,2-dioxyethylene units —(O—CH$_2$CH$_2$)$_n$O—, where n is an integer, e.g., 1, 2, 3, 4 or 5). The —(C$_1$-C$_{10}$)alkylene- and —(C$_1$-C$_{10}$)heteroalkylene also include —(C$_1$-C$_6$)alkylene- and —(C$_1$-C$_6$)heteroalkylene and —(C$_1$-C$_3$)alkylene- and —(C$_1$-C$_3$)heteroalkylene. Linking groups as shown in any of the examples can be applied as the linking group -L- any compounds of the general formula (I).

E. Magnetic Particles

The magnetic particles used for labeling bacteria as described herein include a core containing magnetic material, e.g., a magnetic oxide such as iron oxide. The particles typically have a diameter below 1 μm and therefore can be considered nanoparticles.

Magnetic nanoparticles can be monodisperse (a single crystal of a magnetic material, e.g., metal oxide, such as superparamagnetic iron oxide, per nanoparticle) or polydisperse (a plurality of crystals, e.g., 2, 3, or 4, per nanoparticle). The magnetic metal oxide can also comprise cobalt, magnesium, zinc, or mixtures of these metals with iron. The term "magnetic" as used in this specification and the accompanying claims means materials of high positive magnetic susceptibility such as superparamagnetic compounds and magnetite, gamma ferric oxide, or metallic iron. Features and elements of nanoparticles that can be useful to carry out the new conjugates include: (i) a high relaxivity, i.e., strong effect on water relaxation, (ii) a functional group to which the bioorthogonal group (B) can be covalently attached, (iii) a low non-specific binding of interactive moieties to the nanoparticle, and (iv) stability in solution, so that the magnetic nanoparticles do not precipitate.

The magnetic particles are attached (linked) to bioorthogonally reactive moieties via functional groups. In some embodiments, the magnetic particles are associated with a polymer that includes the functional groups, and also serves to keep the metal oxides dispersed from each other. The polymer can be a synthetic polymer, such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxymethyl dextran, and/or reduced carboxymethyl dextran. The metal oxide can be a collection of one or more crystals that contact each other, or that are individually entrapped or surrounded by the polymer.

While for simplicity, the formula of the magnetic agent has been depicted as M-B to depict the chemical moiety B comprising a bioorthogonally reactive group being attached to the magnetic particle M, the ratio of the number of bioorthogonally reactive groups to the number of magnetic particles is not necessarily 1:1. It may be that more than one B group is attached per magnetic particle.

In other embodiments, the magnetic particles are associated with non-polymeric functional group compositions. Methods are known to synthesize stabilized, functionalized magnetic particles without associated polymers, which are also within the scope of this invention. Such methods are described, e.g., in Halbreich et al., *Biochimie*, 1998, 80(5-6), 379-90.

The magnetic particles can have an overall size of less than about 50 μm. In some embodiments, the magnetic particles can have an overall size of less than about 1 μm. In some embodiments, the particles may have an overall size of less than about 100 nm. In some embodiments, the particles may have an overall size in the range from about 1-100 nm.

The metal oxides may comprise crystals of about 1-25 nm, e.g., about 3-10 nm, or about 5 nm in diameter.

The polymer component in some embodiments can be in the form of a coating, e.g., about 5 to 20 nm thick or more.

In some embodiments, the overall size of the magnetic particles is about 15 to 200 nm, e.g., about 20 to 100 nm, about 40 to 60 nm; or about 50 nm.

The conjugates have high relaxivity owing to the superparamagnetism of their iron or metal oxide. They may have an R1 relaxivity between about 5 and 30 mM$^{-1}$ sec$^{-1}$, e.g., 10, 15, 20, or 25 mM$^{-1}$ sec$^{-1}$. They may have an R2 relaxivity between about 15 and 100 mM$^{-1}$ sec$^{-1}$, e.g., 25, 50, 75, or 90 mM$^{-1}$ sec$^{-1}$. They may have a ratio of R2 to R1 of between 1.5 and 4, e.g., 2, 2.5, or 3. They typically have an iron oxide content that is greater than about 10% of the total mass of the particle, e.g., greater than 15, 20, 25 or 30 percent.

Synthesis of Magnetic Particles

There are varieties of ways that the magnetic particles can be prepared, but in all methods, the result must be a magnetic particle with functional groups that can be used to link the magnetic particle to the bioorthogonally reactive moiety.

For example, bioorthogonally reactive groups can be linked to the metal oxide through covalent attachment to a functionalized polymer or to non-polymeric surface-functionalized metal oxides. In the latter method, the magnetic particles can be synthesized according to the method of Albrecht et al., *Biochimie*, 1998, 80(5-6). 379-90. Dimercapto-succinic acid is coupled to the iron oxide and provides a carboxyl functional group. The term "functionalized" refers to the presence of amino or carboxyl or other reactive groups on the magnetic particle.

In some embodiments, the bioorthogonally reactive group is attached to magnetic particles via a functionalized polymer associated with the metal oxide. In some embodiments, the polymer is hydrophilic. In a specific embodiment, the bioorthogonally reactive group is attached by reacting a molecule (corresponding to the chemical moiety B, or a precursor thereof) that includes a hydroxyl, amino, sulfhydryl, carboxylate or phosphate groups, and superparamagnetic iron oxide nanoparticles bearing amino or carboxy groups on a hydrophilic polymer. There are several methods for synthesizing carboxy and amino derivatized magnetic particles. Methods for synthesizing functionalized, coated magnetic particles are discussed in further detail below.

Carboxy functionalized magnetic particles can be made, e.g., according to the method of Gorman, see WO 00/61191. In this method, reduced carboxymethyl (CM) dextran is synthesized from commercial dextran. The CM-dextran and iron salts are mixed together and are then neutralized with ammonium hydroxide. The resulting carboxy functionalized magnetic particles can be used for coupling a molecule that is functionalized, e.g., with an amino or hydroxyl group.

Carboxy-functionalized magnetic particles can also be made from polysaccharide-coated particles by reaction with bromo or chloroacetic acid in a strong base to attach carboxyl groups. In addition, carboxy-functionalized particles can be made from amino-functionalized magnetic particles by converting amino to carboxy groups by the use of reagents such as succinic anhydride or maleic anhydride.

Magnetic particle size can be controlled by adjusting reaction conditions, e.g., by using low temperature during the neutralization of iron salts with a base as described in U.S. Pat. No. 5,262,176. Uniform particle size materials can also be made by fractionating the particles using centrifugation, ultrafiltration, or gel filtration, as described, e.g., in U.S. Pat. No. 5,492,814.

Magnetic particles can also be synthesized according to the method of Molday et al., *J. Immunol. Methods*, 1982, 52(3), 353-67, and treated with periodate to form aldehyde groups. The aldehyde-containing particles can then be reacted with a diamine (e.g., ethylene diamine or hexanediamine), which will form a Schiff base, followed by reduction with sodium borohydride or sodium cyanoborohydride.

Dextran-coated magnetic particles can be made and cross-linked with epichlorohydrin. The addition of ammonia will react with epoxy groups to generate amine groups. Hogemann, et al., *Bioconjug. Chem.* 2000, 11(6), 941-46, and Josephson et al., *Bioconjug. Chem.*, 1999, 10(2), 186-91. This material is known as cross-linked iron oxide or "CLIO" and when functionalized with amine is referred to as amine-CLIO or $NH_2$—CLIO.

Carboxy-functionalized magnetic particles can be converted to amino-functionalized magnetic particles by the use of water-soluble carbodiimides and diamines such as ethylene diamine or hexane diamine Avidin or streptavidin can be attached to magnetic particles for use with a biotinylated compound. See, e.g., Shen et al., *Bioconjug. Chem.*, 1996, 7(3), 311-16. Similarly, biotin can be attached to a magnetic particle for use with an avidin-labeled compound.

In some embodiments, the magnetic particle, in addition to including the bioorthogonally reactive group, also fluorescent groups bound to its surface so that the magnetic particles are fluorescent (i.e., magnetofluorescent particles).

In some embodiments, the magnetic particles are tetrazine-conjugated particles, wherein B comprises a 1,2,4,5-tetrazine group. In some embodiments, the magnetic particles are magnetofluorescent tetrazine-conjugated particles.

In all of these methods, low molecular weight compounds can be separated from the magnetic particles by ultrafiltration, dialysis, magnetic separation, or other means.

Various strategies for coupling molecules to magnetic particles are summarized in Table 1 below.

TABLE 1

Functional Groups and Strategies for coupling molecules to magnetic particles

| Molecule Functional Group | Magnetic particle Functional Group | Coupling Chemistry | Cleavable |
|---|---|---|---|
| Sulfhydryl | Amino | SPDP, lc-SPDP (lc, long chain) | Yes |
| Sulfhydryl | Amino | Succinimidyl-iodoacetate | No |
| Amino | Carboxyl | CDI (carbodiimide) | No |
| Phosphate | Amino | CDI | No |
| Biotin | Avidin | Not applicable | Not applicable |

III. Kits

The present disclosure also provides a kit for the magnetic labeling of a bacterial cell. The kit includes an affinity ligand of the formula (I):

T-L-A      (I)

wherein:
T is a targeting ligand that binds or reacts selectively with a component of the bacterial cell;
A is a chemical moiety comprising a first bioorthogonally reactive group; and
L is a bond or a linking group attaching A to T;
and a magnetic agent of the formula (II):

B-M      (II)

wherein:
M is a magnetic particle; and
B is a chemical moiety comprising a second bioorthogonally reactive group that is covalently attached to the magnetic particle; and
wherein the first and second bioorthogonally reactive groups are complementary and can react with each other to form at least one covalent bond.

In addition to the affinity ligand and magnetic particles, the kit may also contain any additional reagents or catalysts required to provide conditions sufficient for the first and second bioorthogonally reactive groups to react to form at least one covalent bond linking A and B.

In some embodiments, the kits as provided herein may include targeting ligands that are suitable for binding or reacting selectively to any one or more of the classes, genera, or species of bacterial cells, as described in section II(A) above.

In addition, in some embodiments, the compounds of formula (I) and (II) included in the kits as provided herein may include any of the bioorthogonally reactive groups, as described in section II(B) above.

In addition, in some embodiments, the compounds of formula (I) included in the kits as provided herein may include any of the targeting ligands or the affinity ligands, as described in section II(C) above.

In some embodiments, the compounds of formula (I) included in the kits as provided herein may include any of the linking groups, as described in section II(D) above.

In some embodiments, the magnetic particles of formula (II) included in the kits as provided herein may be as described in section II(E) above.

Such embodiments may be combined in any combination.

IV. Affinity Ligands

The present application also provides affinity ligands that are suitable for bioorthogonal labeling of bacterial cells.

The affinity ligand includes compounds of the following formula:

T-L-A      (I)

wherein
T is a targeting ligand that binds or reacts selectively with a component of the bacterial cell;
A is a chemical moiety comprising a bioorthogonally reactive group; and
L is bond or a linking group attaching A to T.

The affinity ligand may be according to any of the embodiments described above. For example, affinity ligands provided herein may include targeting ligands that are suitable for binding or reacting selectively to any one or more of the classes, genera, or species of bacterial cells, as described in section II(A) above.

In addition, in some embodiments, the affinity ligands of formula (I) may include any of the bioorthogonally reactive groups, as described in section II(B) above.

In addition, in some embodiments, the affinity ligands of formula (I) included in the kits as provided herein may include any of the targeting ligands or the affinity ligands, as described in section II(C) above.

In some embodiments, the affinity ligands of formula (I) included in the kits as provided herein may include any of the linking groups, as described in section II(D) above.

In some embodiments, the affinity ligands of formula (I) may be suitable for use together with any of the magnetic particles of formula (II) included in the kits as provided herein may be as described in section II(E) above.

Such embodiments may be combined in any combination.

IV. Applications

The bioorthogonal labeling methods, kits and affinity ligands described herein are useful, e.g., for some of the applications described below.

Magnetic (rather than optical) labeling and detection is advantageous because of its high sensitivity and ability to diagnose crude specimens without major purification. Issadore et al., *Lab Chip*, 2011, 11, 147-51.

The magnetic labeling methods may be carried out to rapidly and sensitively detection of bacterial samples by using a miniaturized micro-nuclear magnetic resonance (μNMR) device. Liong et al., *Bioconjug Chem*, 2011, 22, 2390-4. Direct bacterial detection by μNMR is a sensitive diagnostic method and potentially allows the exclusion of culturing steps thus minimizing the time required for diagnosis. Panizzi et al., *Nat. Med.* 2011, 17, 1142-6. Alternative magnetic detection devices include giant magnetoresistance. Li et al., *J. Med. Devices*, 2008, 2, 27529. A further type of magnetic detection device that can be used is a Hall effect sensor. Lönnbro et al., *BMC Cell Biology* 2008, 9, 35.

Additional applications of magnetically labeling bacteria include magnetic separation (Lönnbro et al., *BMC Cell Biology* 2008, 9, 35; Yang et al., *J. Microbiol. Methods*, 2011, 86, 69-77); cell sorting (Guillebault, et al., *Appl. Environ. Microbiol.*, 2010, 76, 7352-7355); magnetic force microscopy (Zhang et al., *Biotechnol. Frog.*, 2009, 25, 923-928) and micromanipulation and force measurements using magnetic tweezers, Chaves, et al., *J. Appl. Phys.*, 2011, 109, 064702.

EXAMPLES

Figure 2:
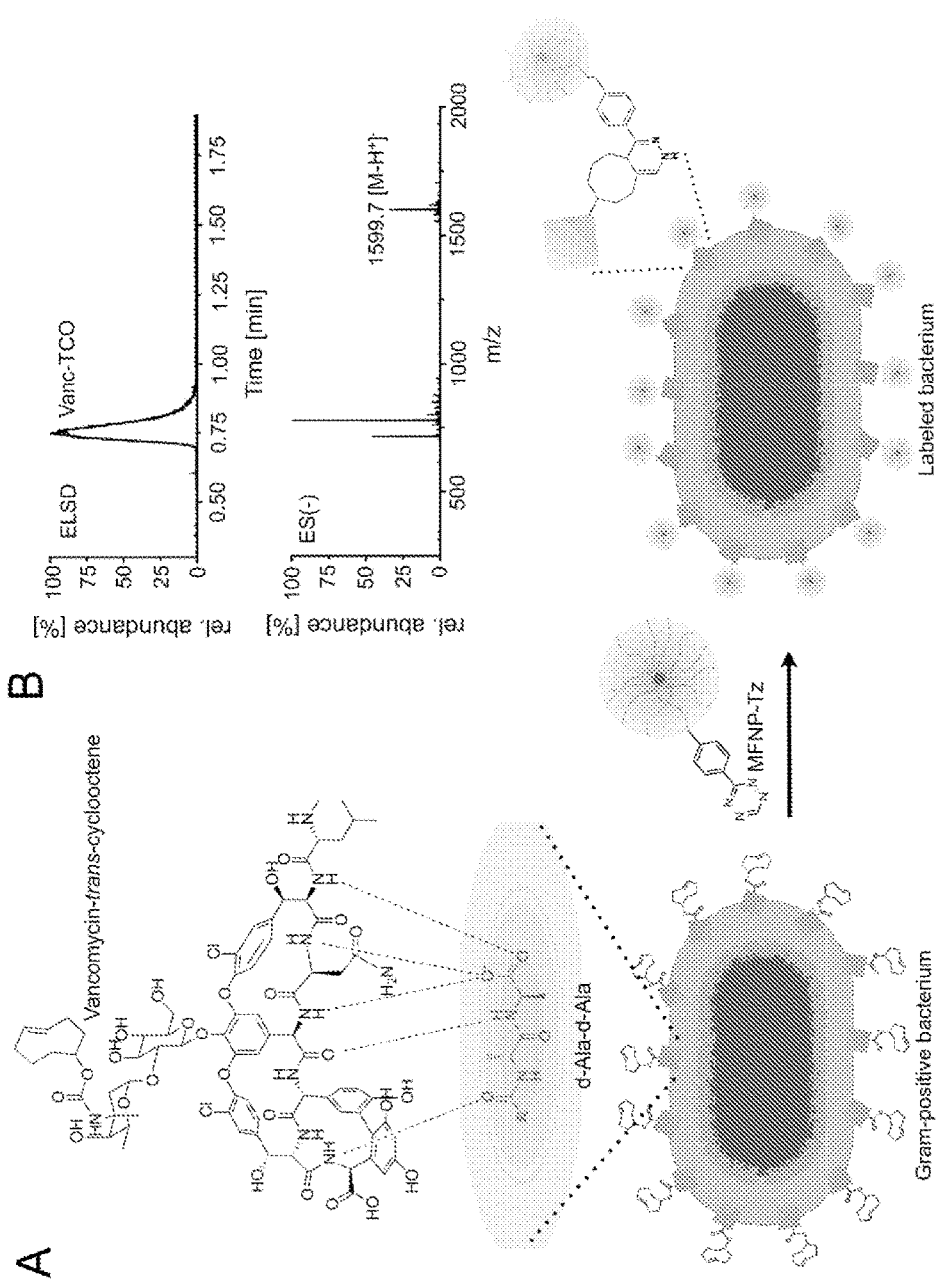
FIG. 2 shows (A) the chemistry of bioorthogonal magnetofluorescent nanoparticle labeling using vancomycin-linked magnetic particles and (B) HPLC and ESI-MS traces of a vancomycin-trans-cyclooctene ligand.

Example 1. Magnetic Labeling Of Bacteria Using a Vancomycin-Trans-Cyclooctene Conjugate The Example below describes labeling of Gram-positive bacteria using trans-cyclooctene (TCO) conjugates of vancomycin, an antibiotic that bind selectively to Gram-positive bacteria, i.e., vancomycin. The labeling scheme for vancomycin is shown in FIG. 2. FIG. 2A shows that vancomycin-trans-cyclooctene (vancomycin-TCO) targets Gram-positive bacteria by binding onto its membrane subunits. Following incubation with MFNP-Tz, bacteria are labeled and can be detected via fluorescent or magnetic sensors. FIG. 2B shows HPLC (top) and ESI-MS (bottom) traces of vancomycin-TCO verifying its identity and purity.

1. Synthesis of Vancomycin-Trans-Cyclooctene (TCO) Conjugate (E)-Cyclooct-4-enyl 2,5-dioxopyrrolidin-1-yl carbonate (trans-cyclooctene N-hydroxy-succinimidyl ester; TCO-NHS) was synthesized as described by Devaraj et al., *Angew. Chem. Int. Ed. Engl.* 2009, 48, 7013-7016.

8.4 mg (5.8 µmol) of vancomycin in DMF (1 mL) or acetonitrile (2 mL), respectively, was added to a solution of TCO-NHS (400 µL, 10 mg/mL in DMF) and Et$_3$N (8.1 µL, 58 µmol). The reaction mixture was stirred for 6 h before being analyzed with liquid chromatography electrospray ionization tandem mass spectrometry (LC-ESI-MS) and high performance liquid chromatography (HPLC) using a Waters (Milford, Mass.) LC-MS system. For LC-ESI-MS analyses, a Waters XTerra® C18 5 µm column was used. For preparative runs, an Atlantis® Prep T3 OBD™ 5 µM or an XTerra® Prep MS C18 OBD™ 5 µm column was used. High-resolution electrospray ionization mass spectrometry (HRMS-ESI) was performed using a Bruker Daltonics APEXIV 4.7 Tesla Fourier Transform mass spectrometer (FT-ICR-MS) in the Department of Chemistry Instrumentation Facility at Massachusetts Institute of Technology. The yield was 23% (2.1 mg, 1.3 µmol). Characterization by LC-ESI-MS and HRMS-ESI resulted in the following values:

vancomycin-TCO: LC-ESI-MS(−) m/z=1599.7 [M−H$^+$]$^-$; LC-ESI-MS (+) m/z=1600.7 [M+H$^+$]$^+$; HRMS-ESI [M+H]$^+$ m/z calculated for [C$_{25}$H$_{87}$Cl$_2$N$_9$O$_{26}$]$^+$ 1600.5218. found 1600.5230.

2. Preparation of Tetrazine-Conjugated Nanoparticles

Magnetofluorescent nanoparticles (MFNPs) were synthesized as described by Josephson, et al. *Bioconjug. Chem.* 1999, 10, 186-191. The nanoparticles had a 3 nm core of (Fe$_2$O$_3$)$_m$(Fe$_3$O$_4$)$_n$ coated with a layer of cross-linked dextran. The average hydrodynamic diameter was 21 nm, and each particle had 22 free amine groups and 8.4 molecules of fluorescein conjugated on the surface. The measured r$_1$ and r$_2$ relaxivity values were 23 s$^{-1}$ mM$^{-1}$ [Fe] and 51 s$^{-1}$ mM$^{-1}$ [Fe], respectively.

Amine-reactive tetrazine (Tz-NHS) was synthesized as described by Haun et al., *Nat. Nanotechnol.* 2010, 5, 660-665. In brief, 3-(4-benzylamino)-1,2,4,5-tetrazine was used to produce 2,5-dioxopyrrolidin-1-yl 5-(4-(1,2,4,5-tetrazin-3-yl)benzylamino)-5-oxopentanoate. Tz-conjugated magnetofluorescent nanoparticles (MFNP-Tz) were prepared by reacting Tz NHS with amine-functionalized MFNPs. MFNPs were added to a solution containing 500 times molar excess of Tz-NHS, and allowed to react in a 1:9 dimethylsulfoxide (DMSO)/phosphate buffered saline (PBS) solution containing 10 mM sodium bicarbonate at room temperature for 4 h. Unreacted Tz-NHS was removed using Sephadex G-50 (GE Healthcare).

3. Preparation of Vancomycin-Conjugated Nanoparticles

To directly conjugate MFNPs with vancomycin, the amine groups of MFNPs were first converted to carboxyl groups by reacting them with 1000 times molar excess of succinic anhydride in PBS (containing 10 mM sodium bicarbonate), at room temperature for 4 h. After purification of the nanoparticles with Sephadex G-50, the carboxylated MFNPs were reacted with N-ethyl-N'-(3-dimethylaminopropyl)carbodiimide (EDC; Sigma-Aldrich) and N-hydroxysulfosuccinimide (sulfo-NHS; Pierce) in PBS at room temperature for 1 h (molar ratio of MFNP:EDC:sulfo-NHS=1:1000:1000). NHS-activated MFNPs were then purified with Sephadex G-50, reacted with vancomycin (1000-fold molar excess) in PBS for 2 h at room temperature, and finally purified using Sephadex G-50.

4. Bacterial Cultures

Bacterial strains *Staphylococcus aureus* (*S. aureus;* #25923), *Streptococcus pneumoniae* (*S. pneumoniae;* #6318), *Staphylococcus epidermidis* (*S. epidermidis;* #29886), *Enterococcus faecalis* (*E. faecalis;* #29212), *Escherichia coli* (*E. coli;* #25922), *Pseudomonas aeruginosa* (*P. aeruginosa;* #142), and *Klebsiella pneumoniae* (*K. pneumoniae;* #43816) were purchased from ATCC (Manassas, Va.). *S. aureus* and *S. epidermidis* were plated in mannitol salt agar (BD Biosciences, Sparks, Md.) and colonies were cultured in *Staphylococcus* broth (BD Biosciences) for growth overnight. *S. pneumoniae* was plated onto selective *streptococcus* agar and the colony was seeded into Tryptic Soy Broth containing 5% defibrinated sheep blood (Hemostat Laboratories, Dixon, Calif.) for growth. *P. aeruginosa* was plated on *Pseudomonas* isolation agar, and *E. faecalis, E. coli*, and *K. pneumoniae* were plated onto standard agar plates. For growth, *P. aeruginosa* and *K. pneumoniae* were cultured in Tryptic Soy Broth, *E. faecalis* was cultured in Tryptic Soy Broth containing 5% defibrinated sheep blood, and *E. coli* was cultured in Luria-Bertani (LB) media (BD Biosciences). Bacterial cell numbers were determined by plating onto standard agar plates and by counting the number of colony forming units (CFU).

5. Bacterial Labeling and Detection

Bacterial cells were first washed with PBS solution containing 2% fetal bovine serum (FBS) and 1 mg/ml bovine serum albumin (BSA; PBS-F).

For two-step labeling, the washed cells were incubated with 1-20 µM vancomycin TCO in PBS-F at room temperature for 30 min. For competition studies, 1-200 µM unmodified vancomycin was added to 20 µM vancomycin-TCO.

For two-step labeling using Daptomycin-TCO, the drug conjugates were incubated in buffer solution containing 5 mM 4-(2-hydroxyethyl)-1-piperazineethanesulfonic acid (HEPES), 5 mM $CaCl_2$, 2% FBS, and 1 mg/ml BSA at room temperature for 30 min. After washing twice with PBS-F, bacterial cells were incubated with 50 µg/ml MFNP-Tz in PBS-F for 20 min. at room temperature.

For one-step labeling using directly conjugated MFNPs, bacteria were incubated with 50 µg/ml MFNP-vancomycin in PBS-F for 30 min. at room temperature. Unbound MFNPs were removed by washing the cells twice in PBS-F.

For fluorescence spectrometry, µNMR measurements, and flow cytometry, the cells were fixed in 10% paraformaldehyde (PFA) for 30 min., and then exchanged into PBS solution. Fluorescence measurements were taken using the Safire2 microplate reader (TECAN, Mannedorf, Switzerland). Increased relative fluorescence intensity (% RFU) values were calculated as $100 \times (I_{target} - I_{non})/I_{non}$, where $I_{target}$ and $I_{non}$ are intensity values of targeted and non-targeted bacteria, respectively. Flow cytometry was performed using LSRII (BD Biosciences). All labeling experiments and measurements were performed at least 3 times to confirm the reproducibility and robustness of the method.

6. Intracellular Detection

RAW 264.7 mouse macrophages attached to culture slides were treated for 1 h with either *S. aureus* or *E. coli* (200 CFUs per single macrophage) in serum-free Dulbecco's modified Eagle medium (DMEM) containing 100 µM chloroquine (to prevent degradation of phagocytized bacteria). Macrophages were then washed thoroughly with DMEM, and treated with 20 µM vancomycin-TCO in DMEM containing 2% FBS (DMEM-F) for 1 h. After washing away any unbound vancomycin-TCO with DMEM-F, 50 µg/ml MFNP-Tz in DMEM-F containing 10% permeabilizing buffer (BD Phosflow) was added, before incubating the solution for 40 min. All treatments were performed in a 37° C. $CO_2$ incubator. Cells were then washed extensively with DMEM and stained with CellTracker Red (Invitrogen).

7. Microscopy

For confocal microscopy, bacterial cells were fixed in 10% PFA for 30 min., mounted onto poly(L-lysine) coated microscopic slides using Vectashield with propium iodide (Vector Laboratories, Burlingame, Calif.), and observed under a laser scanning confocal microscope (LSM 5 Pascal, Carl Zeiss, Jena, Germany).

For observing macrophages, cells were fixed in 10% PFA for 30 min. and mounted using Vectashield including 4',6-diamidino-2-phenylindole (DAPI)(Vector Laboratories). For electron microscopy, bacterial cells were fixed in 2.5% glutaraldehyde for 30 min., dehydrated with a series of graded ethanol solutions, and mounted onto carbon-mesh coated copper grids (Ted Pella, Redding, Calif.) for subsequent observation under a transmission electron microscope (JEM 2011, Jeol Ltd., Tokyo, Japan).

8. Micro Nuclear Magnetic Resonance (µNMR)

All µNMR measurements were performed using the portable NMR system recently developed for point-of-care operations as described by Issadore, et al. *Lab Chip* 2011, 11, 2282-87. The polarizing magnetic field was ~0.5 T. Transverse relaxation times were measured on 1-2 µL sample volumes, using Carry-Purcell-Meiboom-Gill pulse sequences with the following parameters: echo time, 3 ms; repetition time, 4 s; number of 180° pulses per scan, 900; number of scans, 7. All measurements were done in triplicate, and data are displayed as mean±standard error of mean.

9. Results a. Vancomycin-TCO Binding to Gram-Positive Bacteria

Incubation with vancomycin-TCO and MFNP-Tz with *Staphylococcus aureus* (*S. aureus*), resulted in highly effective bacterial targeting, as shown by the results in FIG. 1.

Figure 3:
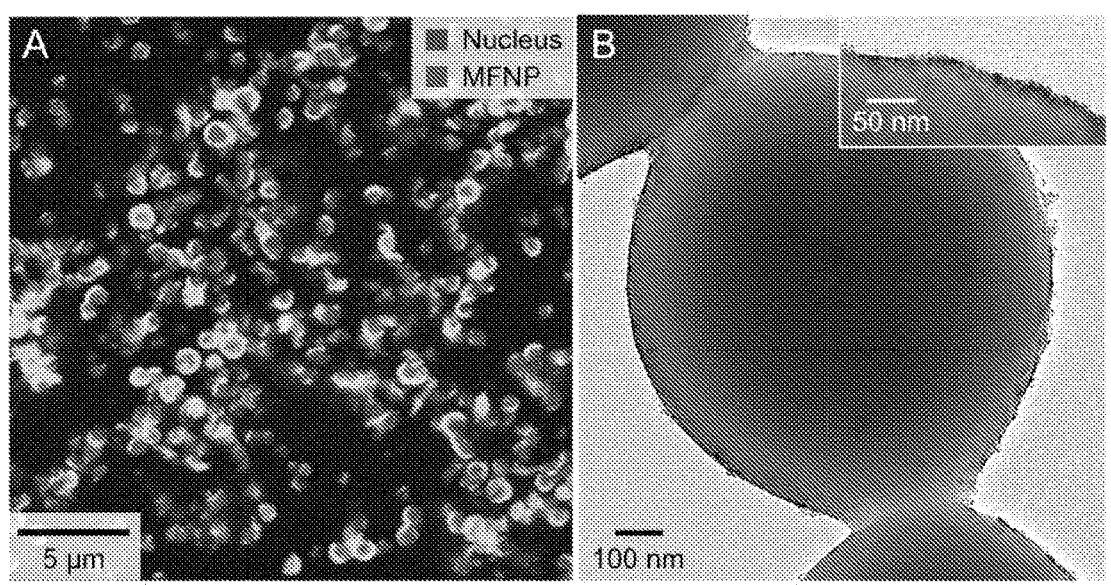
FIG. 3 shows the results of the two step-labeling of S. aureus using a vancomycin-trans-cyclooctene ligand (vancomycin-TCO) and tetrazine-linked magnetofluorescent nanoparticles (MFNP-Tz) as observed using (A) confocal microscopy and (B) transmission electron microscopy.

FIG. 3 shows the results of the two step-labeling of *S. aureus* as observed using (A) confocal microscopy and (B) transmission electron microscopy after labeling *S. aureus* with vancomycin-TCO and MFNP-Tz. FIG. 3A shows bright fluorescence on the surface and outer layer of the bacterial cells. FIG. 3B shows transmission electron microscopy images showing the presence of nanoparticles, evenly coated across the surface of bacterial cells. The inset in the top right of FIG. 3B shows the labeling at a higher magnification.

Figure 4:
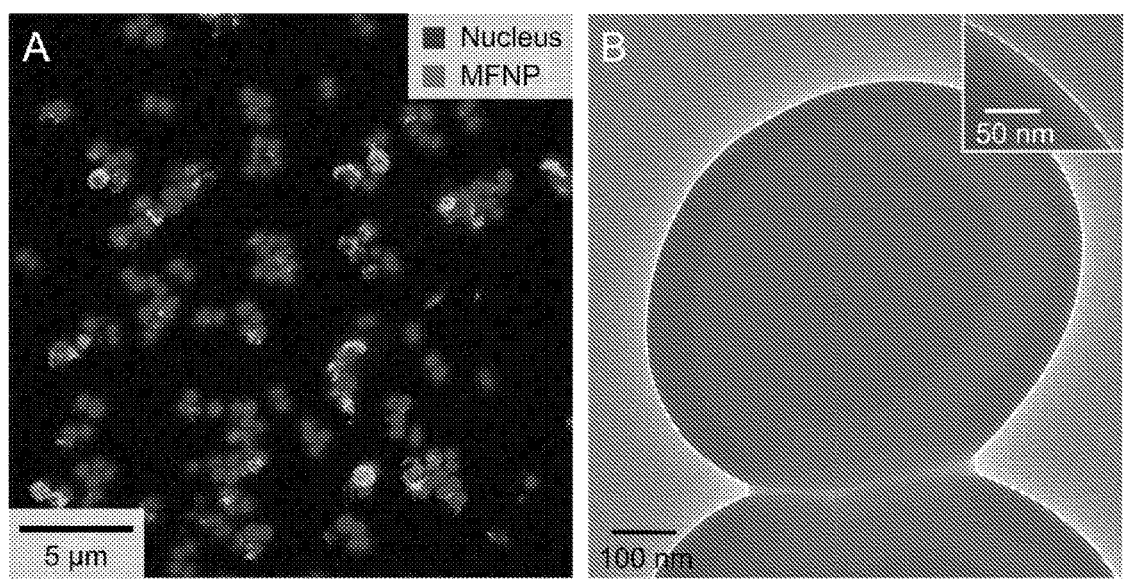
FIG. 4 shows the results of a control experiment in which S. aureus was incubated with magnetofluorescent nanoparticles (MFNP-Tz) without first incubating with vancomycin-TCO.

FIG. 4 shows the results of a control experiment in which *S. aureus* was incubated with MFNP-Tz without first incubating with vancomycin-TCO, observed using (A) confocal microscopy and (B) transmission electron microscopy. Although some non-specific labeling can be seen, this was low compared to the values for specific labeling (e.g., 40-fold lower MFI in flow cytometry for *S. aureus*). As shown in FIG. 4B, transmission electron spectroscopy showed a smooth surface devoid of nanoparticles. The inset at the right of FIG. 2B shows the absence of labeling at high magnification.

b. Detection of Gram-Positive Bacteria Via Vancomycin Cycloaddition to Nanoparticles The following panel of Gram-positive bacteria was tested: *Staphylococcus aureus* (*S. aureus*), *Streptococcus pneumoniae* (*S. pneumoniae*), *Staphylococcus epidermidis* (*S. epidermidis*), and *Enterococcus faecalis* (*E. faecalis*). The following Gram-negative species were used as negative controls: *Escherichia coli* (*E. coli*), *Pseudomonas aeruginosa* (*P. aeruginosa*), and *Klebsiella pneumoniae* (*K. pneumoniae*).

Using these bacteria, the optimal vancomycin-TCO dose for bacterial labeling was determined. All bacterial samples were incubated with varying concentrations of vancomycin-TCO, before subsequent labeling with MFNP-Tz.

Figure 5:
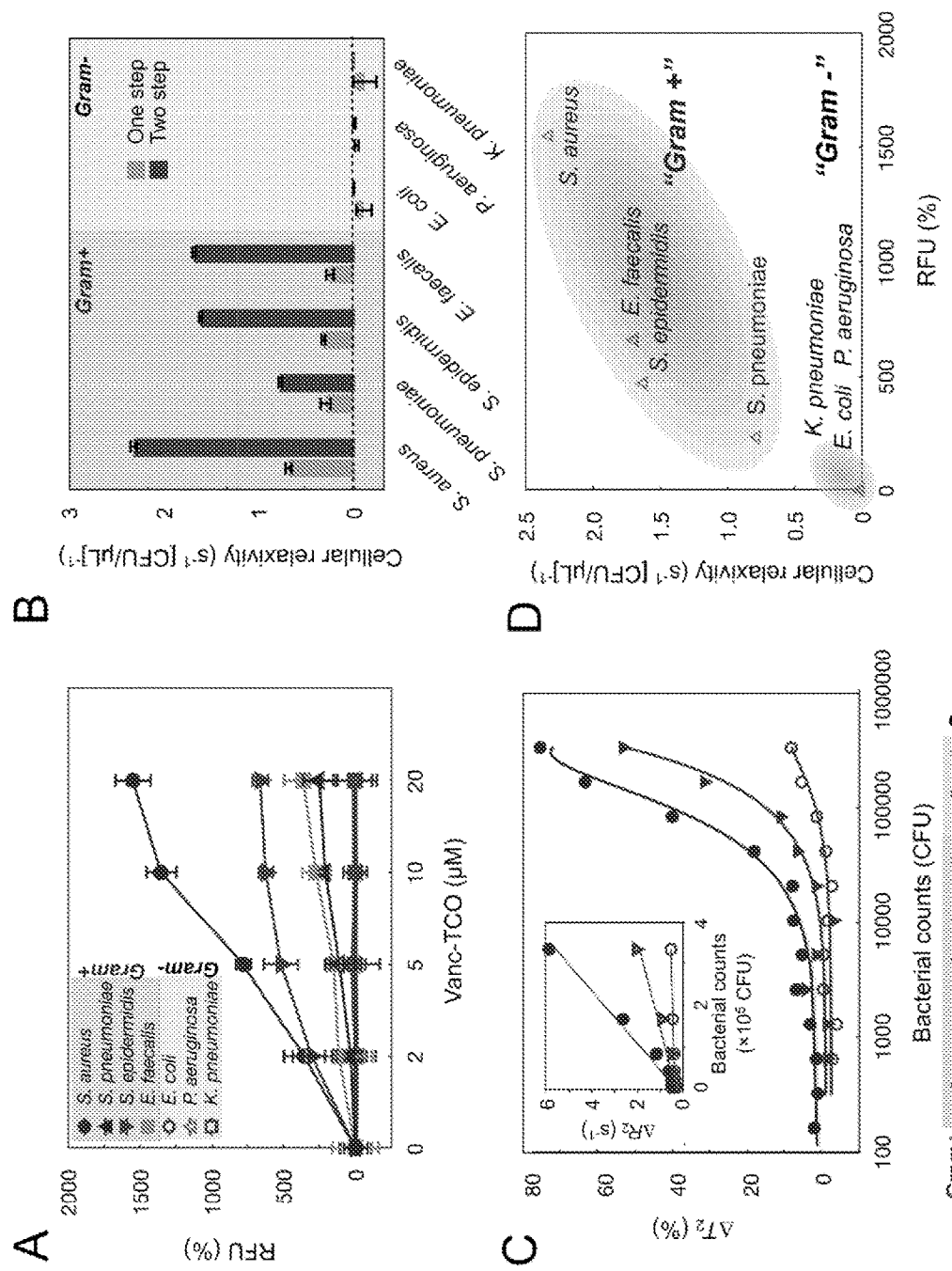
FIG. 5 shows the results of experiments on bacterial detection using vancomycin-TCO (A) using fluorescence detection of MFNP-labeled bacteria as a function of vancomycin-TCO concentration; (B) using magnetic resonance detection of bacteria following the two-step cycloaddition labeling method compared to that following the one-step labeling method (C) determining detection sensitivity for bacterial strains by measuring serially diluted suspensions of labeled bacteria; and (D) the correlation of magnetic resonance and fluorescence-based detection of the labeled bacteria.

FIG. 5A shows the results of fluorescence detection of MFNP-labeled bacteria as a function of vancomycin-TCO concentration. For all Gram-positive bacteria, fluorescence intensities increased proportionally with vancomycin-TCO concentration until saturation was attained. Treating with higher concentrations of vancomycin-TCO (50, 100 µM) resulted in lower labeling efficiencies than at 20 µM due to the bactericidal effect of the drug conjugates. Therefore, the optimal dose of vancomycin-TCO for targeted labeling was determined to be about ~20 µM. The equilibrium binding constant $K_d$ (=5.7 µM) of vancomycin-TCO was statistically similar (p>0.28) across all Gram-positive species. The Gram-negative species (controls) showed negligible fluorescent signals at all vancomycin-TCO concentrations tested.

FIG. 5B shows the results of an experiment performed to compare the efficacy of the bioorthogonal two-step labeling approach to that of attempting to label with direct covalent conjugates of vancomycin-nanoparticles. Bacterial samples were magnetically targeted using both labeling methods, and the transverse relaxation time ($T_2$) of all samples was measured using a miniature (micro) nuclear magnetic resonance (µNMR) system. Lee et al. *Proc. Natl. Acad. Sci. USA* 2009, 106, 12459-12464; and Issadore et al. *Lab Chip* 2011, 11, 2282-2287. The $T_2$ values were then converted to cellular relaxivity values ($1/T_2$ per bacterial concentration), which are proportional to the amount of MFNPs loaded onto each bacterium. From this comparison, it was found that the cellular relaxivities of bioorthogonally targeted bacteria were up to 6-fold higher than those of direct conjugates showing, surprisingly, that the bioorthogonal approach provided much more efficient labeling of Gram-positive targets.

FIG. 5C shows detection sensitivity for bacterial strains determined by measuring serially diluted suspensions of labeled bacteria. The detection limits of *S. aureus* and *S. epidermidis* using the bioorthogonal labeling method were 1,300 CFU and 35,100 CFU, respectively.

FIG. 5D shows the correlation of magnetic resonance and fluorescence-based detection of the labeled bacteria, demonstrating good correlation between the µNMR assay reported and fluorescence measurements.

Figure 6:
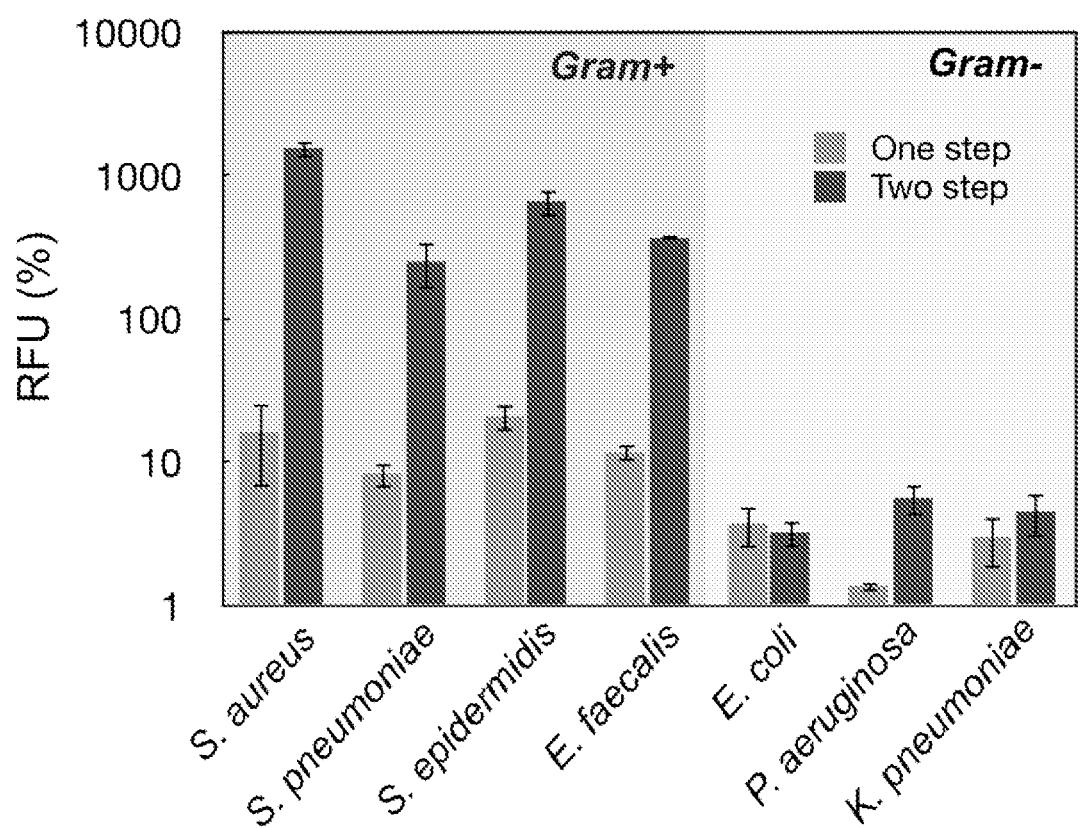
FIG. 6 shows the results of an experiment performed to compare the efficacy of the bioorthogonal two-step labeling approach to that of attempting to label with direct covalent conjugates of vancomycin-nanoparticles.

FIG. 6 shows the results of an experiment performed to compare the efficacy of the bioorthogonal two-step labeling approach to that of attempting to label with direct covalent conjugates of vancomycin-nanoparticles using optical detection. RFU: relative fluorescence intensity. Binding efficacy using the bioorthogonal method was typically one to two orders of magnitude higher than that of a direct conjugates.

Figure 7:
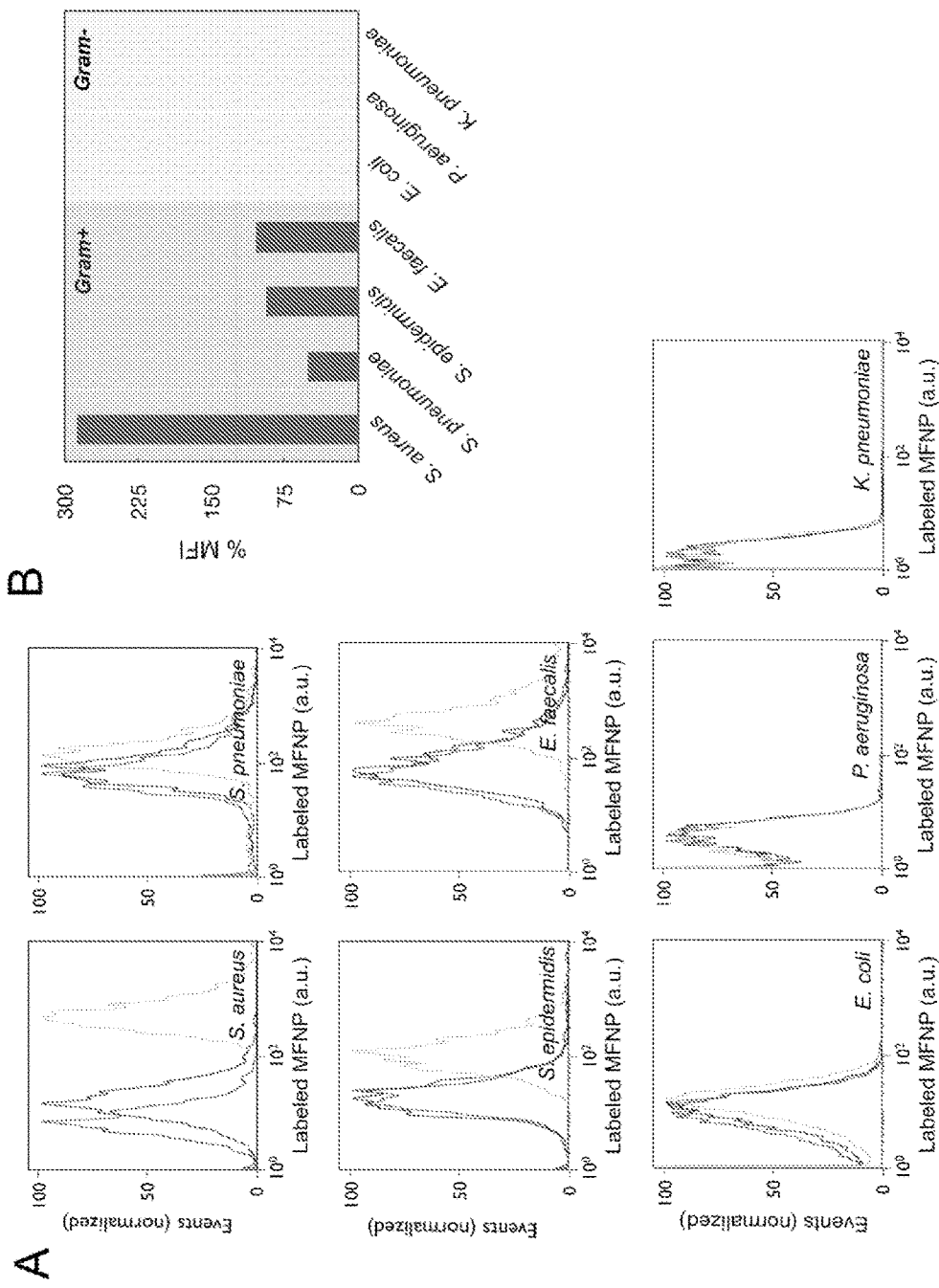
FIG. 7 shows the results of flow cytometry analyses of vancomycin-TCO labeled bacteria showing (A) histograms obtained for targeted, non-targeted and control bacteria and (B) mean fluorescence intensity values for various bacterial strains.

FIG. 7 shows flow cytometry analyses of vancomycin-TCO-labeled bacteria. FIG. 7A shows histograms for targeted bacteria (incubated with both vancomycin-TCO and MFNP-Tz; green-lighter line color), non-targeted bacteria (incubated with MFNP-Tz only; blue), and control bacteria (no incubation; red). FIG. 7B shows mean fluorescence intensity (MFI) values, as determined by FlowJo software. % MFI values were calculated by subtracting the intensity values for targeted bacteria from those of non-targeted bacteria, and then dividing by the intensity values of non-targeted bacteria. The flow cytometry results confirm that the Gram-positive bacteria, but not the Gram-negative bacteria were labeled efficiently and evenly throughout the cell population.

c. Functional Assays

To further characterize the binding properties of vancomycin-TCO, competitive inhibition studies were performed in which unmodified vancomycin was introduced together with vancomycin-TCO, before reacting with MFNP-Tz. The results of the experiments are shown in FIGS. 8A-C.

Figure 8:
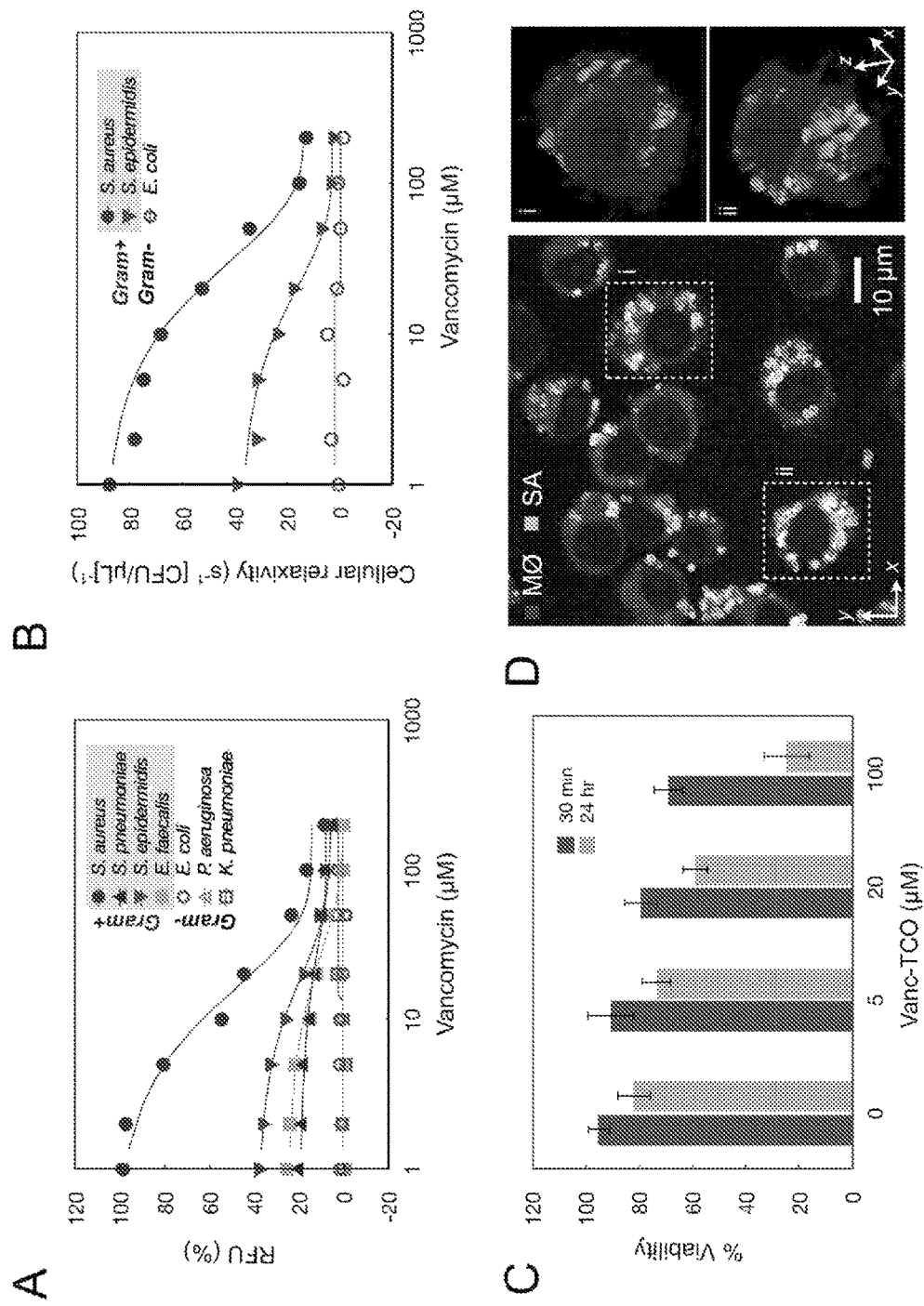
FIG. 8 shows results of competition studies of vancomycin-TCO using (A) fluorescence and (B) magnetic resonance measurements; (C) shows the effect of vancomycin-TCO on viability of S. aureus; and (D) shows the intracellular detection of S. aureus in macrophages.

FIGS. 8A and 8B show the results of competition studies of vancomycin-TCO using both fluorescence (FIG. 8A) and magnetic resonance (FIG. 8B) measurements. As the concentration of unmodified vancomycin increased, the labeling efficacy of Gram-positive bacteria gradually decreased. The inhibition binding constant ($K_i$) was about 6 µM for all Gram-positive bacteria, a value which was similar to that of vancomycin-TCO.

FIG. 8C shows the effect of vancomycin-TCO on viability of *S. aureus* measured using a BacLight viability kit after incubation of *S. aureus* with vancomycin-TCO for either 30 min. or 24 h, showing that Vancomycin retained its bactericidal activity after the chemical modification with TCO.

d. Detection of Intracellular Bacteria

In vivo, bacteria are often present within phagocytic cells and thereby escape detection; this is especially true in chronic inflammation. Experiments were therefore performed to test whether the bioorthogonal labeling method could be used for intracellular detection of such pathogens.

Macrophages in culture were incubated with *S. aureus* and then washed to remove extracellular pathogens. The cells were subsequently treated with vancomycin-TCO and MFNP-Tz, as described above but with some modifications. First, when targeting cells with MFNPs, a small amount of cell permeabilization solution containing saponin was added. This agent maintains the viability and integrity of live cells better than other permeabilizing agents. Haun et al., *ACS Nano* 2011, 5, 3204-3213. The semi-permeabilization allows entry of MFNPs by penetration through the cell membranes rather than by phagocytosis. Second, the particles were incubated for a longer time to allow for delivery of MFNPs into the macrophages and their subsequent binding to intracellular bacteria.

The results of the experiment are shown in FIG. 8D, which shows-dimensional images (left: top view, right: perspective view) showing the intracellular detection of *S. aureus* (SA) in semipermeabilized live macrophages (MO). The bright areas (green) show MFNPs while the grey areas (red) shows the cytoplasm of macrophages. The experiment demonstrates that *S. aureus* could be labeled intracellularly within live macrophages.

Figure 9:
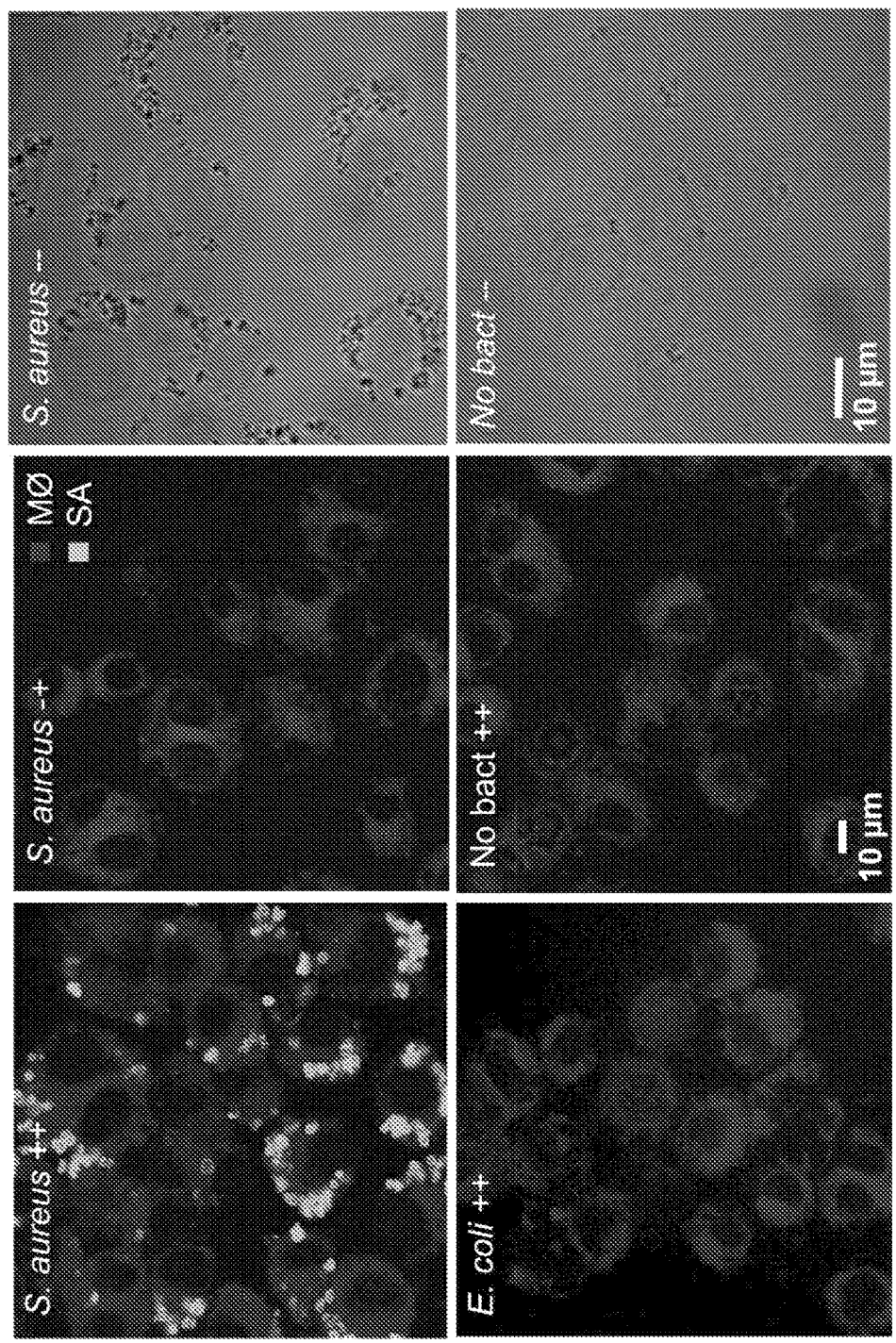
FIG. 9 shows the intracellular detection of bacteria in macrophages.

As a control experiment, to eliminate the possibility that the results were simply the result of normal phagocytosis, identical experiments were performed on *E. coli* as well as in the absence of bacteria. The results are shown in FIG. 9, which shows confocal (left and middle column) and bright field images (right column) showing *S. aureus* (SA) or *E. coli* engulfed by macrophages (MØ), or no engulfment (no bacteria), as well as the effect of vancomycin-TCO and MFNP-Tz treatment (++), MFNP-Tz only treatment (−+), or no treatment (−−). The bright patches (green) indicate MFNPs, while the dark grey areas show the cytoplasm of macrophages. MFNPs are within the macrophages only in the presence of *S. Aureus* (and not *E. coli*, or in the absence of bacteria). Further, MFNPs within the macrophages only observed with vancomycin-TCO treatment prior to MFNP-Tz treatment, and not when MFNP-Tz treatment is carried out without vancomycin-TCO treatment.

Example 2. Magnetic Labeling of Bacteria Using a Daptomycin-Trans-Cyclooctene Conjugate The Example below describes labeling of Gram-positive bacteria using trans-cyclooctene (TCO) conjugates of daptomycin, another antibiotic that bind selectively to Gram-positive bacteria.

1. Synthesis of Daptomycin-Trans-Cyclooctene (TCO) Conjugates

Unless otherwise noted, all reagents for syntheses of the daptomycin-TCO conjugates were purchased from Sigma-Aldrich (St. Louis, Mo.) and used without further purification.

9.4 mg (5.8 µmol) of daptomycin (Cubicin; Cubist Pharmaceuticals, Lexington, Mass.) in DMF (1 mL) or acetonitrile (2 mL), respectively, was added to a solution of TCO-NHS (400 µL, 10 mg/mL in DMF) and Et$_3$N (8.1 µL, 58 µmol). The reaction mixture was stirred for 6 h before being analyzed with liquid chromatography electrospray ionization tandem mass spectrometry (LC-ESI-MS) and high performance liquid chromatography (HPLC) using a Waters (Milford, Mass.) LC-MS system. For LC-ESI-MS analyses, a Waters XTerra® C18 5 µm column was used. For preparative runs, an Atlantis® Prep T3 OBD™ 5 µM or an XTerra® Prep MS C18 OBD™ 5 µM column was used. High-resolution electrospray ionization mass spectrometry (HRMS-ESI) was performed using a Bruker Daltonics APEXIV 4.7 Tesla Fourier Transform mass spectrometer (FT-ICR-MS) in the Department of Chemistry Instrumentation Facility at Massachusetts Institute of Technology. The yield was 29% (3.0 mg, 1.7 µmol). Characterization by LC-ESI-MS and HRMS-ESI resulted in the following values:

Daptomycin-TCO: LC-ESI-MS (−) m/z=1770.8 $[M-H^+]^-$; LC-ESI-MS (+) m/z=1773.0 $[M+H^+]^+$; HRMS-ESI $[M+H]^+$ m/z calculated for $[C_{81}H_{113}N_{17}O_{28}]^+$ 1772.8019. found 1772.7970.

2. Bacterial Nanoparticle Detection Via Daptomycin Cycloaddition

Daptomycin-TCO was used to magnetically label bacteria using methods similar to those described in Example 1.

Figure 10:
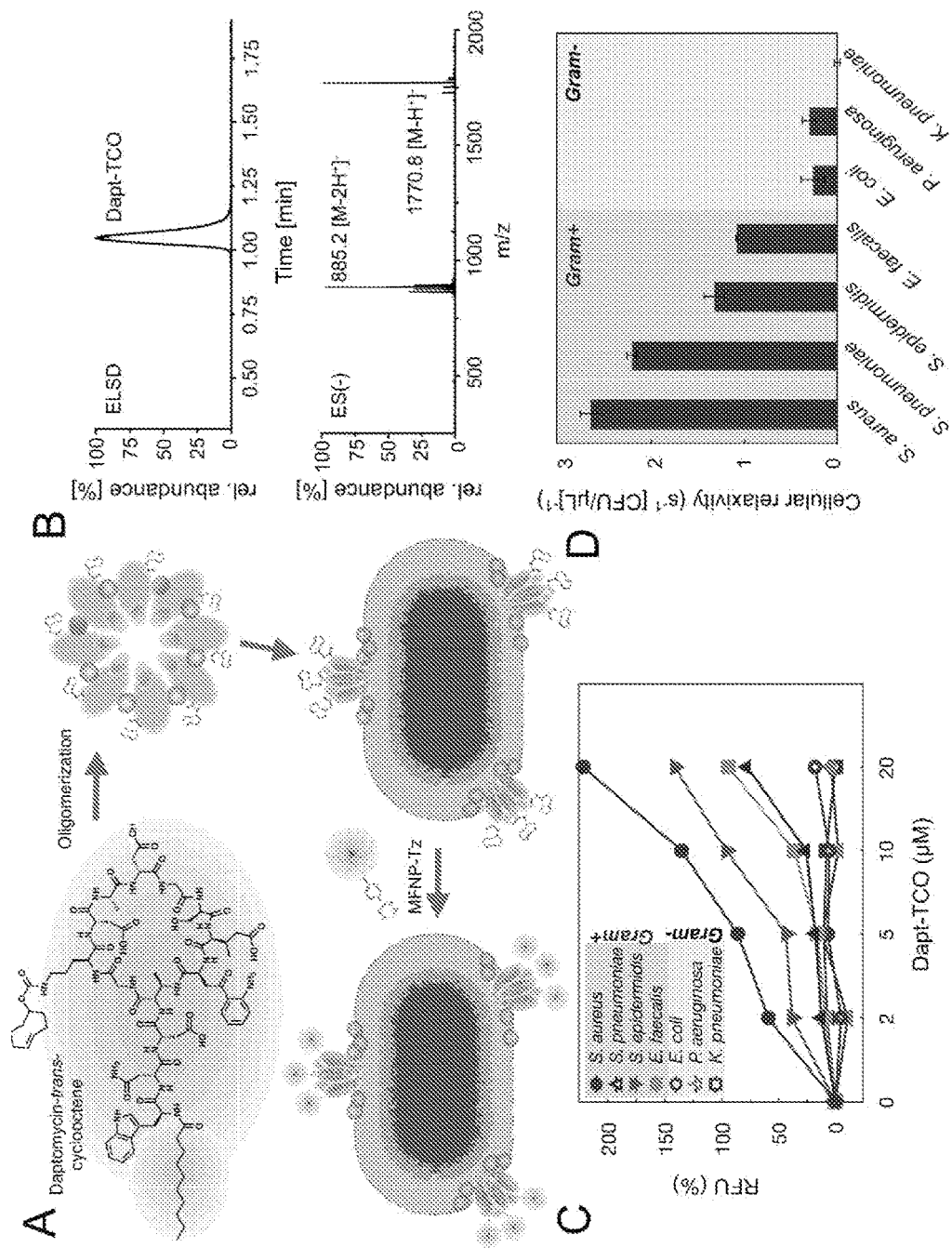
FIG. 10 depicts the use of daptomycin-trans-cyclooctene (daptomycin-TCO) for bacterial detection showing (A) the binding mechanism of daptomycin-TCO to Gram-positive bacteria; (B) HPLC and ESI-MS traces of daptomycin-TCO; (C) the detection of MFNP-labeled bacteria by fluorescence spectrometry at various concentrations of daptomycin-TCO and (D) the detection of MFNP-labeled bacteria by magnetic resonance.

FIG. 10A depicts the binding mechanism of daptomycin-TCO (dapt-TCO) to the bacterial cell wall. In the presence of $Ca^{2+}$, daptomycin-TCO oligomerizes and binds to the bacterial cell wall, which then causes the formation of membrane pores and consequent depolarization.

FIG. 10B depicts HPLC and ESI-MS traces of daptomycin-TCO prepared as described above.

FIG. 10C shows the detection of MFNP-labeled bacteria by fluorescence spectrometry at various concentrations of daptomycin-TCO (data expressed as mean±standard deviation). The result shows that complementary application of daptomycin-TCO and MFNP-Tz resulted in highly specific labeling of Gram-positive bacteria, with increased relative fluorescence intensities of up to 220%.

FIG. 10D shows the detection of MFNP-labeled bacteria by magnetic resonance (data expressed as mean±standard error). The result confirms that the complementary application of daptomycin-TCO and MFNP-Tz resulted in highly specific labeling of Gram-positive bacteria, with cellular relaxivity of 1.32 $s^{-1}[CFU/\mu L]^{-1}$.

Example 3. Magnetic Labeling Of Bacteria Using a Crystal Violet-Trans-Cyclooctene Conjugate The Example below describes labeling bacteria using trans-cyclooctene (TCO) conjugates of Crystal violet, to discriminate Gram-positive from Gram-negative bacteria.

1. Chemical Synthesis

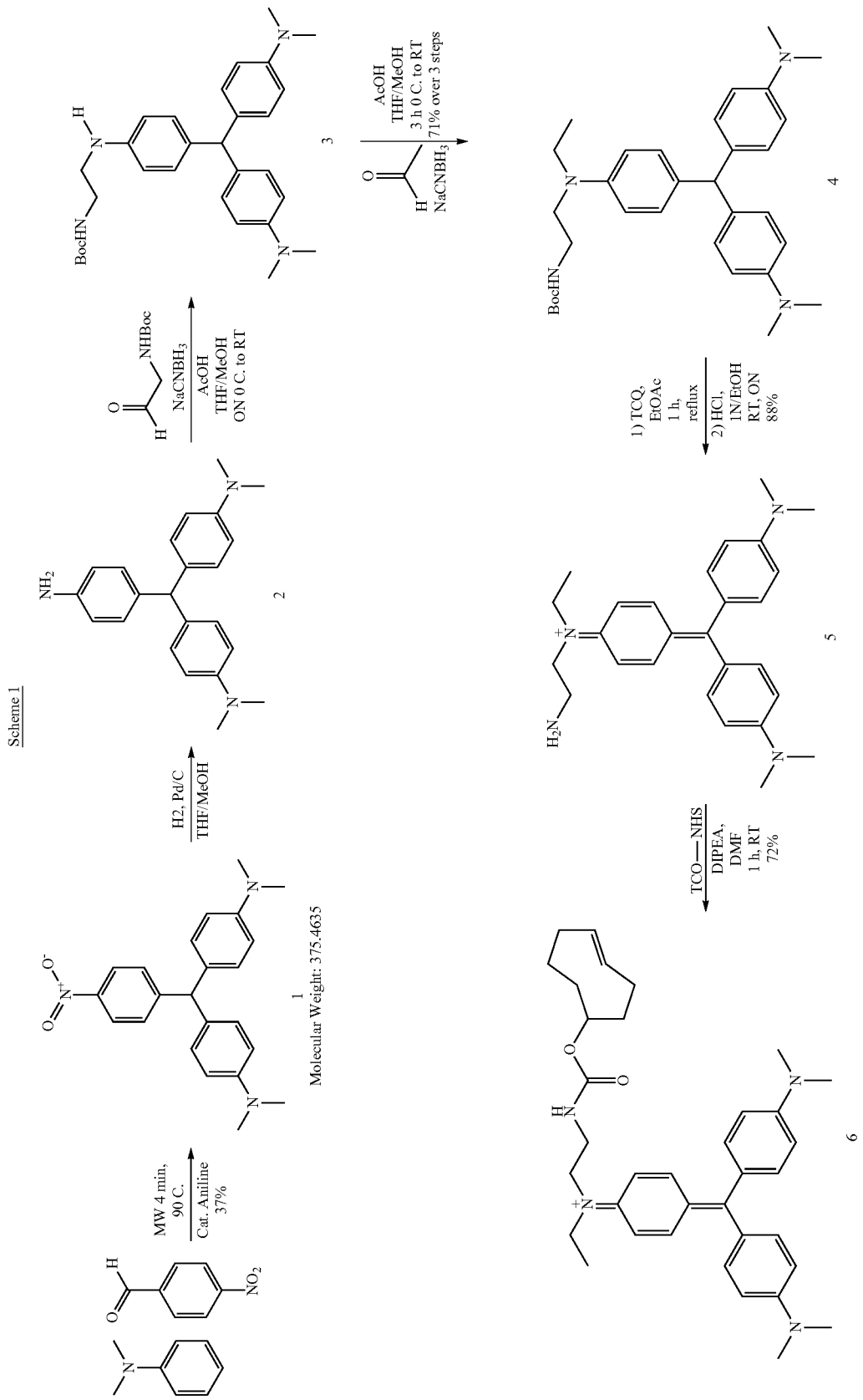
Scheme 1

4,4'-((4-Nitrophenyl)methylene)bis(N,N-dimethylaniline)

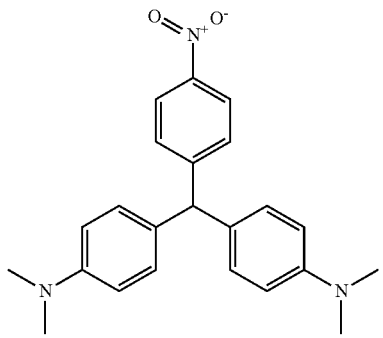

N,N'-Dimethylaniline (922 µL, 7.28 mmol), 4-nitrobenzaldehyde (500 mg, 3.31 mmol) and aniline (50 mg, 386 mmol, 10% w/w) were mixed thoroughly in a 10 mL open Pyrex tube containing a Teflon-coated stirring bar. The mixture was irradiated during 4 min in a microwave oven at power 100 W at 90° C. The reaction mixture was purified by silica gel flash chromatography column (hexane/EtOAc, 90/10) and further purified by recrystallization in hexane/EtOAc. Crystals were filtrated and washed with cold hexane giving 4,4'-((4-Nitrophenyl)methylene)bis(N,N-dimethylaniline) (585 mg, 47%) as golden solid. $^1$H NMR (400 MHz, cdcl$_3$) δ 8.12 (d, J=8.6 Hz, 2H), 7.31 (d, J=8.7 Hz, 2H), 6.96 (d, J=8.6 Hz, 4H), 6.69 (d, J=8.5 Hz, 4H), 5.46 (s, 1H), 2.94 (s, 12H). $^{13}$C NMR (101 MHz, cdcl$_3$) δ 153.58, 149.34, 149.32, 146.31, 130.20, 129.97, 123.49, 112.70, 55.05, 40.75. HRMS: [M+H]$^+$ m/z calc. 376.2020 for $C_{23}H_{26}N_3O_2$, found 376.2011.

4,4'-((4-aminophenyl)methylene)bis(N,N-dimethylaniline)

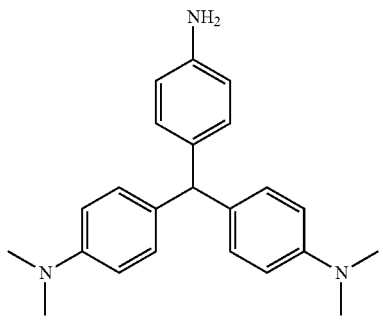

A two neck round bottom flask was charged with 4,4'-((4-Nitrophenyl)methylene)bis(N,N-dimethylaniline) (100 mg, 0.266 mmol). A nitrogen line was connected to the flask via a syringe needle inserted through one of the septa. A line connected to a second septum via a syringe needle led to an oil-filled bubbler. Nitrogen flow was started and the flask was purged with dry nitrogen. A degassed mixture of dry MeOH/THF 1/2 (3 mL) was added. Pd/C 10% (10 mg) was added and the mixture was further degassed by purging with nitrogen for 10 min. The nitrogen flow was stopped and hydrogen was introduced. The mixture was then stirred under hydrogen for 4 h at room temperature. Complete and clean conversion was detected by HPLC-MS and TLC affording 4,4'-((4-aminophenyl)methylene)bis(N,N-dimethylaniline).

tert-butyl (2-(4-(bis(4-(dimethylamino)phenyl)methyl)phenyl)amino)ethyl)carbamate

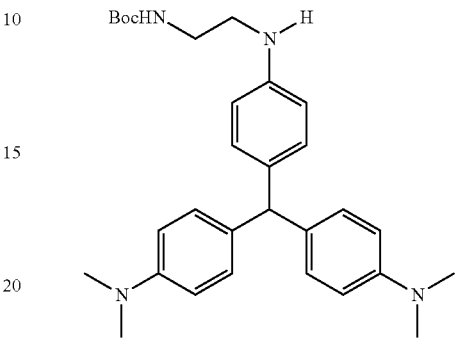

The flask was then purged with nitrogen and cooled in an ice bath. N-Boc-2-aminoacetaldehyde (55 mg, 0.346 mmol), sodium cyanoborohydride (22 mg, 0.346 mmol) and acetic acid (20 µL, 0.346) were added to the reaction mixture. After stirring at room temperature overnight with nitrogen flow, an aliquot was examined by TLC and HPLC-MS showing that the starting material had been cleanly converted into the monoalkylated aniline tert-butyl (2-((4-(bis(4-(dimethylamino)phenyl)methyl)phenyl)amino)ethyl)carbamate.

tert-butyl (2-((4-(bis(4-(dimethylamino)phenyl)methyl)phenyl)(ethyl)amino)ethyl)carbamate

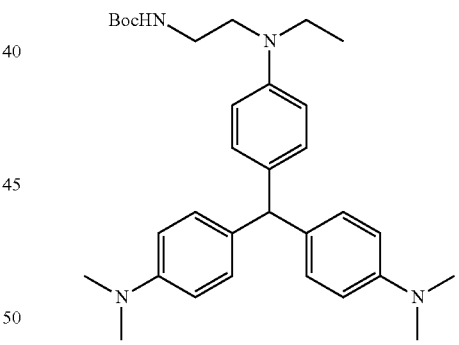

While stirring under nitrogen flow, the reaction mixture was cooled in an ice bath. Acetaldehyde (30 mL, 0.798 mmol), sodium cyanoborohydride (50 mg, 0.798 mmol) and acetic acid (45 mL, 0.798 mmol) were added and the reaction was stirred at room temperature for 5 h. An aliquot was examined by TLC and HPLC-MS showing that the starting material had been cleanly converted into the dialkylated aniline. The reaction mixture was then filtrated on diatomaceous earth and washed with MeOH and concentrated. The residue was diluted with water and extracted twice with DCM. Organics were combined and washed with water, dried over MgSO$_4$, filtered and evaporated under reduced pressure and the resulting residue purified by column chromatography (5 to 30% EtOAc/hexanes) affording tert-butyl (2-((4-(bis(4-(dimethylamino)phenyl)methyl)phenyl)(ethyl)amino)ethyl)carbamate (97 mg, 71% over three steps) as a light purple powder. $^1$H NMR (400 MHz, CDCl$_3$) δ 7.02 (d, J=8.6 Hz, 4H), 6.99 (d, J=8.7 Hz, 2H), 6.69 (d, J=8.5 Hz, 4H), 6.65 (d, J=8.6 Hz, 2H), 5.30 (s, 1H), 4.77 (s, 1H), 3.35 (dd, J=14.1, 6.9 Hz, 2H), 3.31-3.22 (m, 4H), 2.92 (s, 12H), 1.47 (s, 9H), 1.14 (t, J=7.0 Hz, 3H). $^{13}$C NMR (101 MHz, CDCl$_3$) δ 156.12, 148.92, 146.09, 133.80, 133.32, 130.20, 129.95, 112.67, 112.25, 79.31, 54.11, 50.00, 45.51, 40.91, 38.60, 28.52, 12.32. HRMS: [M+H]$^+$ m/z calc. 517.3537 for C$_{32}$H$_{45}$N$_4$O$_2$. found 517.3530.

2-amino-N-(4-(bis(4-(dimethylamino)phenyl)methylene)cyclohexa-2,5-dien-1-ylidene)-N-ethylethanaminium chloride

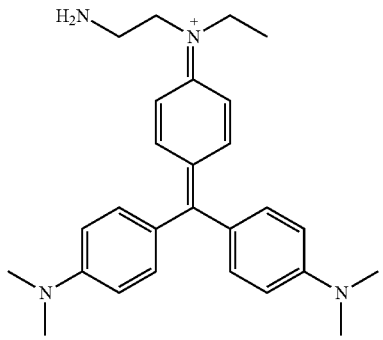

tert-butyl (2-((4-(bis(4-(dimethylamino)phenyl)methyl)phenyl)(ethyl)amino)ethyl)carbamate (10 mg, 0.019 mmol) was dissolved EtOAc (3 mL) and tetrachloroquinone (7.1 mg, 0.029 mmol) was added. The solution was stirred at 78° C. for 1 h causing the formation of an intense blue indicating the formation of the cationic dye. A 1N HCl (2 mL) solution was then added and the mixture was stirred at room temperature overnight. The reaction mixture was diluted with water and washed four times with EtOAc. The aqueous layer was evaporated under reduced pressure and the resulting residue purified by column chromatography on neutral alumina (10 to 30% MeOH/DCM) affording 2-amino-N-(4-(bis(4-(dimethylamino)phenyl)methylene)cyclohexa-2,5-dien-1-ylidene)-N-ethylethanaminium chloride (12 mg, 88%) as an intense green violet powder. $^1$H NMR (400 MHz, cd$_3$od) δ 7.42-7.35 (m, 6H), 7.07 (d, J=8.3 Hz, 2H), 7.00 (d, J=8.5 Hz, 4H), 3.87 (t, J=6.3 Hz, 2H), 3.68 (dd, J=12.6, 5.9 Hz, 2H), 3.27 (s, 12H), 3.25-3.21 (m, 2H), 1.29 (t, J=6.2 Hz, 3H). $^{13}$C NMR (101 MHz, cd$_3$od) δ 179.85 (s), 157.54 (s), 154.87 (s), 141.19 (s), 140.76 (s), 128.73 (s), 128.08 (s), 113.93 (s), 113.67 (s), 48.43 (s), 46.88 (s), 40.85 (s), 38.09 (s), 12.44 (s). HRMS: [M]$^+$ m/z calc. 415.2856 for C$_{27}$H$_{35}$N$_4$. found 415.2857.

(E)-N-(4-(bis(4-(dimethylamino)phenyl)methylene)cyclohexa-2,5-dien-1-ylidene)-2-(((cyclooct-4-en-1-yloxy)carbonyl)amino)-N-ethylethanaminium chloride (Crystal Violet-TCO/CV-TCO)

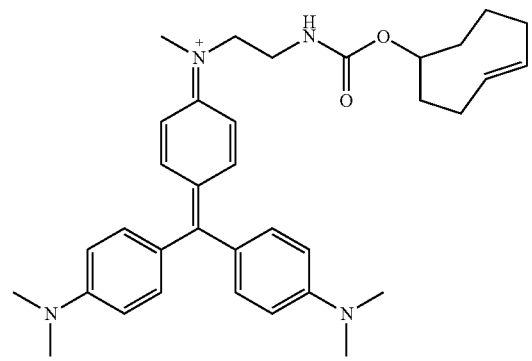

2-Amino-N-(4-(bis(4-(dimethylamino)phenyl)methylene)cyclohexa-2,5-dien-1-ylidene)-N-ethylethanaminium chloride (1.75 mg, 3.9 μmol), TCO—NHS (1.55 mg, 5.8 μmol) and DIPEA (2 μL, 11.7 μmol) were dissolved in 55 μL DMF and stirred overnight at room temperature. The mixture was purified by HPLC affording (E)-N-(4-(bis(4-(dimethylamino)phenyl)methylene)cyclohexa-2,5-dien-1-ylidene)-2-(((cyclooct-4-en-1-yloxy)carbonyl)amino)-N-ethylethanaminium chloride (1.6 mg, 72%) as a green violet powder. HRMS: [M]$^+$ m/z calc. 567.3694 for C$_{32}$H$_{45}$N$_4$O$_2$. found 567.3685.

Figure 11:
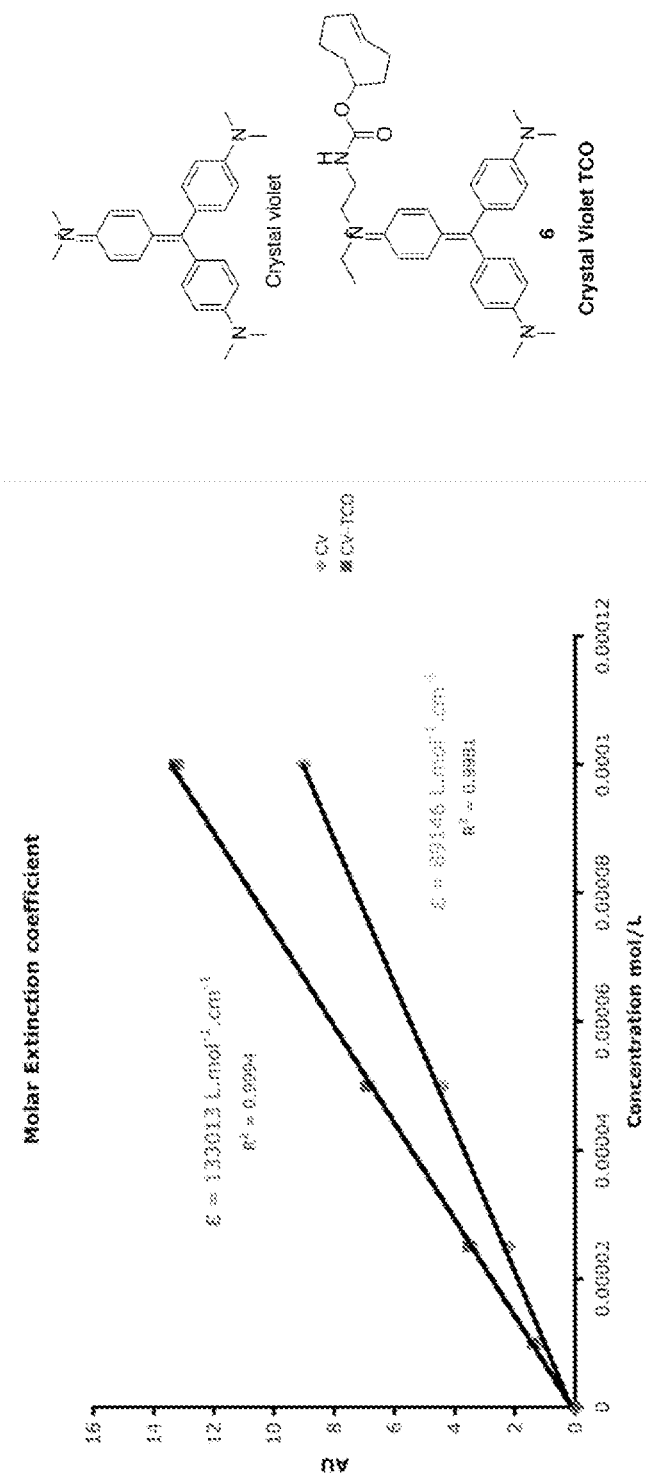
FIG. 11 shows a comparison of the molecular structures and molar extinction coefficients of Crystal Violet and Crystal Violet-TCO.

The molar extinction coefficient of Crystal Violet-TCO was ε$_{592}$=133013 L·mol$^{-1}$·cm$^{-1}$ as compared to unmodified crystal violet that had ε$_{592}$=89146 L·mol$^{-1}$·cm$^{-1}$. FIG. 11 shows a comparison of the molecular structures and molar extinction coefficients of Crystal Violet and Crystal Violet-TCO.

2. Preparation of Bioorthogonal Nanoparticles

Magnetofluorescent nanoparticles (MFNPs) were synthesized as reported by Josephson et al. *Bioconjugate Chem.* 1999, 10, 186-191. The nanoparticles had a shell of cross-linked dextran and core of (Fe$_2$O$_3$)$_m$(Fe$_3$O$_4$)$_n$ (diameter 3 nm). The hydrodynamic diameter had an average value of 21 nm, with each particle having 22 free amine groups and 8.4 molecules of fluorescein molecules conjugated on the surface. The r$_1$ and r$_2$ relaxivity values were 23 s$^{-1}$ mM$^{-1}$ [Fe] and 51 s$^{-1}$ mM$^{-1}$ [Fe] as measured, respectively.

Amine-reactive tetrazine (Tz-NHS) was prepared as described by Haun et al., *Nat. Nanotechnol,* 2010, 5, 660-665 Tetrazine-conjugated magnetofluorescent nanoparticles (MFNP-Tz) were prepared by adding MFNPs in phosphate buffered saline solution (PBS) containing 10 mM sodium bicarbonate, with 500 times molar excess of Tz-NHS dissolved in dimethylsulfoxide (DMSO, 1:9 volume), and allowed to react at room temperature for 4 h. Unreacted Tz-NHS was removed using Sephadex G-50 (GE Healthcare). The amount of conjugated tetrazine was quantified by reacting the MFNPs with succinimidyl 3-(2-pyridyldithio) propionate (SPDP), followed by treatment with dithiothreitol (DTT), and measuring the absorbance at 343 nm for traces of the cleaved pyridine-2-thione product. For MFNPs, which have a core of ~2 nm and a hydrodynamic diameter ($D_h$) of ~21 nm, 20 out of 22 amine groups per particle were conjugated with tetrazine molecules.

Tetrazine-conjugated gold nanoparticles (GNP-Tz) were prepared by reacting amine-functionalized gold nanoparticles (NANOCS, 10 nm core) with 1000 times molar excess of Tz-NHS in 1:9 DMSO/0.2×PBS solution at room temperature for 4 h, and washed three times with deionized water using Amicon (Millipore, MWCO 100,000). For GNPs having a core size of 10 nm, 2520 among a total of 3120 amine groups per particle were converted to tetrazine.

3. Bacterial Cultures

Bacterial strains *Staphylococcus aureus* (*S. aureus;* #25923), *Staphylococcus epidermidis* (*S. epidermidis;* #29886), *Bacillus subtilis* (*B. subtilis;* #82), *Streptococcus pneumoniae* (*S. pneumoniae;* #6318), *Enterococcus faecalis* (*E. faecalis;* #29212), *Escherichia coli* (*E. coli;* #25922), *Pseudomonas aeruginosa* (*P. aeruginosa;* #142), *Klebsiella pneumoniae* (*K. pneumoniae;* #43816), *Enterobacter aerogenes* (*E. aerogenes;* #13048), and *Citrobacter freundii* (*C. freundii;* #6879) were purchased from ATCC (Manassas, Va.). For selective culture, *S. aureus* and *S. epidermidis* were plated in mannitol salt agar (BD Biosciences, Sparks, Md.) and colonies were cultured in *Staphylococcus* broth (BD Biosciences) for growth overnight. *S. pneumoniae* was plated onto selective *streptococcus* agar and the colony was seeded into Tryptic Soy Broth containing 5% defibrinated sheep blood (Hemostat Laboratories, Dixon, Calif.) for growth. *P. aeruginosa* was plated on *Pseudomonas* isolation agar, and *E. faecalis, E. coli*, and *K. pneumoniae* were plated onto standard agar plates. For growth, *P. aeruginosa* and *K. pneumoniae* were cultured in Tryptic Soy Broth, *E. faecalis* was cultured in Tryptic Soy Broth containing 5% defibrinated sheep blood, and *E. coli* was cultured in Luria-Bertani (LB) media (BD Biosciences). Bacterial cell numbers were determined by plating onto standard agar plates and counting the number of colony forming units (CFU), and by comparison to optical density measurements, conversion factors were obtained.

4. Gram Staining

Bacterial cells were smeared onto microscopic slides, and stained with standard crystal violet (20 mM) or CV-TCO (1 mM) in 20% ethanol solution containing 8 mg/ml ammonium oxalate for 3 min. After washing with deionized water, slides were treated with Gram Iodine (BD Biosciences), decolorized with 95% ethanol solution, and counterstained with Gram safranin (BD Biosciences). Slides were observed using a bright field light microscope.

5. Bacterial Labeling with Nanoparticles

Bacterial cells in media were first washed with phosphate buffered saline solution (PBS). For μNMR measurements, absorbance measurements, confocal microscopy, and transmission electron microscopy (TEM), the bacteria ($10^8$ in 100 μl) were stained with 200 μM CV-TCO in 20% ethanol solution containing 8 mg/ml ammonium oxalate for 5 min. at room temperature, and washed with PBS. Then the bacteria were treated with Gram Iodine solution for 1 min. and decolorized with 95% ethanol solution. For μNMR and confocal microscopy, bacteria were incubated with 50 μg/ml MFNP-Tz in PBS for 20 min. at room temperature, and washed twice with PBS. For confocal microscopy, labeled bacteria were mounted on microscopic slides with Vectashield containing propium iodide (Vector Laboratories), and imaged. For TEM, the stained and decolorized bacteria were incubated with 50 μg/ml GNP-Tz in PBS for 1 h, washed with PBS, and dehydrated with graded ethanol series before applying onto a carbon grid (Ted Pella).

8. Results a. Gram-Staining Using Crystal Violet-TCO

To test the efficacy of Crystal Violet-TCO as a staining agent for Gram-positive bacteria, three representative samples were prepared: *Staphylococcus aureus* (*S. aureus;* Gram-positive), *Escherichia coli* (*E. coli;* Gram-negative), and the mixture of both bacterial species. Bacterial smears on glass slides were stained with a solution of Crystal Violet-TCO (1 mM) or Crystal Violet for 3 min., followed by treatment with Gram's iodine solution for one minute, decolorization with 95% ethanol, and counterstaining with red Safranin solution. The results are shown in FIGS. 12A and 12B.

Figure 12:
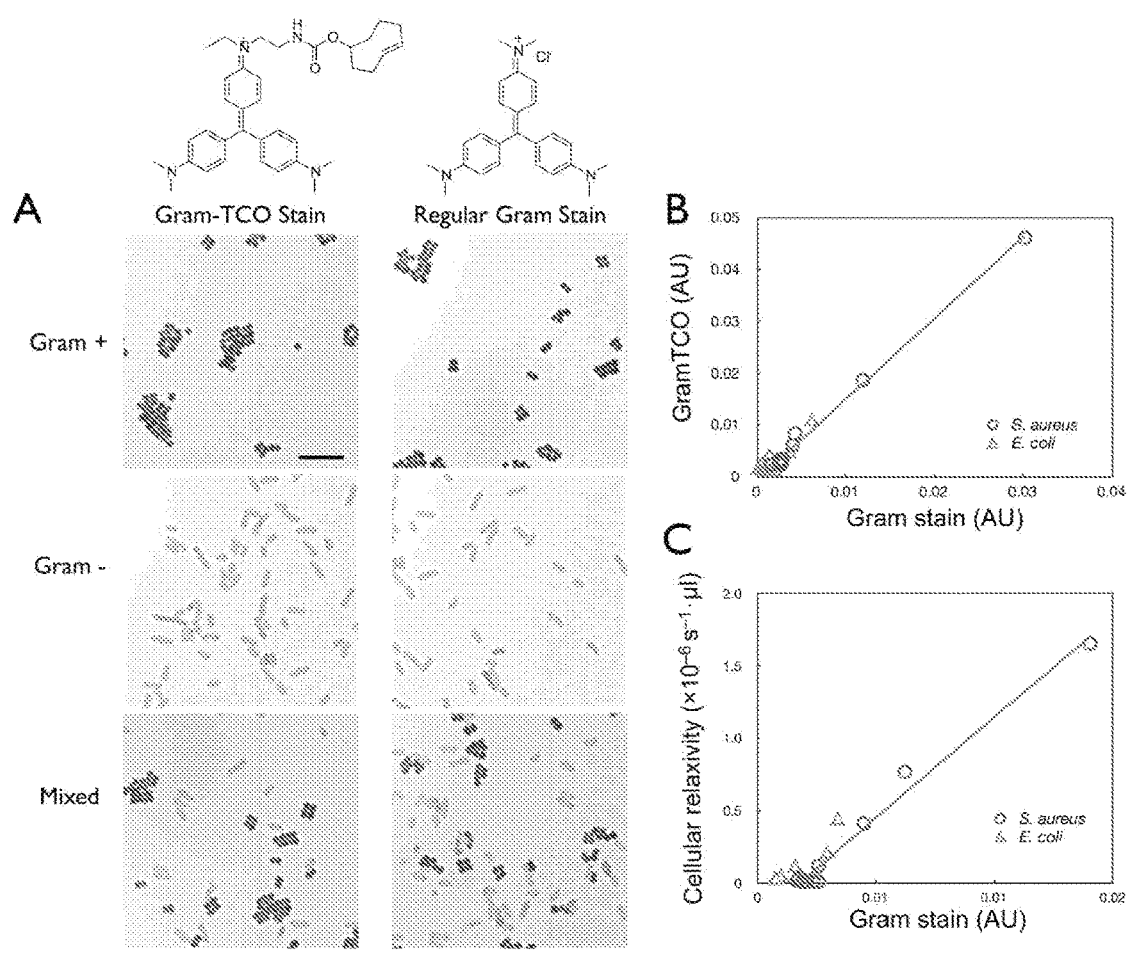
FIG. 12 shows (A) Gram staining of S. aureus (Gram-positive), E. coli (Gram-negative), and mixture of S. aureus and E. coli stained with Crystal violet-TCO (left panels) or with Crystal violet (right panels); (B) the correlation of absorbance at 595 nm between bacteria stained with Crystal violet and Crystal violet-TCO; and (C) the correlation between absorbance (595 nm) and magnetic relaxivity values of bacterial cells stained with Crystal violet-TCO and labeled with magnetic MFNP-Tz.

FIG. 12 shows Gram staining of *S. aureus* (Gram-positive cocci), *E. coli* (Gram-negative bacilli), and mixture of *S. aureus* and *E. coli* stained with Crystal violet-TCO (left panels) or with Crystal violet (right panels) (scale bar=10 mm).

FIG. 12 shows the correlation between absorbance at 595 nm for bacteria stained with Crystal violet or with Crystal violet-TCO.

Microscopy revealed that only Gram-positive *S. aureus* remained purple, while Gram-negative *E. coli* was decolorized due to dissolution of the outer membrane (FIG. 3A). Importantly, there was excellent correlation between Crystal Violet and Crystal Violet-TCO staining ($r^2>0.99$; FIG. 3B).

Figure 13:
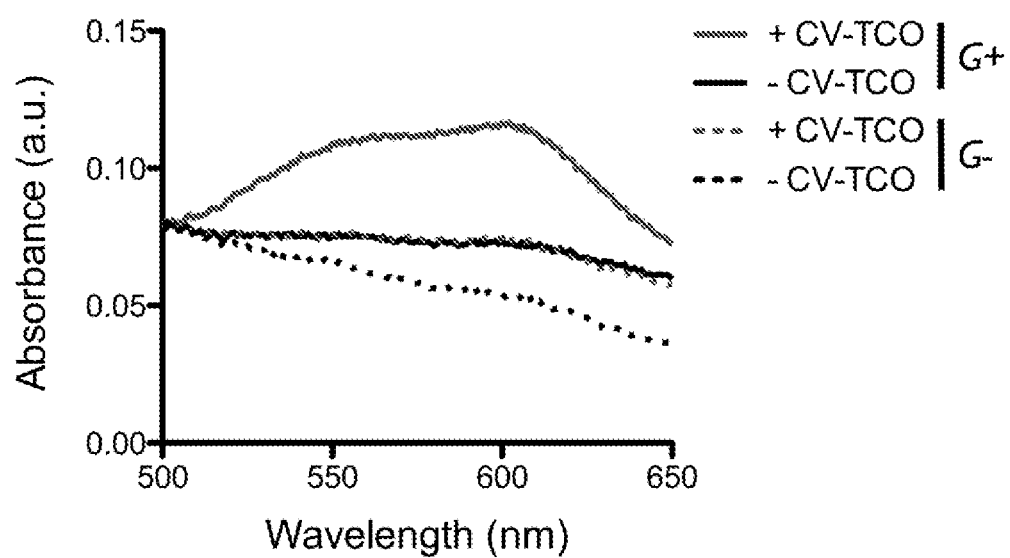
FIG. 13 shows UV absorbance spectra of Gram-positive (S. aureus, G+) and Gram-negative (E. coli, G−) stained with (+CV-TCO) or without (−CV-TCO) crystal violet-TCO.

The specificity of CV-TCO was further confirmed by UV-visible spectrometry, the results of which are shown in FIG. 13. FIG. 13 shows UV absorbance spectra of Gram-positive (*S. aureus*, G+) and Gram-negative (*E. coli*, G−) stained with (+CV-TCO) or without (−CV-TCO) Crystal Violet-TCO. The results show that only Gram-positive bacteria showed an intense absorption at 595 nm.

In addition, FIG. 12C shows a correlation between absorbance (595 nm) and magnetic relaxivity values of bacterial cells stained with Crystal violet-TCO and labeled with magnetic MFNP-Tz. See below.

b. Magnetic Labeling Using Crystal Violet-TCO

To test whether bacteria labelled with Crystal Violet-TCO could be magnetically labeled via cycloaddition to the TCO group, bacteria stained with Crystal Violet-TCO were incubated with magnetofluorescent nanoparticles modified with tetrazine (MFNP-Tz). Control samples were prepared by incubating unstained bacteria with MFNP-Tz. The $T_2$ relaxation values of samples were measured using a miniaturized μNMR system. For comparative analyses, the absorption (at 595 nm) of the same samples was also measured. Cellular relaxivity ($r_2$) was obtained by normalizing the measured $1/T_2$ values with bacterial concentration, and the $r_2$ differences ($\Delta r_2$) between targeted and control samples were calculated. As shown in FIG. 12C, a strong correlation ($r^2>0.9$) between the extent of Gram-staining and the cellular relaxivity in Gram-positive species was observed, confirming that that Crystal Violet-TCO on the bacterial surface was accessible for reaction with MFNP-Tz.

Figure 14:
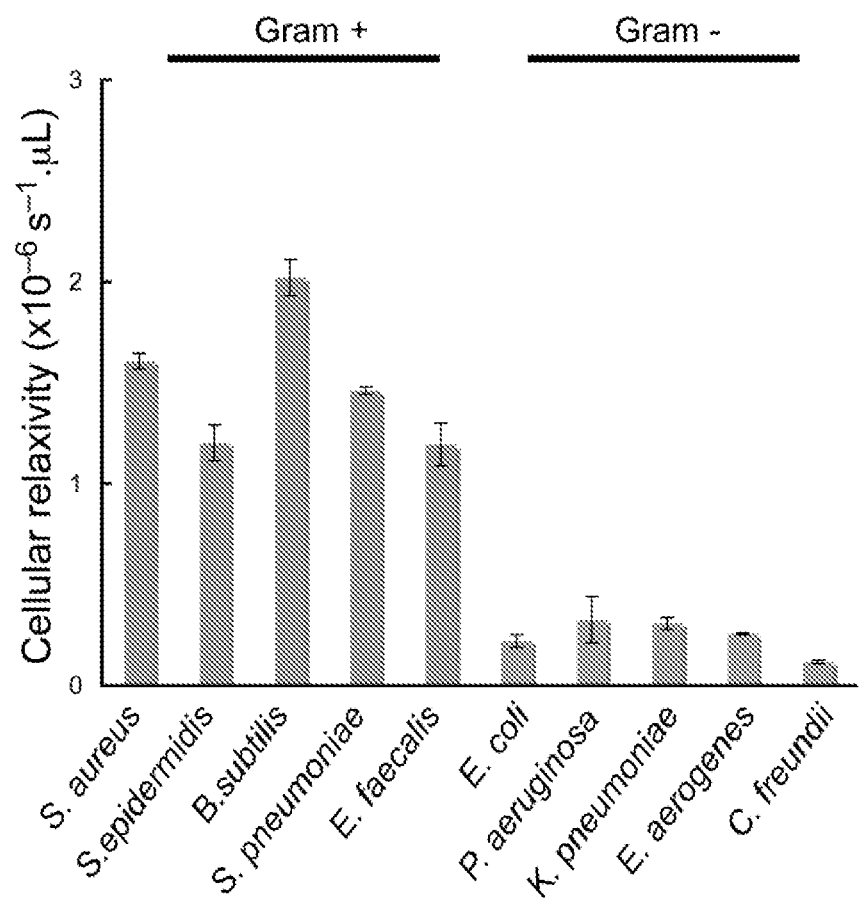
FIG. 14 shows the results of magnetic detection of different species of Gram-positive and Gram-negative bacteria labeled using crystal violet-TCO and MFNP-Tz by μNMR.

The labeling strategy was further applied to a panel of different bacterial species. The results are shown in FIG. 14. FIG. 14 shows the cellular relaxivity for various Gram-positive and Gram-negative bacteria labelled with Crystal Violet-TCO and MFNP-Tz, as measured by μNMR. The results showed that all Gram-positive species tested showed significantly higher cellular relaxivity values when compared to Gram-negative bacteria. Such magnetic labeling enabled the performance of highly sensitive and rapid detection of Gram-positive bacteria.

Figure 15:
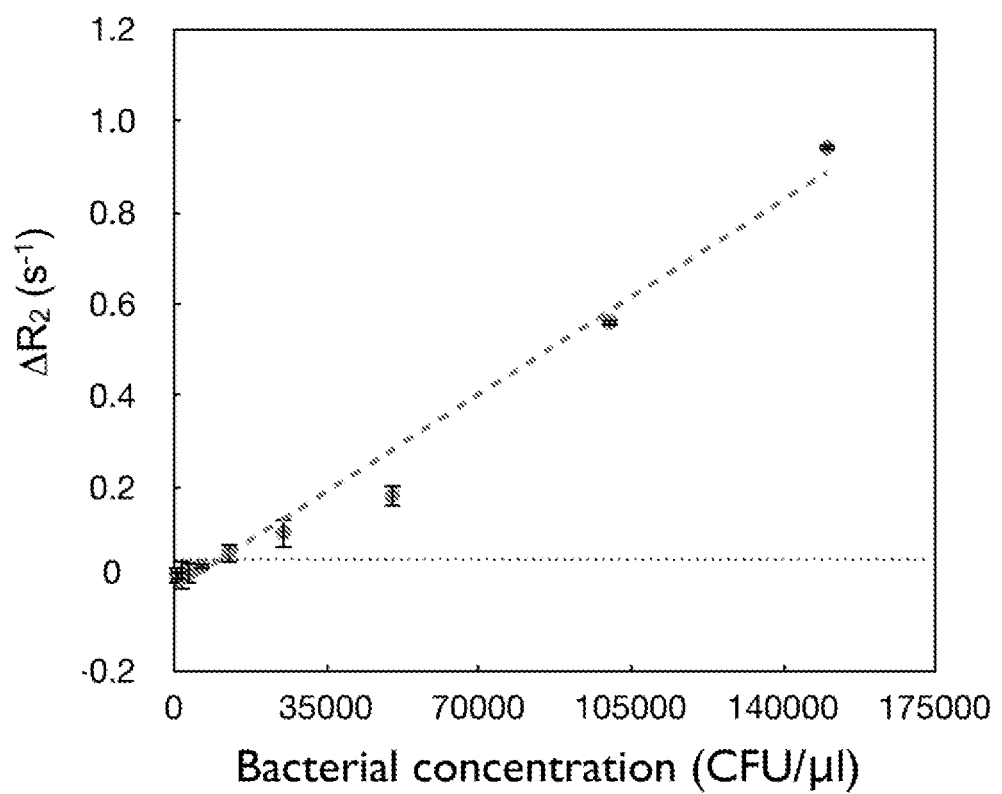
FIG. 15 depicts an experiment to measure the sensitivity of labeling using crystal violet-TCO.

To measure the sensitivity of the assay, measurements with serially diluted bacterial samples were performed and established a detection limit of about 4,000 bacteria with the experimental set-up used. The results are shown in FIG. 15, which shows sensitivity of labeling. $\Delta R_2$ values calculated by subtracting values of Gram-+ bacteria (*S. aureus*) non-specifically bound with MFNP-Tz from ones that were specifically targeted (treated with Crystal Violet-TCO and MFNP-Tz). Dotted line shows threshold of detection. Limit of detection was ~4000 CFU.

It is predicted, however, that the detection threshold can, be improved to single cell levels by further miniaturization or the use of alternative sensors.

Figure 16:
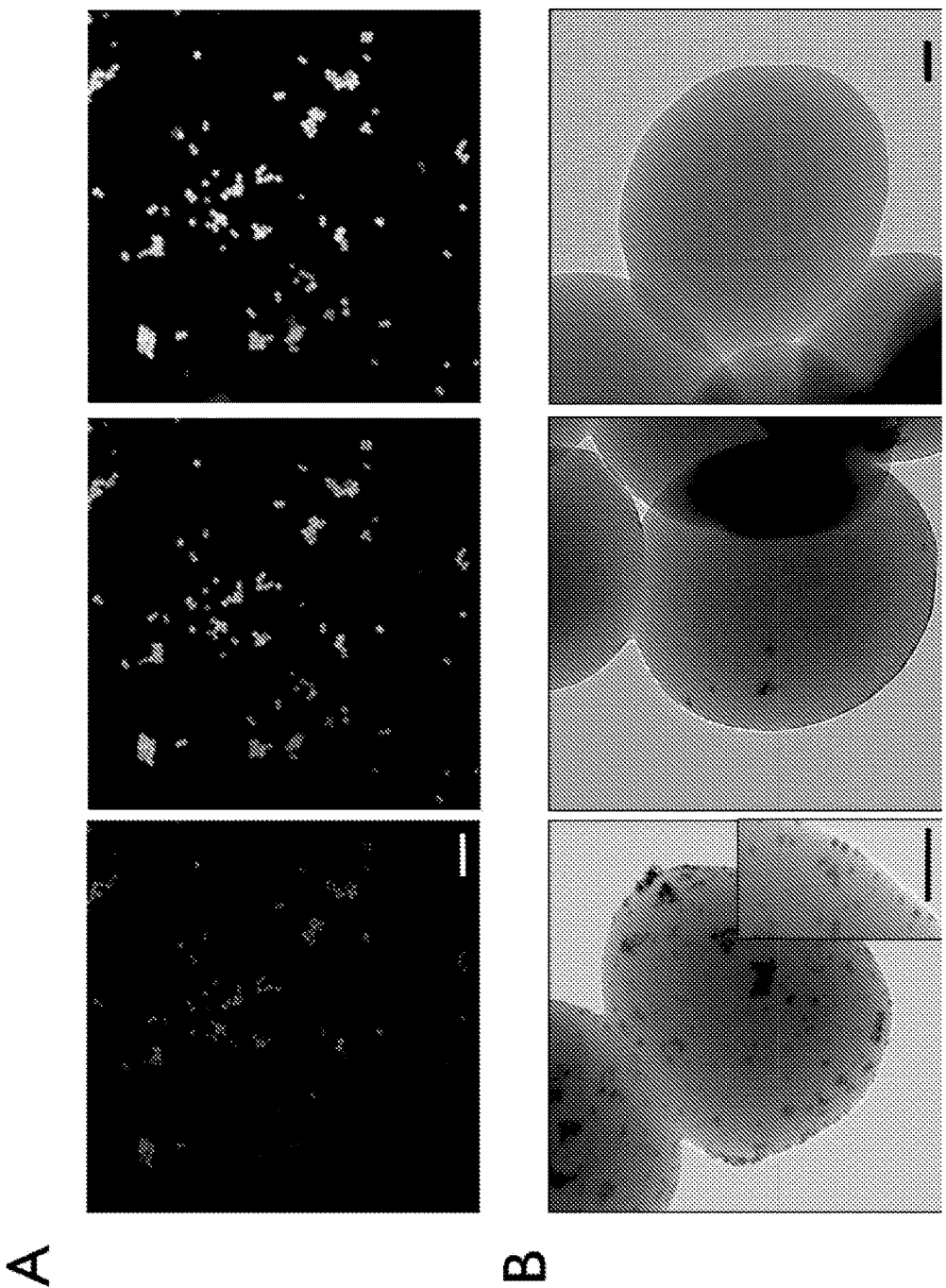
FIG. 16 shows (A) fluorescence confocal microscopy of S. aureus stained with crystal violet-TCO and labeled with MFNP-Tz; and (B) transmission electron microscopy of S. aureus stained with Crystal violet-TCO and labeled with GNP-Tz (left), GNP-Tz alone (middle), or without any treatment (right).

Bioorthogonally labeled bacteria were also analyzed by confocal microscopy and electron microscopy. The results are shown in FIG. 16.

FIG. 16A shows the results of fluorescence confocal microscopy of *S. aureus* stained with Crystal Violet-TCO and labeled with MFNP-Tz. The left, middle, and right panels show images of the red channel, green channel, and a merged image of the red and green channels, respectively (Red: propidium iodide for nuclear staining; Green: MNFP-Tz staining; Scale bar=10 µm).

FIG. 16B shows the result of transmission electron microscopy of *S. aureus* stained with Crystal Violet-TCO and labeled with GNP-Tz (left), GNP-Tz alone (middle), and without any treatment (right) (Scale bar=100 nm) (GNP-Tz=Tetrazine-conjugated gold nanoparticles). Gold nanoparticles were used instead of magnetic nanoparticles to obtain higher contrast.

Figure 17:
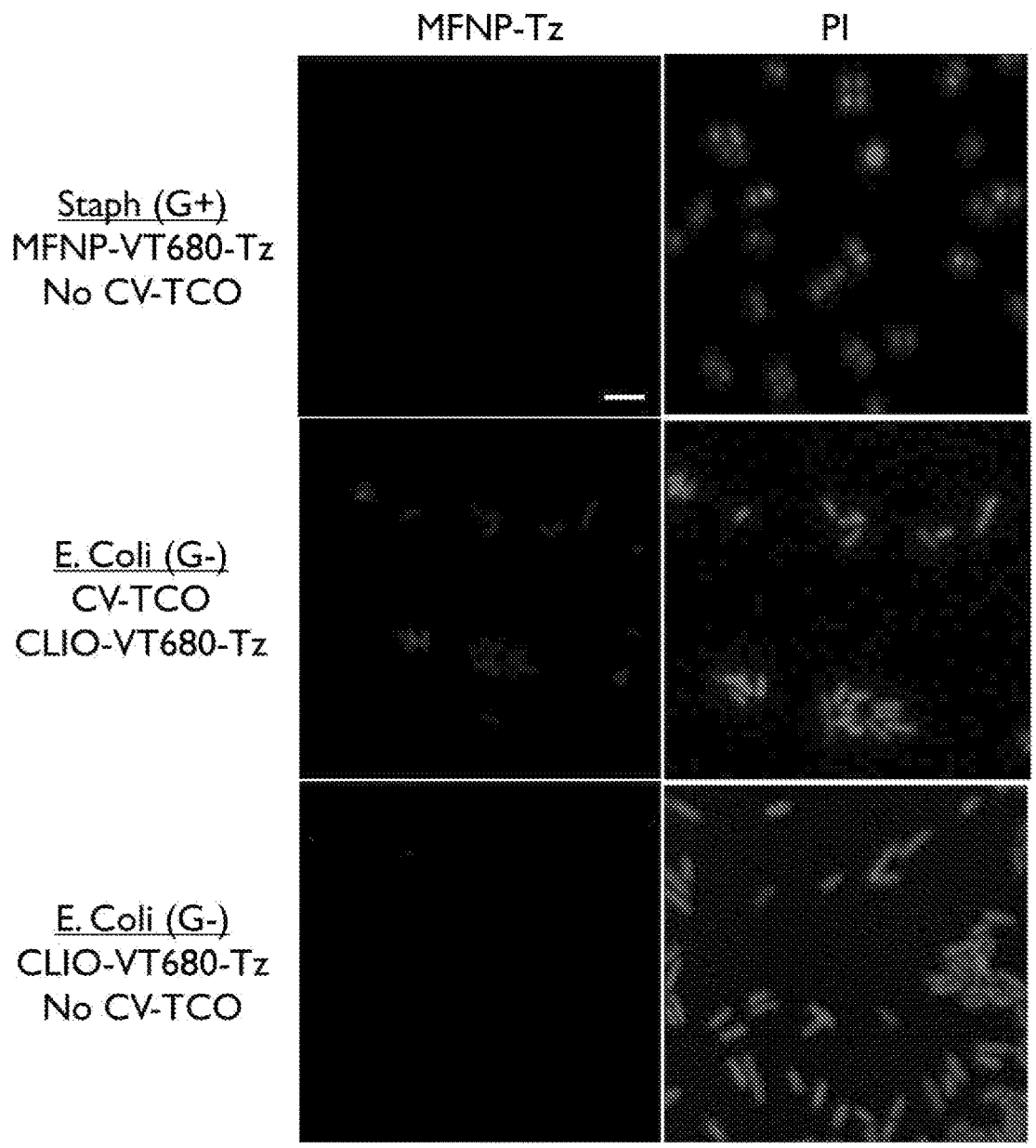
FIG. 17 shows the confocal microscopy for control experiments: S. aureus (Gram-positive) labeled with MFNP-Tz alone (top), E. coli (Gram-negative) stained with CV-TCO and labeled with MNFP-Tz (middle) E. coli labeled with MFNP-Tz alone (bottom) (propidium iodide for nuclear staining; red (left), MNFP-Tz; green (right)).

The results of control experiments are shown in FIG. 17. FIG. 17 shows confocal microscopy for control experiments in which *S. aureus* (Gram-positive) was labeled with MFNP-Tz alone (top), *E. coli* (Gram-negative) was stained with Crystal Violet-TCO and labeled with MNFP-Tz (middle) and *E. coli* labeled with MFNP-Tz alone (bottom), with propidium iodide used for nuclear staining. The green channel (left) indicates MNFP-Tz, and the red channel (right) indicates propidium iodide. (Scale bar=5 µm). The control experiments all showed an absence of MFNP-Tz signal.

Figure 18:
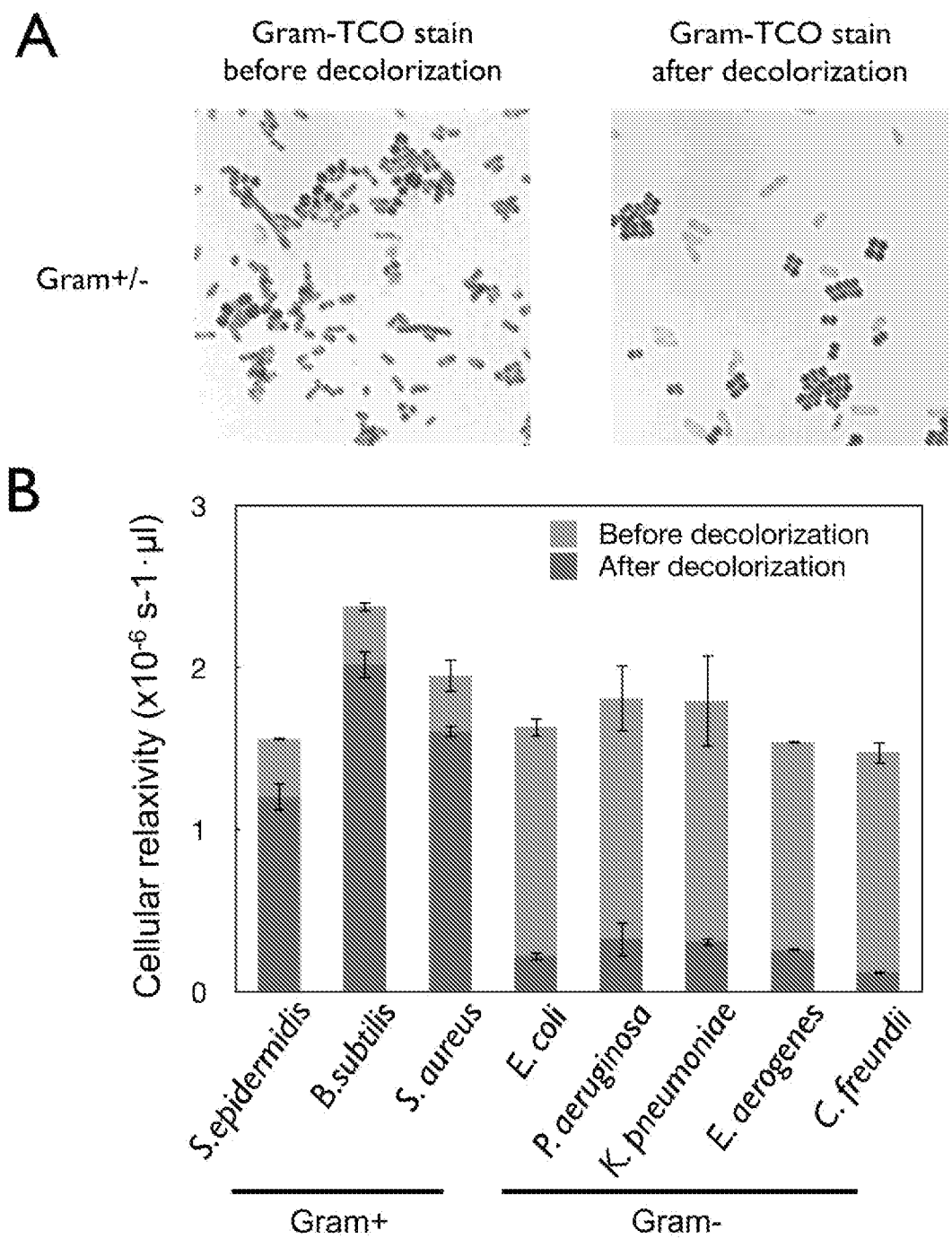
FIG. 18 shows the results of using crystal violet-TCO to detect both Gram positive and Gram-negative bacteria: (A) bright field images of a mixture of S. aureus (Gram-positive cocci) and E. coli (Gram-negative bacilli) after Gram staining using crystal violet-TCO, both before (left) and after (right) decolorization; and (B) μNMR detection of different species of Gram-positive and Gram-negative bacteria before (green+blue bar) and after decolorization (blue bar).

As shown in FIG. 16A, Crystal Violet-TCO stained Gram-positive bacteria showed uniform and high fluorescence signals in the bacterial cell wall, while the control experiments without CV-TCO showed no signal (FIG. 17). Similarly, transmission electron microscopy was performed in CV-TCO treated bacteria but which were incubated with tetrazine modified gold nanoparticles. Gold nanoparticles were used instead of magnetic nanoparticles to obtain higher contrast. Gold nanoparticles were found distributed throughout the bacterial surface treated with CV-TCO, while bacteria without CV-TCO labeling showed a smooth surface devoid of nanoparticles (FIG. 16B).

c. Detection of Both Gram-Positive and Gram-Negative Bacteria Via Magnetic Labeling Using Crystal Violet-TCO The magnetic labeling detection strategy using Crystal Violet-TCO can be applied to detect both Gram-positive and Gram-negative bacteria. A modified protocol was adopted in which staining was performed without the decolorization process, which results in labeling both Gram-positive and Grain-negative bacteria, since the Gram-negative bacteria also retain the Crystal Violet-TCO. This is similar to conventional Gram staining, where the first staining step colors all bacteria, with the second decolorization step allowing differentiation between the two Gram classes. The results of such experiments are shown in FIG. 18.

FIG. 18A shows bright field images of a mixture of *S. aureus* (Gram-positive cocci) and *E. coli* (Gram-negative bacilli) after Gram stain using Crystal Violet-TCO, before (left) and after (right) decolorization.

FIG. 18B shows µNMR detection of different species of Gram-positive and Gram-negative bacteria before (green+ blue bar) and after decolorization (blue bar). The µNMR measurements showed that before decolorization, both Gram-positive and negative bacteria could be magnetically labeled and detected, while after decolorization, only Gram-positive species retained their signals.

Through these sequential measurements, it is thus possible to obtain total bacterial counts (i.e., detection before decolorization) as well as their Gram-negative and Gram-positive composition (i.e., detection after decolorization).

Figure 19:
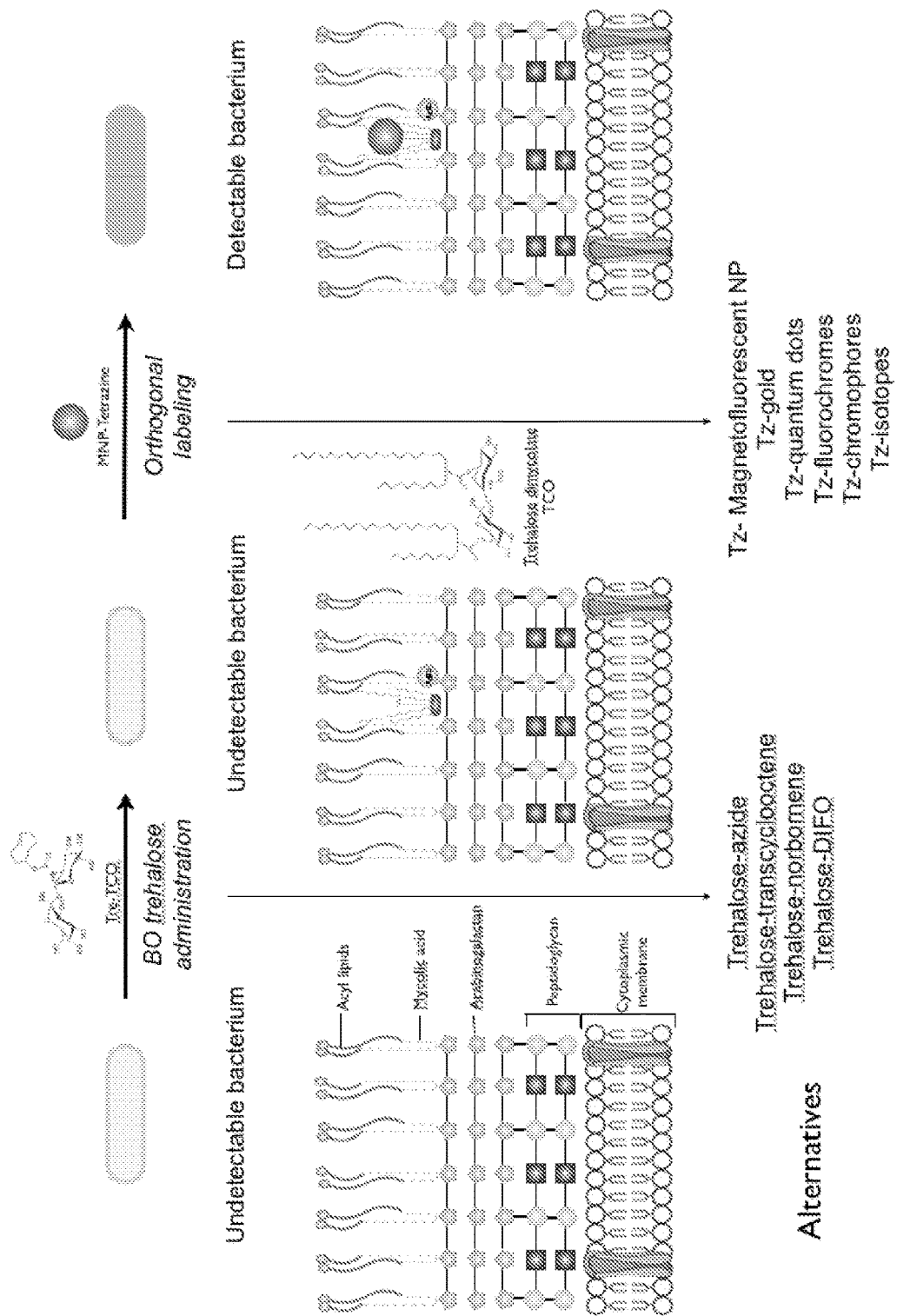
FIG. 19 shows the labeling scheme for trehalose. Trehalose-trans-cyclooctene (Tre-TCO) is incorporated into the bacterial membrane. Following incubation with MFNP-Tz, bacteria are labeled and can be detected via fluorescent or magnetic sensors.

Example 4. Magnetic Labeling Of Bacteria Using a Trehalose-Trans-Cyclooctene Conjugate The Example below describes labeling of bacteria using trans-cyclooctene (TCO) conjugates of trehalose. The labeling scheme for trehalose is shown in FIG. 19. Trehalose-trans-cyclooctene (Tre-TCO) is incorporated into the bacterial membrane. Following incubation with MFNP-Tz, bacteria are labeled and can be detected via fluorescent or magnetic sensors.

Figure 20:
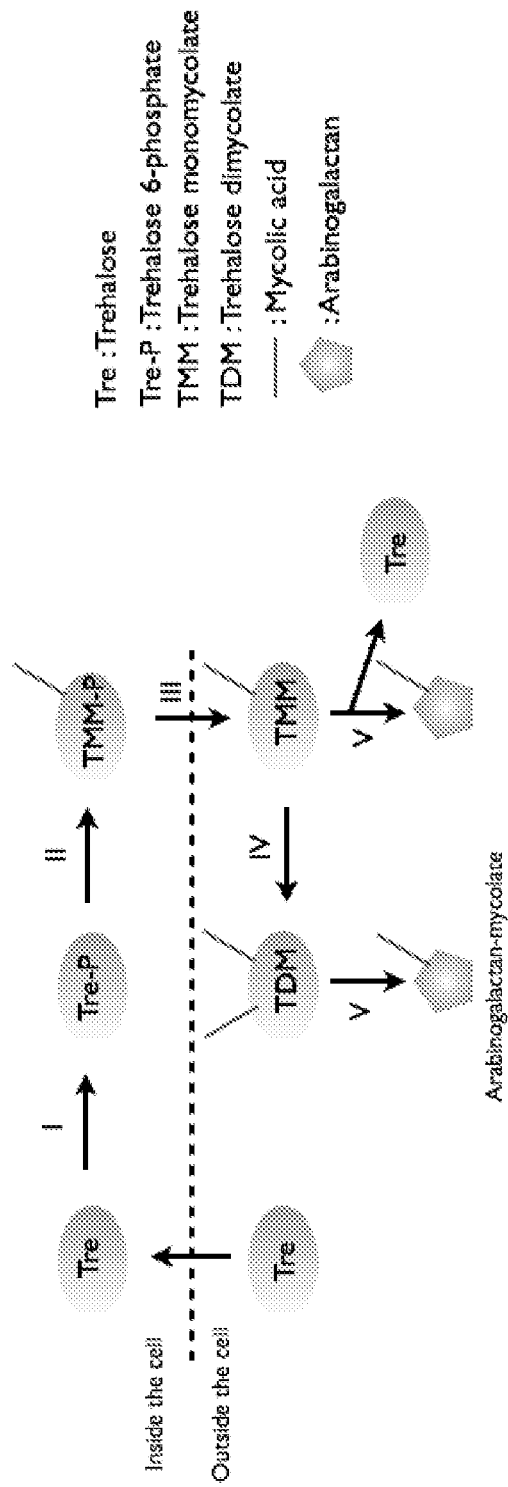
FIG. 20 shows a putative biochemical mechanism for the incorporation of trehalose analogues into the cell membrane.

FIG. 20 illustrates a putative biochemical mechanism for the incorporation of trehalose into the cell membrane. Trehalose enters the cell and is phosphorylated (reaction I) to produce Trehalose 6-phosphate (Tre-P). Newly synthesized mycolic acids are transferred to Tre-P to yield trehalose monomycolate 6-phosphate (TMM-P) by the membrane-associated mycolyltransferase II (reaction II). Trehalose monomycolate (TMM) is produced by dephosphorylation of TMM-P by the membrane-bound TMM-P phosphatase and is transported to the outside by a proposed ABC transporter cassette (TMM transporter) (reaction III). Outside the cell Ag85 complex catalyzes the transfer of mycolate to another TMM to yields trehalose dimycolate (TDM) (reaction IV) or to an arabinogalactan moiety to yield arabinogalactan-mycolate (reaction V).

Figure 21:
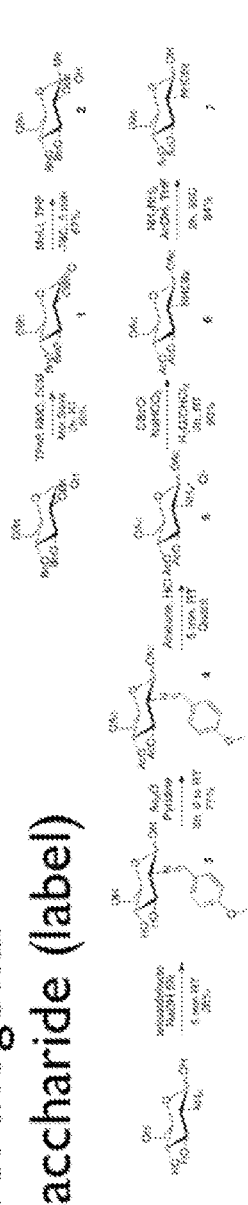
FIG. 21 shows synthetic routes for the synthesis of trehalose analogs and for magnetic nanoparticle and fluorescent reporters for labeling with trehalose analogs.
Figure 21:
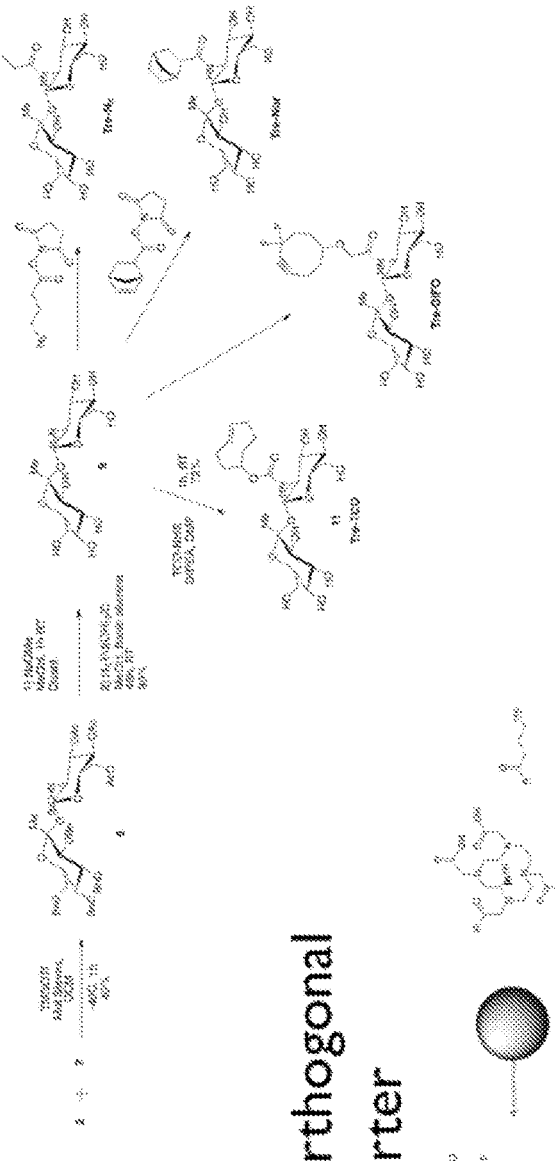
Figure 21:
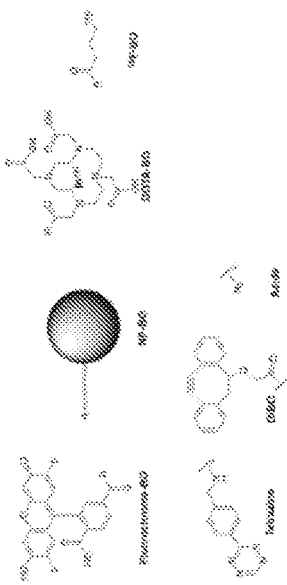

FIG. 21 illustrates synthetic routes for the synthesis of trehalose analogs and for magnetic nanoparticle and fluorescent reporters.

The synthesis of a specific trehalose derivative found to be useful for bacterial labeling, namely trehalose-trans-cyclooctene is described below.

All reagents were obtained from commercial sources and used without further purifications. Dry MeOH, DCM, THF, Pyridine and DMF were obtained from Aldrich. (E)-cyclooct-4-enyl 2,5-dioxopyrrolidin-1-yl carbonate (TCO—NHS) was prepared as described in Devaraj et al., *Bioconj. Chem.* 2008, 19, 2297-2299. MNFP-Tz was prepared as described by Josephson et al., *Bioconj. Chem.* 1999, 10, 186-191. Oregon Green was prepared as described by Devraj et al., *Angew. Chem. Int. Ed.*, 2010, 49, 2869-2872 and Devraj et al., *Angew. Chem., Int. Ed.* 2009, 48, 7013-7016, S7013/1-S7013/6.

1. Chemical Synthesis

2,3,4,6-tetra-O-benzyl-D-gluco-1,5-lactone

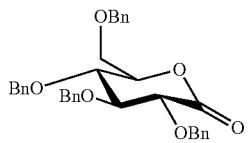

To a stirred solution of 2,3,4,6-tetra-O-benzyl-D-glucopyranose (4 g, 7.39 mmol) in DCM (62 mL) containing powdered molecular sieves (3A, 2 g) was added NMO (1.3 g, 11.09 mmol). After stirring for 10 min. at room temperature, TPAP (126 mg, 0.37 mmol) was added in one portion. Reaction was stirred for 2 h upon complete conversion. The reaction mixture was diluted with DCM and washed successively with a 5% solution of $Na_2SO_3$ in brine, brine and saturated $CuSO_4$. Organic layer was dried over $MgSO_4$, filtered and concentrated to dryness in vacuo to give 2,3,4,6-tetra-O-benzyl-D-gluco-1,5-lactone (3.78 g, 95%) as a light yellow oil. $^1$H NMR (400 MHz, $CDCl_3$) δ 7.44-7.26 (m, 18H), 7.25-7.19 (m, 2H), 5.02 (d, J=11.4 Hz, 1H), 4.75 (t, J=10.7 Hz, 2H), 4.67 (d, J=11.4 Hz, 1H), 4.63 (d, J=11.8 Hz, 1H), 4.57 (d, J=6.9 Hz, 1H), 4.53 (d, J=4.3 Hz, 1H), 4.51-4.46 (m, 2H), 4.16 (d, J=6.4 Hz, 1H), 3.97 (dt, J=16.8, 6.8 Hz, 2H), 3.73 (ddd, J=14.2, 11.0, 2.7 Hz, 2H). MS ESI m/z: [M+Na]$^+$=561.

3,4,5,7-Tetra-O-benzyl-1-deoxy-D-gluco-heptulopyranose

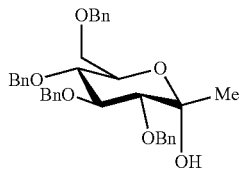

2,3,4,6-tetra-O-benzyl-D-gluco-1,5-lactone (2 g, 3.71 mmol) was dissolved in dry THF (46 mL) and cooled down to −78° C. A solution of methyllithium in THF (4.4 mL, 1.4N, 7.06 mmol, 1.9 eq.) was added dropwise and the mixture was stirred at −78° C. for 10 min. upon complete conversion. Reaction was quenched by the addition of a saturated solution of $NH_4Cl$ and extracted three times with ethyl acetate. The combined organic layers were washed with $H_2O$, brine, dried ($MgSO_4$), and concentrated in vacuo. The resulting oil was purified by column chromatography (silica gel, Hexanes:EtOAc 90/10 to 80/20) to provide 3,4,5,7-tetra-O-benzyl-1-deoxy-D-gluco-heptulopyranose (1.37 g, 67%) as a colorless oil. $^1$H NMR (400 MHz, $CDCl_3$) δ 7.44-7.29 (m, 18H), 7.23 (d, J=7.3 Hz, 2H), 4.99 (d, J=11.1 Hz, 1H), 4.98-4.93 (m, 1H), 4.89 (d, J=10.8 Hz, 1H), 4.76 (d, J=11.1 Hz, 1H), 4.67 (d, J=12.3 Hz, 1H), 4.62 (d, J=11.0 Hz, 1H), 4.58 (d, J=12.3 Hz, 1H), 4.09 (s, 1H), 4.08-4.00 (m, 1H), 3.81-3.67 (m, 3H), 3.43 (d, J=9.3 Hz, 1H), 2.94 (s, 1H), 1.47 (s, 3H). MS ESI m/z: [M+Na]$^+$=577.

2-Deoxy-2-{[(4-methoxyphenyl)methylidene]amino}-D-glucopyranose

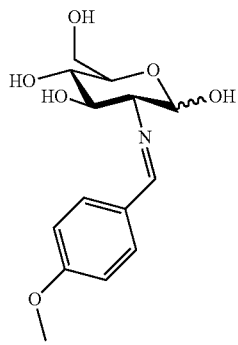

Glucosamine hydrochloride (15 g, 69.56 mmol) was dissolved in 5N aq. NaOH solution (15.3 ml, 76.52 mmol; 1.1 eq.) and treated with anisaldehyde (8.46 ml, 69.56 mmol, 1.0 eq.). After brief shaking (5 min.), the solution solidified and was kept at 4° C. overnight. The crystalline slurry was suction-filtered, and rinsed with $H_2O$ and small portions of diethyl ether/hexanes 2/1 to afford, after drying, a light yellow powder 2-deoxy-2-{[(4-methoxyphenyl)methylidene]amino}-D-glucopyranose (5.35 g, 26%). $^1$H NMR (400 MHz, DMSO) δ 8.08 (s, 1H), 7.65 (d, J=8.5 Hz, 2H), 6.95 (d, J=8.6 Hz, 2H), 6.48 (s, 1H), 4.88 (d, J=2.2 Hz, 1H), 4.77 (d, J=4.2 Hz, 1H), 4.66 (d, J=7.5 Hz, 1H), 4.50 (s, 1H), 3.76 (s, 3H), 3.69 (d, J=10.7 Hz, 1H), 3.50-3.33 (m, 2H), 3.23-3.15 (m, 1H), 3.12 (d, J=8.9 Hz, 1H), 2.76 (t, J=8.5 Hz, 1H). MS ESI m/z: [M+H]$^+$=298.

1,3,4,6-Tetra-O-acetyl-2-deoxy-2-{[(4-methoxyphenyl)methylidene]amino}-D-glucopyranose

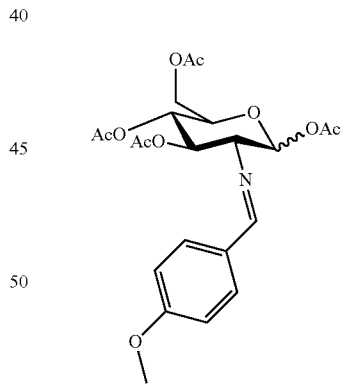

2-Deoxy-2-{[(4-methoxyphenyl)methylidene]amino}-D-glucopyranose (5 g, 16.83 mmol) was dissolved in anhydrous pyridine (14.3 ml) and cooled in an ice bath, and acetic anhydride (27.1 ml) was added in small portions under continuous stirring. The cooling bath was removed, and the mixture was stirred at room temperature for 3 h. Toluene was then added and the solvents were removed under reduced pressure. The remaining oil was repeatedly co-evaporated with toluene. The resulting yellowish solid was crystallized from ethanol to afford the title compound 1,3,4,6-tetra-O-acetyl-2-deoxy-2-{[(4-methoxyphenyl)methylidene]amino}-D-glucopyranose (6 g, 77%). $^1$H NMR (400 MHz, DMSO) δ 8.28 (s, 1H), 7.65 (d, J=8.7 Hz, 2H), 6.99 (d, J=8.7 Hz, 2H), 6.07 (d, J=8.2 Hz, 1H), 5.44 (t, J=9.7 Hz, 1H), 4.97 (t, J=9.6 Hz, 1H), 4.31-4.17 (m, 2H), 4.01 (d, J=11.1 Hz, 1H), 3.79 (s, 3H), 3.49-3.40 (m, 1H), 2.02 (s, 3H), 1.98 (s, 6H), 1.82 (s, 3H). MS ESI m/z: [M+H]$^+$=466.

1,3,4,6-Tetra-O-acetyl-β-D-glucosamine Hydrochloride

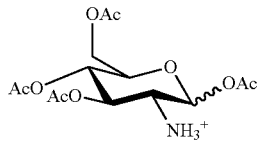

1,3,4,6-Tetra-O-acetyl-2-deoxy-2-{[(4-methoxyphenyl)methylidene]amino}-D-glucopyranose (6 g, 12.90 mmol) was dissolved in hot acetone (43 mL), and treated with conc. HCl (1.2 ml, 1.1 eq.) under vigorous stirring. The immediately solidifying mass was cooled to room temperature, stirred with diethyl ether/hexanes, and kept overnight at 4° C. After suction-filtration, the crystalline mass was washed with cold diethyl ether/hexanes and then hexanes to yield a white powder 1,3,4,6-tetra-O-acetyl-β-D-glucosamine Hydrochloride (4.93 g, Quant.). $^1$H NMR (400 MHz, DMSO) δ 8.72 (s, 2H), 5.90 (d, J=8.7 Hz, 1H), 5.35 (t, J=9.8 Hz, 1H), 4.93 (t, J=9.6 Hz, 1H), 4.19 (dd, J=12.5, 4.3 Hz, 1H), 4.05 (dd, J=10.2, 4.2 Hz, 1H), 4.00 (d, J=12.5 Hz, 1H), 3.57 (t, J=9.5 Hz, 1H), 2.17 (s, 3H), 2.03 (s, 3H), 2.00 (s, 3H), 1.98 (s, 3H). MS ESI m/z: [M+H]$^+$=348.

1,3,4,6-Tetra-O-acetyl-2-{[(benzyloxy)carbonyl]amino}-2-deoxy-O-D-glucopyranose

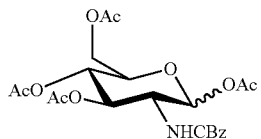

2-Deoxy-2-{[(4-methoxyphenyl)methylidene]amino}-D-glucopyranose (5.03 g, 13.14 mmol) was dissolved in CHCl$_3$ (26 ml) and H$_2$O (52 ml) in the presence of solid NaHCO$_3$ (2.76 g, 32.85 mmol, 2.5 eq.) and benzylchlorocarbonate (CBzCl; 2.81 mL, 19.71 mmol, 1.5 eq.). The mixture was stirred for 3 h at room temperature, while maintaining the pH at 8.0, until TLC showed the disappearance of the starting material. The mixture was acidified to pH 1.5±2.0, and then extracted several times with CHCl$_3$. The combined organic layers were washed with HCl 1N, saturated NaHCO$_3$ solution, and brine, dried (MgSO$_4$), and concentrated in vacuo. The remaining solid was taken up in Hexanes and filtered to yield 1,3,4,6-tetra-O-acetyl-2-{[(benzyloxy)carbonyl]amino}-2-deoxy-β-D-glucopyranose (5.67 g, 90%) as a white powder. $^1$H NMR (400 MHz, DMSO) δ 7.49 (d, J=9.6 Hz, 1H), 7.39-7.23 (m, 5H), 5.68 (d, J=8.8 Hz, 1H), 5.16 (t, J=9.9 Hz, 1H), 5.04 (d, J=3.2 Hz, 2H), 4.89 (t, J=9.7 Hz, 1H), 4.18 (dd, J=12.5, 4.4 Hz, 1H), 3.98 (d, J=12.6 Hz, 1H), 3.95-3.89 (m, 1H), 3.68 (dd, J=19.1, 9.3 Hz, 1H), 2.00 (s, 6H), 1.97 (s, 3H), 1.86 (s, 3H). MS ESI m/z: [M+H]$^+$=482.

3,4,6-Tri-O-acetyl-2-{[benzyloxy)carbonyl]amino}-2-deoxy-O-D-glucopyranose

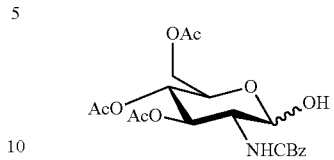

To a solution of 1,3,4,6-tetra-O-acetyl-2-{[(benzyloxy)carbonyl]amino}-2-deoxy-β-D-glucopyranose 6 (3 g, 6.23 mmol) in THF (52 mL), was added hydrazine acetate (643 mg, 6.98 mmol, 1.12 eq.). The reaction mixture was stirred at 55° C. for 2 h, then cooled to room temperature, diluted with EtOAc (50 mL) and extracted with a saturated solution of NaHCO$_3$. The organic layer was washed with H$_2$O, brine dried with MgSO$_4$, filtered and concentrated. The resulting solid was purified by column chromatography (silica gel, Hexanes:EtOAc 70/30 to 50/50) to provide 3,4,6-tri-O-acetyl-2-{[(benzyloxy)carbonyl]amino}-2-deoxy-β-D-glucopyranose (2.31 g, 84%) as a white powder containing a mixture of two anomers. $^1$H NMR (400 MHz, cdcl$_3$) δ 7.36-7.27 (m, 5H), 5.30-5.20 (m, 3H), 5.14-5.04 (m, 3H), 5.00 (d, J=12.3 Hz, 1H), 4.32 (s, 1H), 4.22-4.15 (m, 2H), 4.10 (dd, J=14.0, 6.6 Hz, 2H), 4.00 (td, J=10.3, 3.0 Hz, 1H), 2.06 (s, 3H), 2.02 (s, 1H), 1.99 (s, 3H), 1.88 (s, 3H). MS ESI m/z: [M−H]$^-$=438.

3,4,5,7-tetra-O-benzyl-1-deoxy-α-D-gluco-hept-2-ulopyranosyl-(2→1)-3,4,6-tetra-O-acetyl-2-benzyloxycarbonylamino-2-deoxy-α-D-glucopyranoside

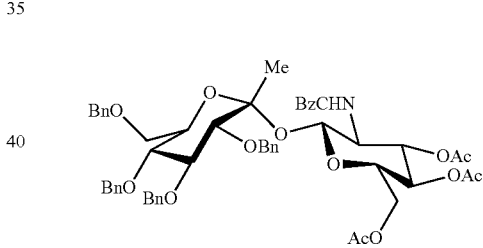

Compounds 3,4,5,7-Tetra-O-benzyl-1-deoxy-D-glucoheptulopyranose (200 mg, 0.36 mmol, 1 eq.) and 3,4,6-Tri-O-acetyl-2-{[(benzyloxy)carbonyl]amino}-2-deoxy-β-D-glucopyranose (190 mg, 0.43 mmol, 1.2 eq.) were dried under reduced pressure for 1 h and then dissolved in anhydrous DCM (12 mL) and added to a dry flask in the presence of molecular sieves (ca. 200 mg). Mixture was stirred with molecular sieves for 30 min. at room temperature and then was cooled to −40° C. To this was added TMSOTf (65 µl, 0.36 mmol, 1 eq.) at −40° C. in the under an Ar atmosphere. The resulting mixture was stirred for 15 min. The reaction was then quenched by the addition of Et$_3$N (650 µL), filtered through diatomaceous earth and concentrated. The crude product was purified by column chromatography (hexanes:EtOAc 9/1 to 5/5) to yield the desired compound 3,4,5,7-tetra-β-benzyl-1-deoxy-α-D-gluco-hept-2-ulopyranosyl-(2→1)-3,4,6-tetra-O-acetyl-2-benzyloxycarbonylamino-2-deoxy-α-D-glucopyranoside (141 mg, 40%) as a white powder. $^1$H NMR (400 MHz, CDCl$_3$) δ 7.17-7.03 (m, 18H), 6.99 (s, 2H), 5.18 (d, J=3.0 Hz, 1H), 5.16-5.07 (m, 1H), 4.96-4.83 (m, 2H), 4.80 (d, J=11.0 Hz, 1H), 4.75 (s, 2H), 4.64 (d, J=11.0 Hz, 1H), 4.46-4.39 (m, 1H), 4.36 (d, J=12.5 Hz, 1H), 4.20 (d, J=12.2 Hz, 1H), 4.09 (d, J=9.5 Hz, 1H), 3.86 (dd, J=12.4, 4.5 Hz, 2H), 3.80 (t, J=9.0 Hz, 1H), 3.64-3.48 (m, 3H), 3.36 (d, J=9.4 Hz, 1H), 3.25 (d, J=10.9 Hz, 1H), 3.16 (d, J=9.5 Hz, 1H), 1.86 (s, 3H), 1.83 (s, 3H), 1.79 (s, 3H), 1.31 (s, 3H). MS ESI m/z: [M+Na]$^+$=998.

1-deoxy-α-D-gluco-hept-2-ulopyranosyl-(2→1)-2-amino-2-deoxy-α-D-glucopyranoside glucopyranoside

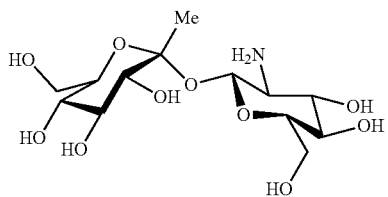

3,4,5,7-tetra-O-benzyl-1-deoxy-α-D-gluco-hept-2-ulopyranosyl-(2→1)-3,4,6-tetra-β-acetyl-2-benzyloxycarbonylamino-2-deoxy-α-D-glucopyranoside (50 mg, 0.050 mmol, 1 eq.) was dissolved in anhydrous MeOH (1.3 mL). To this was added sodium methoxide (2.6 mg, 0.048 mmol, 0.94 eq.) and reaction was stirred for 1 h at room temperature, upon which time full conversion to product was detected by LCMS. Reaction was neutralized with DOWEX 5 0WX8 (H+ form) cation exchange resin (ca. 10 mg). DOWEX was removed by filtration and reaction was concentrated under reduced pressure to yield the deacetylated product (43 mg, Quant.). This product was dissolved in 10 mL of degassed MeOH. Solution was further degassed for 15 min. before the addition of Pd(OH)$_2$/C (86 mg) and basic alumina (43 mg). Reaction was stirred under H$_2$ for 48 h at room temperature upon which time full conversion to product was detected by LCMS. Reaction was filtered through diatomaceous earth and concentrated under reduced pressure and purified by LCMS to yield the desired compound 1-deoxy-α-D-gluco-hept-2-ulopyranosyl-(2→1)-2-amino-2-deoxy-α-D-glucopyranoside glucopyranoside (16 mg 90%), as a white amorphous solid. $^1$H NMR (400 MHz, D$_2$O) δ 5.30 (d, J=1.4 Hz, 1H), 3.93-3.65 (m, 8H), 3.44 (dd, J=18.9, 9.4 Hz, 2H), 3.32 (d, J=9.8 Hz, 1H), 2.76 (dd, J=10.0, 2.3 Hz, 1H), 2.44 (s, 1H), 1.57 (s, 3H). MS ESI m/z: [M+Na]$^+$=378.

1-deoxy-α-D-gluco-hept-2-ulopyranosyl-(2→1)-2-deoxy-2-((E)-cyclooct-4-en-1-yl carbamate)-α-D-glucopyranoside

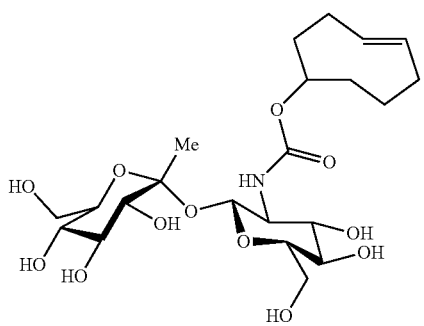

1-deoxy-α-D-gluco-hept-2-ulopyranosyl-(2→1)-2-amino-2-deoxy-α-D-glucopyranoside glucopyranoside (2.3 mg, 6.5 μmol), TCO—NHS (87 μL of 10 mg/mL solution in DMF, 3.2 μmol) and DIPEA (1.7 μL, 9.7 μmol) were dissolved in 250 μL DMF and stirred for 1 h at room temperature. The mixture was purified by HPLC affording 1-deoxy-α-D-gluco-hept-2-ulopyranosyl-(2→1)-2-deoxy-2-((E)-cyclooct-4-en-1-yl carbamate)-α-D-glucopyranoside (1.2 mg, 72%) as a white solid. $^1$H NMR (400 MHz, D$_2$O) δ 5.78-5.66 (m, 1H), 5.64-5.50 (m, 1H), 5.29 (dd, J=7.1, 3.7 Hz, 1H), 4.34-4.22 (m, 1H), 3.92-3.57 (m, 8H), 3.54-3.44 (m, 2H), 3.31 (d, J=9.8 Hz, 1H), 2.44-2.29 (m, 2H), 2.23-2.15 (m, 2H), 2.04-1.86 (m, 4H), 1.75-1.58 (m, 3H), 1.53 (s, 3H). MS ESI m/z: [M−H]$^-$=506.

2. Bioorthogonal Labeling of Bacteria Using Trehalose-TCO; Observation of Labeling by Cell Fluorescence Microscopy To prove the principle of bioorthogonal labeling of bacteria using trehalose-TCO, *Nocardia Farcinica* was used a surrogate, non-pathogenic bacterium that resembles *M. Tuberculosis* in its capability for incorporating trehalose.

*Nocardia Farcinica* bacteria (ATCC 3308) at an OD$_{600}$ of 0.8 in growth medium (0.1 mL) was added 100 μM Trehalose-TCO, Trehalose-fluorescein or DMSO (as a control) in growth media (1% DMSO). Bacteria were incubated at 37° C. with shaking for 16 h. Bacteria were then centrifuged (7 min., 8000 rpm) and washed (2×100 μL PBS solution containing 2% fetal bovine serum (FBS) and 1 mg/mL bovine serum albumin (BSA) PBS-F).

Bacteria treated with Trehalose-TCO were incubated with 50 μg/mL MFNP-Tz MNFP-Tz or 10 μM Oregon Green-Tz for 20 min. in PBS-F. Bacteria were then centrifuged (7 min., 8000 rpm) and washed (2×100 μL PBS-F). Bacteria were then fixed with 10% PFA in PBS (100 μL) for 20 min., centrifuged and resuspended in 10 μL PBS. 3 μL were spread out on a 96 wells plates (Nunc, Cat No 137103 (Roskilde, Denmark, pre-wet with PBS-F). Bacteria were dried out in an incubator 37 C for 30 min. then mounting media containing Propidium bromide was added to samples. Imaging was done on a DeltaVision microscope (Applied Precision Instruments) at 60×.

Figure 22:
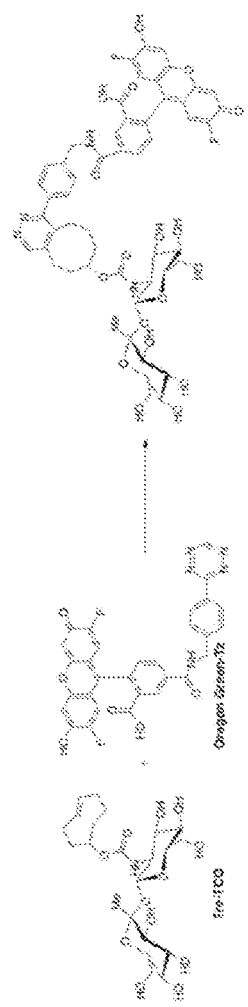
FIG. 22 shows the results of labeling Nocardia Farcinica bacteria with Trehalose-TCO/Oregon Green-Tz and a control experiment where cells were treated with Oregon Green-Tz without prior treatment with Trehalose-CO.
Figure 22:
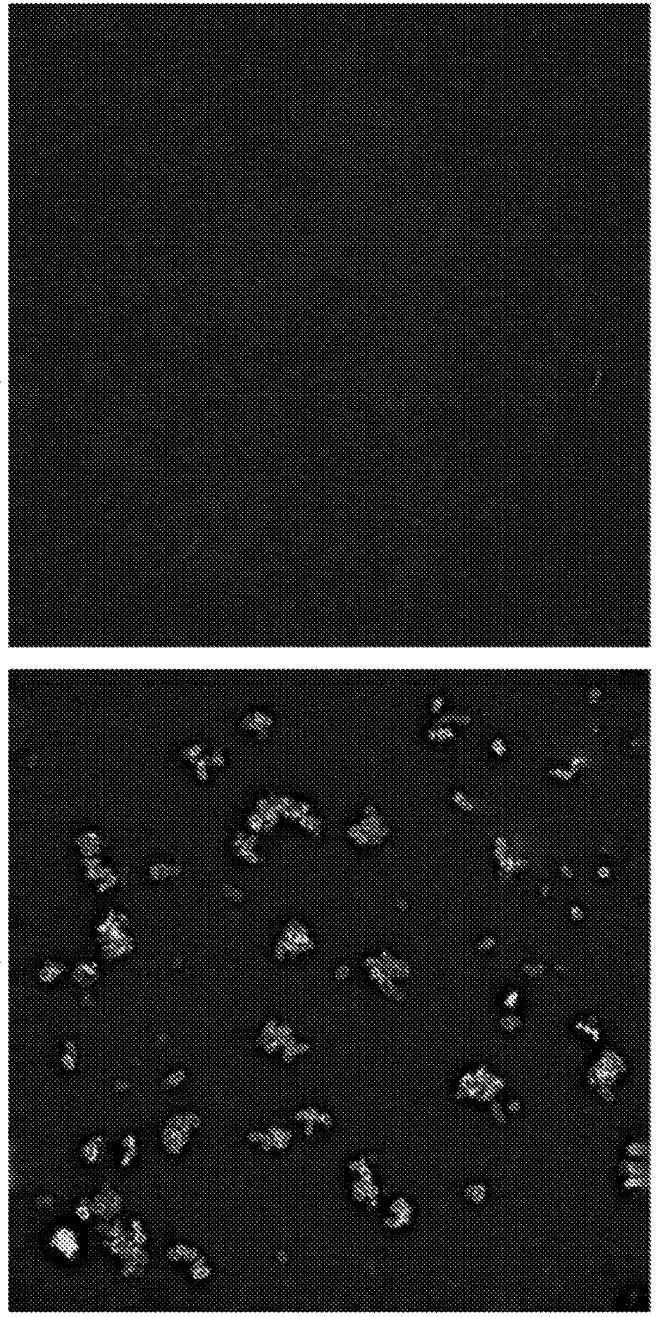

The results of labeling with Trehalose-TCO/Oregon Green-Tz are shown in FIG. 22. The left hand panel shows the results of labeling with Trehalose-TCO (Tre-TCO) followed by Oregon Green-Tz (OG-Tz). Bright green fluorescence of the cells is observed. The right panel shows the results of Oregon Green-Tz without prior treatment with Trehalose-CO.

Figure 23:
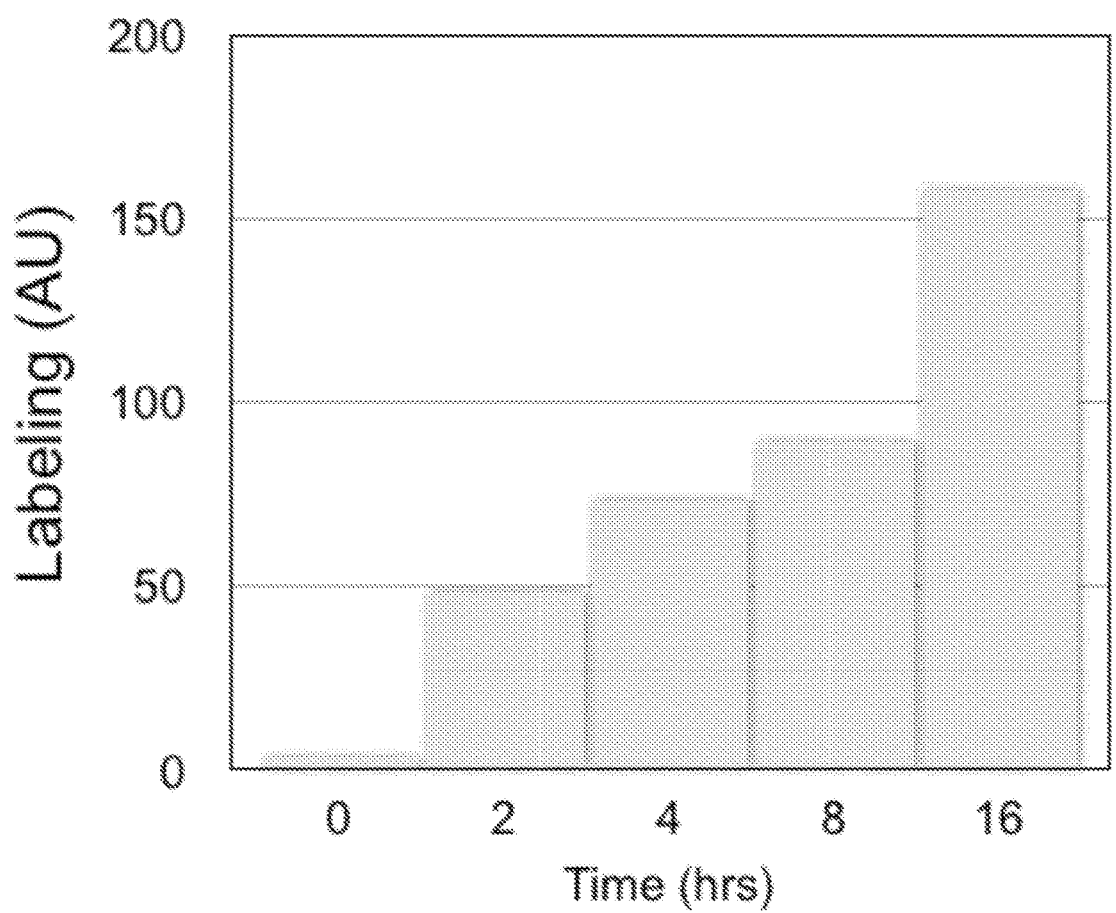
FIG. 23 shows the kinetics of incorporation of trehalose-TCO as measured by subsequent labeling with Oregon Green-Tz.

Finally, FIG. 23 shows the kinetics of incorporation of trehalose-TCO as measured by subsequent labeling with Oregon Green-Tz. A gradual increase in the extent of labeling is observed over a period of 0-16 h.

All publications, patent applications, patents and other references mentioned herein are incorporated by reference in their entirety.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages and modifications are within the scope of the following claims.

What is claimed is:

1. An affinity ligand that is a compound of the formula (V):

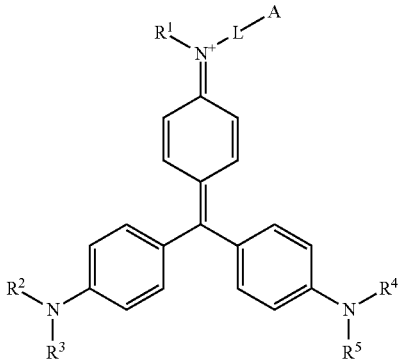

wherein:

$R^1$ is hydrogen or $(C_1-C_6)$alkyl;

$R^2$ is $(C_1-C_6)$alkyl;

$R^3$ is $(C_1-C_6)$alkyl;

$R^4$ is $(C_1-C_6)$alkyl;

$R^5$ is $(C_1-C_6)$alkyl;

A is a chemical moiety comprising a 1,2,4,5-tetrazine group, a trans-cyclooctene group or a cyclooctyne group; and L is a bond or a linking group.

2. The affinity ligand of claim 1, which is a compound according to the following formula:

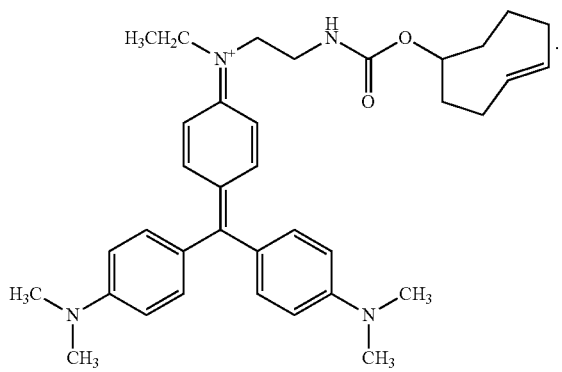

3. A kit for the magnetic labeling of a bacterial cell comprising:

an affinity ligand according to claim 1 of the formula (V):

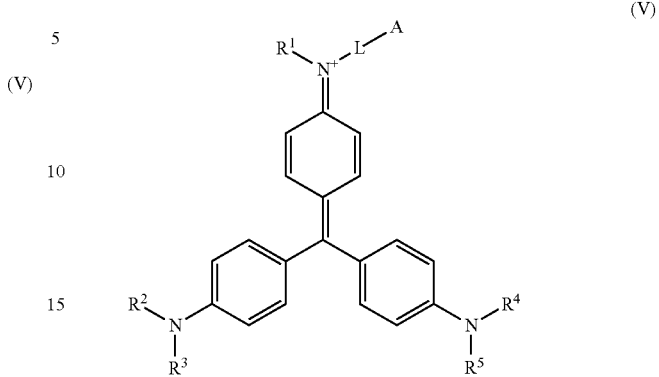

wherein $R^1$, $R^2$, $R^3$, $R^4$, $R^5$, L and A are as defined in claim 1; and a magnetic agent of the formula (II):

$$B-M \qquad (II)$$

wherein:

M is a magnetic particle; and

B is a chemical moiety comprising a 1,2,4,5-tetrazine group, a trans-cyclooctene group or a cyclooctyne group that is covalently attached to the magnetic particle;

wherein one of A and B comprises a 1,2,4,5-tetrazine group and the other of A and B comprises a trans-cyclooctene group or a cyclooctyne group.

4. The kit of claim 3, wherein the affinity ligand is a compound according to the following formula:

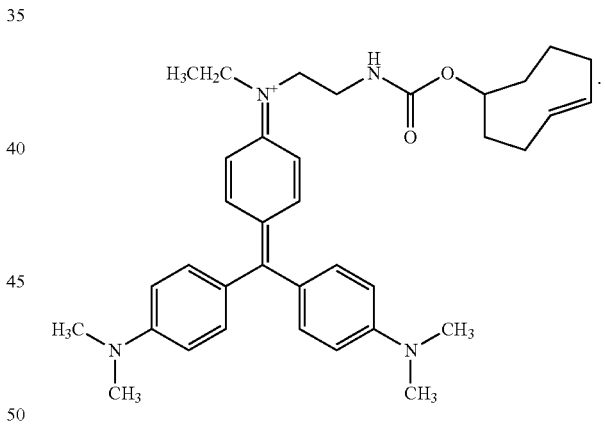

5. The affinity ligand of claim 1, wherein $R^1$ is hydrogen, methyl or ethyl.

6. The affinity ligand of claim 5, wherein $R^1$ is ethyl.

7. The affinity ligand of claim 5, wherein $R^2$ is methyl, $R^3$ is methyl, $R^4$ is methyl and $R^5$ is methyl.

8. The affinity ligand of claim 5, wherein L-A is according to the following formula:

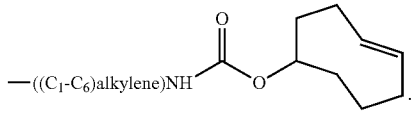

9. The affinity ligand of claim 8, wherein L-A is according to the following formula:

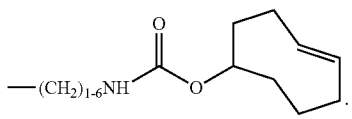

10. The affinity ligand of claim 9, wherein L-A is according to the following formula:

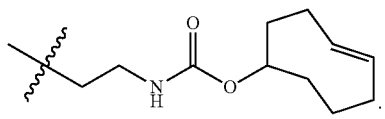 [SMILES: *CCNC(=O)OC1CC/C=C/CCC1]

11. The method of claim 3, wherein the bacteria are Gram positive bacteria.
12. The kit of claim 3, wherein $R^1$ is hydrogen, methyl or ethyl.
13. The kit of claim 12, wherein $R^1$ is ethyl.
14. The kit of claim 12, wherein $R^2$ is methyl, $R^3$ is methyl, $R^4$ is methyl and $R^5$ is methyl.
15. The kit of claim 12, wherein L-A is according to the following formula:

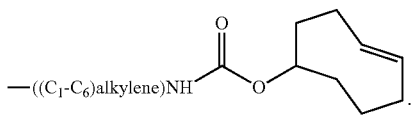

16. The kit of claim 15, wherein L-A is according to the following formula:

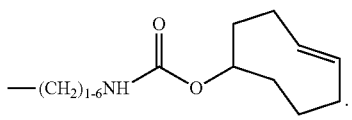

17. The kit of claim 16, wherein L-A is according to the following formula:

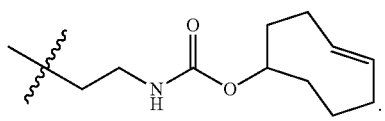

18. The kit of claim 11, wherein the magnetic particle comprises a magnetic iron oxide.
19. The kit of claim 11, wherein the magnetic particle is an amino-derivatized cross-linked iron oxide particle.
20. The kit of claim 11, wherein the magnetic particle is an iron oxide particle derivatized with a 1,2,4,5-tetrazine.
21. An affinity ligand that is a compound of the formula (I):

T-L-A  (I)

wherein:
T is a targeting group comprising crystal violet;
A is a chemical moiety comprising a 1,2,4,5-tetrazine group, a trans-cyclooctene group or a cyclooctyne group; and
L is a bond or a linking group attaching A to T.

22. A method for the magnetic labeling of a bacterial cell comprising:
contacting the bacterial cell with an affinity ligand according to claim 21; and
subsequently contacting the bacterial cell with a magnetic agent of the formula (II):

B-M  (II)

wherein:
M is a magnetic particle; and
B is a chemical moiety comprising a 1,2,4,5-tetrazine group, a trans-cyclooctene group or a cyclooctyne group that is covalently attached to the magnetic particle;
wherein one of A and B comprises a 1,2,4,5-tetrazine group and the other of A and B comprises a trans-cyclooctene group or a cyclooctyne group; and
wherein the contacting with the magnetic agent is carried out under conditions sufficient for A and B to react with each other via a [4+2] cycloaddition reaction.

23. A kit for the magnetic labeling of a bacterial cell comprising:
an affinity ligand according to claim 21; and
a magnetic agent of the formula (II):

B-M  (II)

wherein:
M is a magnetic particle; and
B is a chemical moiety comprising a 1,2,4,5-tetrazine group, a trans-cyclooctene group or a cyclooctyne group that is covalently attached to the magnetic particle;
wherein one of A and B comprises a 1,2,4,5-tetrazine group and the other of A and B comprises a trans-cyclooctene group or a cyclooctyne group.

24. A method for the magnetic labeling of a bacterial cell comprising:
contacting the bacterial cell with an affinity ligand according to claim 1 of the formula (V):

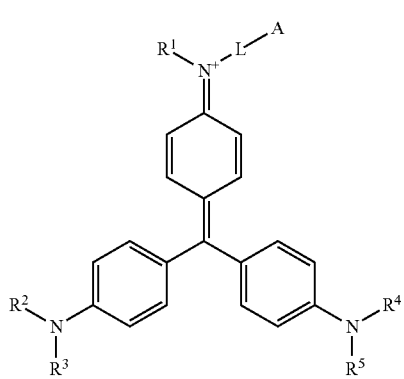

wherein $R^1$, $R^2$, $R^3$, $R^4$, $R^5$, L and A are as defined in claim 1; and
subsequently contacting the bacterial cell with a magnetic agent of the formula (II):

B-M  (II)

wherein:
M is a magnetic particle; and
B is a chemical moiety comprising a 1,2,4,5-tetrazine group, a trans-cyclooctene group or a cyclooctyne group that is covalently attached to the magnetic particle;
wherein one of A and B comprises a 1,2,4,5-tetrazine group and the other of A and B comprises a trans-cyclooctene group or a cyclooctyne group; and
wherein the contacting with the magnetic agent is carried out under conditions sufficient for A and B to react with each other via a [4+2] cycloaddition reaction.

25. The method of claim 24, wherein one of A and B comprises a 1,2,4,5-tetrazine group and the other of A and B comprises a trans-cyclooctene group.

26. The method of claim 24, wherein one of A and B comprises a 1,2,4,5-tetrazine group and the other of A and B comprises a cyclooctyne group.

27. The method of claim 24, wherein the affinity ligand is a compound according to the following formula:

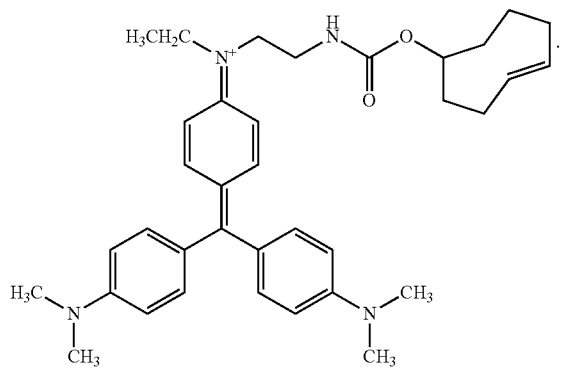

28. The method of claim 24, wherein the magnetic particle comprises a magnetic iron oxide.

29. The method of claim 28, wherein the magnetic particle is an amino-derivatized cross-linked iron oxide particle.

30. The method of claim 28, wherein the magnetic particle is an iron oxide particle derivatized with a 1,2,4,5-tetrazine.

31. The method of claim 24, wherein $R^1$ is hydrogen, methyl or ethyl.

32. The method of claim 31, wherein $R^1$ is ethyl.

33. The method of claim 31, wherein $R^2$ is methyl, $R^3$ is methyl, $R^4$ is methyl and $R^5$ is methyl.

34. The method of claim 31, wherein L-A is according to the following formula:

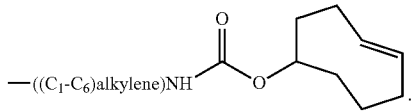

35. The method of claim 34, wherein L-A is according to the following formula:

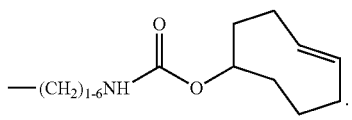

36. The method of claim 35, wherein L-A is according to the following formula:

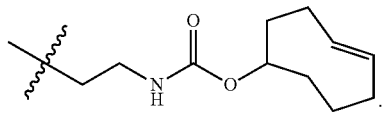 [SMILES: *CCNC(=O)OC1CC/C=C/CCC1]

37. The method of claim 31, wherein the bacteria are Gram positive bacteria.

* * * * *

UNITED STATES PATENT AND TRADEMARK OFFICE
CERTIFICATE OF CORRECTION

PATENT NO. : 10,274,490 B2  
APPLICATION NO. : 14/407300  
DATED : April 30, 2019  
INVENTOR(S) : Ghyslain Budin et al.

Page 1 of 1

It is certified that error appears in the above-identified patent and that said Letters Patent is hereby corrected as shown below:

On the Title Page

Column 2 item (57) (Abstract), Line 2, delete "call" and insert -- cell --

In the Specification

In Column 1, Line 11 (approx.), delete "2012" and insert -- 2012. --

Signed and Sealed this
Twentieth Day of August, 2019

Andrei Iancu
*Director of the United States Patent and Trademark Office*